US012605429B2

(12) United States Patent
Avci et al.

(10) Patent No.: US 12,605,429 B2
(45) Date of Patent: Apr. 21, 2026

(54) PROTEINS HAVING PNEUMOCOCCAL CAPSULE DEGRADING ACTIVITY AND METHODS OF USE

(71) Applicant: UNIVERSITY OF GEORGIA RESEARCH FOUNDATION, INC., Athens, GA (US)

(72) Inventors: Fikri Y. Avci, Watkinsville, GA (US); Dustin Middleton, Athens, GA (US); Amy Victoria Paschall, Washington, GA (US)

(73) Assignee: UNIVERSITY OF GEORGIA RESEARCH FOUNDATION, INC., Athens, GA (US)

( * ) Notice: Subject to any disclaimer, the term of this patent is extended or adjusted under 35 U.S.C. 154(b) by 318 days.

(21) Appl. No.: 18/199,685

(22) Filed: May 19, 2023

(65) Prior Publication Data

US 2024/0024435 A1     Jan. 25, 2024

Related U.S. Application Data

(63) Continuation of application No. 16/636,503, filed as application No. PCT/US2018/046521 on Aug. 13, 2018, now Pat. No. 11,690,900.

(60) Provisional application No. 62/652,046, filed on Apr. 3, 2018, provisional application No. 62/545,094, filed on Aug. 14, 2017.

(51) Int. Cl.
| | |
|---|---|
| *A61K 38/47* | (2006.01) |
| *A61P 31/04* | (2006.01) |
| *C12N 1/20* | (2006.01) |
| *C12N 9/24* | (2006.01) |

(52) U.S. Cl.
CPC .............. *A61K 38/47* (2013.01); *A61P 31/04* (2018.01); *C12N 1/20* (2013.01); *C12N 9/2402* (2013.01); *C12Y 302/01031* (2013.01); *C12N 2510/00* (2013.01)

(58) Field of Classification Search
None
See application file for complete search history.

(56) References Cited

U.S. PATENT DOCUMENTS

| | | | |
|---|---|---|---|
| 4,703,004 | A | 10/1987 | Hopp et al. |
| 4,782,137 | A | 11/1988 | Hopp et al. |
| 5,594,115 | A | 1/1997 | Sharma |
| 5,935,824 | A | 8/1999 | Sgarlato |
| 6,194,389 | B1 | 2/2001 | Johnston et al. |
| 6,238,661 | B1 | 5/2001 | Fischetti et al. |
| 6,423,299 | B1 | 7/2002 | Fischetti et al. |
| 6,752,988 | B1 | 6/2004 | Fischetti et al. |
| 7,569,223 | B2 | 8/2009 | Fischetti et al. |
| 11,690,900 | B2 | 7/2023 | Avci et al. |

| | | | |
|---|---|---|---|
| 2016/0015466 | A1 | 1/2016 | Park et al. |
| 2016/0115466 | A1 | 4/2016 | Taylor et al. |
| 2021/0308233 | A1 | 10/2021 | Avci et al. |

FOREIGN PATENT DOCUMENTS

| | | | | |
|---|---|---|---|---|
| CN | 1636062 | A | 7/2005 | |
| CN | 105121645 | A | 12/2015 | |
| CN | 105131139 | A | 12/2015 | |
| CN | 106102770 | A | 11/2016 | |
| WO | WO-2015032911 | A1 * | 3/2015 | ............. C12N 15/52 |
| WO | WO-2019036373 | A2 | 2/2019 | |
| WO | WO-2019036373 | A3 | 3/2020 | |

OTHER PUBLICATIONS

Middleton et al., "Enzymatic hydrolysis of pneumococcal type III polysaccharide", SFG 2016 Abstracts, 1 page.
Sickles et al., "A Systematic Study of Microorganisms which Decompose the Specific Carbohydrates of the Pneumococcus" J Bacteriology, 28(4):415-31.
Francis, Jr. et al., "Experimental Type III Pneumococcus Pneumonia in Monkeys, II. Treatment with an Enzyme Which Decomposes the Specific Capsular Polysaccharide of Pneumococcus Type III" Feb. 1, 1934; 641-68. 31 pages.
Goodner et al., "The Action of a Specific Enzyme upon the Dermal Infection of Rabbits with Type III Pneumococcus" Dec. 10, 1931; 393-404. 12 pages.
International Search Report and Written Opinion of PCT/US2018/046521 dated Dec. 21, 2018, 15 pages.
International Preliminary Report on Patentability for PCT/US2018/046521 dated Feb. 25, 2020, 10 pages.
European Search Report for EP Appl. No. 18847100.7-1118/3668309 dated Apr. 30, 2021, 15 pages.
Abeyta et al., Genetic alteration of capsule type but not PspA type affects accessibility of surface-bound complement and surface antigens of *Streptococcus pneumoniae*. Infect Immun 71, 218-225 (2003).
Agard et al., A comparative study of bioorthogonal reactions with azides. ACS Chem Biol 1, 644-648 (2006).
Alicino et al., The impact of 10-valent and 13-valent pneumococcal conjugate vaccines on hospitalization for pneumonia in children: A systematic review and meta-analysis. Vaccine 35, 5776-5785 (2017).

(Continued)

*Primary Examiner* — Oluwatosin A Ogunbiyi
(74) *Attorney, Agent, or Firm* — Mueting Raasch Group

(57) ABSTRACT

Provided herein is a protein, referred to as a Pn3Pase protein, that degrades the capsular polysaccharide of serotype 3 *Streptococcus pneumoniae*. The disclosure includes a genetically modified cell that includes a Pn3Pase protein, and compositions that include the protein, the polynucleotide encoding the protein, the genetically modified cell, or a combination thereof. Also provided are methods for using a Pn3Pase protein, including methods for contacting a *S. pneumoniae* having a type III capsular polysaccharide with a Pn3Pase protein, increasing deposition of at least one complement component on the surface of a *S. pneumoniae*, treating an infection in a subject, treating a symptom in a subject, decreasing colonization of a subject by *S. pneumoniae*, or a combination thereof.

19 Claims, 34 Drawing Sheets

Specification includes a Sequence Listing.

(56) References Cited

OTHER PUBLICATIONS

Allard et al., In situ evaluation of Paenibacillus alvei in reducing carriage of *Salmonella enterica* serovar Newport on whole tomato plants. Appl Environ Microbiol 80, 3842-3849 (2014).

Ash et al., Molecular identification of rRNA group 3 bacilli (Ash, Farrow, Wallbanks and Collins) using a PCR probe test. Proposal for the creation of a new genus Paenibacillus. Antonie Van Leeuwenhoek 64, 253-260 (1993).

Austrian, Some aspects of the pneumococcal carrier state. J Antimicrob Chemother 18 Suppl A, 35-45 (1986).

Avci, Novel strategies for development of next-generation glycoconjugate vaccines. Curr Top Med Chem 13, 2535-2540 (2013).

Avci et al., How bacterial carbohydrates influence the adaptive immune system. Annu Rev Immunol 28, 107-130 (2010).

Avci et al., A mechanism for glycoconjugate vaccine activation of the adaptive immune system and its implications for vaccine design. Nat Med 17, 1602-1609 (2011).

Avery et al., The Specific Action of a Bacterial Enzyme on Pneumococci of Type Iii. Science 72, 151-152 (1930).

Avery et al., The Protective Action of a Specific Enzyme against Type Iii Pneumococcus Infection in Mice. J Exp Med 54, 73-89 (1931).

Aziz et al., The RAST Server: rapid annotations using subsystems technology. BMC Genomics 9, 75 (2008).

Baik et al., *Paenibacillus wooponensis* sp. nov., isolated from wetland freshwater. Int J Syst Evol Microbiol 61, 2763-2768 (2011).

Blakeney et al. A simple colorimetric method for the determination of sugars in fruit and vegetables. J. Sci. Food Agric. 31, 889-897, (1980).

Blanchette-Cain et al., *Streptococcus pneumoniae* biofilm formation is strain dependent, multifactorial, and associated with reduced invasiveness and immunoreactivity during colonization. mBio 4, e00745-00713 (2013).

Bogaert et al., *Streptococcus pneumoniae* colonisation: the key to pneumococcal disease. Lancet Infect Dis 4, 144-154 (2004).

Bonten et al., Polysaccharide conjugate vaccine against pneumococcal pneumonia in adults. N Engl J Med 372, 1114-1125 (2015).

Bouraoui et al., *Paenibacillus marinum* sp. nov., a thermophilic xylanolytic bacterium isolated from a marine hot spring in Tunisia. J Basic Microbiol 53, 877-883 (2013).

Bowie et al., Deciphering the message in protein sequences: tolerance to amino acid substitutions. Science 247, 1306-1310 (1990).

Briles et al., Strong association between capsular type and virulence for mice among human isolates of *Streptococcus pneumoniae*. Infect Immun 60, 111-116 (1992).

Briles et al., Antiphosphocholine antibodies found in normal mouse serum are protective against intravenous Infection with type 3 *Streptococcus pneumoniae*. J Exp Med 153, 694-705 (1981).

Brown et al., The role of antibody and complement in the reticuloendothelial clearance of pneumococci from the bloodstream. Rev Infect Dis 5 Suppl 4, S797-805 (1983).

Bruyn et al., Mechanisms of host defense against infection with *Streptococcus pneumoniae*. Clin Infect Dis 14, 251-262 (1992).

Burton et al., Development of a fourfold multiplexed opsonophagocytosis assay for pneumococcal antibodies against additional serotypes and discovery of serological subtypes in *Streptococcus pneumoniae* serotype 20. Clin Vaccine Immunol 19, 835-841 (2012).

Cartee et al., Mechanism of type 3 capsular polysaccharide synthesis in *Streptococcus pneumoniae*. J Biol Chem 275, 3907-3914 (2000).

Chiavolini et al., Animal models of *Streptococcus pneumoniae* disease. Clin Microbiol Rev 21, 666-685 (2008).

Chung et al., Degradation of polyvinyl alcohol in textile waste water by Microbacterium barkeri KCCM 10507 and Paenibacillus amylolyticus KCCM 10508. Environ Technol 37, 452-458 (2016).

Craig et al., Neutrophil recruitment to the lungs during bacterial pneumonia. Infect Immun 77, 568-575 (2009).

Dagan et al., Comparative immunogenicity and efficacy of 13-valent and 7-valent pneumococcal conjugate vaccines in reducing nasopharyngeal colonization: a randomized double-blind trial. Clin Infect Dis 57, 952-962 (2013).

Daniels et al., Modified opsonization, phagocytosis, and killing assays to measure potentially protective antibodies against pneumococcal surface protein A. Clin Vaccine Immunol 20, 1549-1558 (2013).

Dillard et al., Characterization of the cassette containing genes for type 3 capsular polysaccharide biosynthesis in *Streptococcus pneumoniae*. J Exp Med 181, 973-983 (1995).

Dillard et al., Genetic and molecular characterization of capsular polysaccharide biosynthesis in *Streptococcus pneumoniae* type 3. Mol Microbiol 12, 959-972 (1994).

Dubos et al., Decomposition of the Capsular Polysaccharide of Pneumococcus Type Iii by a Bacterial Enzyme. J Exp Med 54, 51-71 (1931).

Fenton et al., Recombinant bacteriophage lysins as antibacterials. Bioeng Bugs 1, 9-16 (2010).

Fiebig et al., An efficient cell free enzyme-based total synthesis of a meningococcal vaccine candidate. NPJ Vaccines 1, 16017 (2016).

Finn et al., InterPro in 2017-beyond protein family and domain annotations. Nucleic Acids Res 45, D190-D199 (2017).

Fischetti, Bacteriophage lytic enzymes: novel anti-infectives. Trends Microbiol 13, 491-496 (2005).

Fischetti, Bacteriophage endolysins: a novel anti-infective to control Gram-positive pathogens. Int J Med Microbiol 300, 357-362 (2010).

Fleck et al., Use of HL-60 cell line to measure opsonic capacity of pneumococcal antibodies. Clin Diagn Lab Immunol 12, 19-27 (2005).

Forsee et al., Role of the carbohydrate binding site of the *Streptococcus pneumoniae* capsular polysaccharide type 3 synthase in the transition from oligosaccharide to polysaccharide synthesis. J Biol Chem 281, 6283-6289 (2006).

Forsee et al., Characterization of the lipid linkage region and chain length of the cellubiuronic acid capsule of *Streptococcus pneumoniae*. J Biol Chem 284, 11826-11835 (2009).

Fuchs et al., Effect of aerosolized recombinant human DNase on exacerbations of respiratory symptoms and on pulmonary function in patients with cystic fibrosis. The Pulmozyme Study Group. N Engl J Med 331, 637-642 (1994).

Garcia-Quintanilla et al., Production of a recombinant vaccine candidate against Burkholderia pseudomallei exploiting the bacterial N-glycosylation machinery. Front Microbiol 5, 381 (2014).

Geno et al., Pneumococcal Capsules and Their Types: Past, Present, and Future. Clin Microbiol Rev 28, 871-899 (2015).

Goldblatt et al., Antibody responses to nasopharyngeal carriage of *Streptococcus pneumoniae* in adults: a longitudinal household study. J Infect Dis 192, 387-393 (2005).

Goujon et al., A new bioinformatics analysis tools framework at EMBL-EBI. Nucleic Acids Res 38, W695-699 (2010).

Grabenstein et al., A century of pneumococcal vaccination research in humans. Clin Microbiol Infect 18 Suppl 5, 15-24 (2012).

Grady et al., Current knowledge and perspectives of Paenibacillus: a review. Microb Cell Fact 15, 203 (2016).

Gruber et al., Development and clinical evaluation of Prevnar 13, a 13-valent pneumococococcal CRM197 conjugate vaccine. Ann N Y Acad Sci 1263, 15-26 (2012).

Guo et al., Isolation of a *Paenibacillus* sp. strain and structural elucidation of its broad spectrum lipopeptide antibiotic. Appl Environ Microbiol 78, 3156-3165 (2012).

Hammerschmidt et al., Illustration of pneumococcal polysaccharide capsule during adherence and invasion of epithelial cells. Infect Immun 73, 4653-4667 (2005).

Harboe et al., Impact of 13-valent pneumococcal conjugate vaccination in invasive pneumococcal disease incidence and mortality. Clin Infect Dis 59, 1066-1073 (2014).

Henrissat et al., Updating the sequence-based classification of glycosyl hydrolases. Biochem J 316 ( Pt 2), 695-696 (1996).

Hong et al., Biochemical characterization and antifungal activity of an endo-1,3-beta-glucanase of *Paenibacillus* sp. isolated from garden soil. Appl Microbiol Biotechnol 61, 472-478 (2003).

(56)            References Cited

OTHER PUBLICATIONS

Hyams et al., The *Streptococcus pneumoniae* capsule inhibits complement activity and neutrophil phagocytosis by multiple mechanisms. Infect Immun 78, 704-715 (2010).

Jackson et al., Randomized clinical trial of a single versus a double dose of 13-valent pneumococcal conjugate vaccine in adults 55 through 74years of age previously vaccinated with 23-valent pneumococcal polysaccharide vaccine. Vaccine 36, 606-614 (2018).

Jado et al., Phage lytic enzymes as therapy for antibiotic-resistant *Streptococcus pneumoniae* infection in a murine sepsis model. J Antimicrob Chemother 52, 967-973 (2003).

Jochems et al., The immunological mechanisms that control pneumococcal carriage. PLoS Pathog 13, e1006665 (2017).

Kieninger et al., Safety, tolerability, and immunologic noninferiority of a 13-valent pneumococcal conjugate vaccine compared to a 7-valent pneumococcal conjugate vaccine given with routine pediatric vaccinations in Germany. Vaccine 28, 4192-4203 (2010).

Kietzman et al., Dynamic capsule restructuring by the main pneumococcal autolysin LytA in response to the epithelium. Nat Commun 7, 10859 (2016).

Kim et al., Biological and Epidemiological Features of Antibiotic-Resistant *Streptococcus pneumoniae* in Pre- and Post-Conjugate Vaccine Eras: a United States Perspective. Clin Microbiol Rev 29, 525-552 (2016).

Kishore et al., *Paenibacillus glacialis* sp. nov., isolated from the Kafni glacier of the Himalayas, India. Int J Syst Evol Microbiol 60, 1909-1913 (2010).

Knolhoff et al., Identification and Structural Characterization of Naturally-Occurring Broad-Spectrum Cyclic Antibiotics Isolated from Paenibacillus. J Am Soc Mass Spectrom 26, 1768-1779 (2015).

Konishi et al., 2-(2'-Hydroxyphenyl)benzene sulfinate desulfinase from the thermophilic desulfurizing bacterium *Paenibacillus* sp. strain A11-2: purification and characterization. Appl Microbiol Biotechnol 62, 356-361 (2003).

Leao et al., First report of Paenibacillus cineris from a patient with cystic fibrosis. Diagn Microbiol Infect Dis 66, 101-103 (2010).

Li et al., Profiling pneumococcal type 3-derived oligosaccharides by high resolution liquid chromatography-tandem mass spectrometry. J Chromatogr A 1397, 43-51 (2015).

Li et al., *Paenibacillus nicotianae* sp. nov., isolated from a tobacco sample. Antonie Van Leeuwenhoek 106, 1199-1205 (2014).

Li et al., Penicillin-Binding Protein Transpeptidase Signatures for Tracking and Predicting beta-Lactam Resistance Levels in *Streptococcus pneumoniae*. mBio 7, (2016).

Lim et al., *Paenibacillus gansuensis* sp. nov., isolated from desert soil of Gansu Province in China. Int J Syst Evol Microbiol 56, 2131-2134 (2006).

Lim et al., Defining the regulated secreted proteome of rodent adipocytes upon the induction of insulin resistance. J Proteome Res 7, 1251-1263 (2008).

Loeffler et al., Rapid killing of *Streptococcus pneumoniae* with a bacteriophage cell wall hydrolase. Science 294, 2170-2172 (2001).

Lu et al., Interleukin-17A mediates acquired immunity to pneumococcal colonization. PLoS Pathog 4, e1000159 (2008).

Lucas et al., Carbohydrate moieties as vaccine candidates. Clin Infect Dis 41, 705-712 (2005).

MacLeod et al., Prevention of Pneumococcal Pneumonia by Immunization with Specific Capsular Polysaccharides. J Exp Med 82, 445-465 (1945).

Magee et al., Requirement for capsule in colonization by *Streptococcus pneumoniae*. Infect Immun 69, 3755-3761 (2001).

Martens et al., Serotype-specific mortality from invasive *Streptococcus pneumoniae* disease revisited. BMC Infect Dis 4, 21 (2004).

Mendes et al., Soil-borne microbiome: linking diversity to function. Microb Ecol 70, 255-265 (2015).

Metcalf et al., Strain features and distributions in pneumococci from children with invasive disease before and after 13-valent conjugate vaccine implementation in the USA. Clin Microbiol Infect 22, 60 e69-60 e29 (2016).

Middleton et al., Complete Genome Sequence of the Bacterium Bacillus circulans Jordan Strain 32352. Genome Announc 5, (2017).

Middleton et al., Enzymatic Hydrolysis of Pneumococcal Capsular Polysaccharide Renders the Bacterium Vulnerable to Host Defense. Infect Immun 86, (2018).

Middleton et al., T Cell-Mediated Humoral Immune Responses to Type 3 Capsular Polysaccharide of *Streptococcus pneumoniae*. J Immunol 199, 598-603 (2017).

Middleton et al., Identification and characterization of the *Streptococcus pneumoniae* type 3 capsule-specific glycoside hydrolase of *Paenibacillus* species 32352. Glycobiology 28, 90-99 (2018).

Mitchison, The carrier effect in the secondary response to hapten-protein conjugates. II. Cellular cooperation. Eur J Immunol 1, 18-27 (1971).

Mitchison, The carrier effect in the secondary response to hapten-protein conjugates. I. Measurement of the effect with transferred cells and objections to the local environment hypothesis. Eur J Immunol 1, 10-17 (1971).

Moberley et al., Vaccines for preventing pneumococcal infection in adults. Cochrane Database Syst Rev, CD000422 (2013).

Naegeli et al., Current Approaches to Engineering N-Linked Protein Glycosylation in Bacteria. Methods Mol Biol 1321, 3-16 (2015).

Nakamura, Taxonomy of Bacillus circulans Jordan 1890-base composition and reassociation of deoxyribonucleic acid. Int. J. System. Bacteriol. 33, 46-52, (1983).

Nelson et al., Capsule enhances pneumococcal colonization by limiting mucus-mediated clearance. Infect Immun 75, 83-90 (2007).

O'Brien et al., Potential impact of conjugate pneumococcal vaccines on pediatric pneumococcal diseases. Am J Epidemiol 159, 634-644 (2004).

Obolski et al., Vaccination can drive an increase in frequencies of antibiotic resistance among nonvaccine serotypes of *Streptococcus pneumoniae*. Proc Natl Acad Sci U S A 115, 3102-3107 (2018).

Oldrini et al., Combined Chemical Synthesis and Tailored Enzymatic Elongation Provide Fully Synthetic and Conjugation-Ready Neisseria meningitidis Serogroup X Vaccine Antigens. ACS Chem Biol 13, 984-994 (2018).

Oliveira et al., Correction: The First Paenibacillus larvae Bacteriophage Endolysin (PlyPI23) with High Potential to Control American Foulbrood. PLoS One 10, e0136331 (2015).

Oliveira et al., The First Paenibacillus larvae Bacteriophage Endolysin (PlyPI23) with High Potential to Control American Foulbrood. PLoS One 10, e0132095 (2015).

Pasari et al., Impact of Module-X2 and Carbohydrate Binding Module-3 on the catalytic activity of associated glycoside hydrolases towards plant biomass. Sci Rep 7, 3700 (2017).

Paschall et al., Therapeutic Activity of Type 3 *Streptococcus pneumoniae* Capsule Degrading Enzyme Pn3Pase. Pharm Res 37, 236 (2020).

Pastagia et al., Lysins: the arrival of pathogen-directed anti-infectives. J Med Microbiol 62, 1506-1516 (2013).

Petersen et al., SignalP 4.0: discriminating signal peptides from transmembrane regions. Nat Methods 8, 785-786 (2011).

Armstrong Z., et al., "Structure and Function of Bs164 ß-Mannosidase from Bacteroides Salyersiae the Founding Member of Glycoside Hydrolase Family GH164", Journal of Biological Chemistry, 2020, vol. 295, pp. 4316-4326.

Boraston A.B., et al., "Carbohydrate-Brinding Modules:Fine-Tuning Polysaccharide Recognition," Biochemical Journal, 2004, vol. 382, pp. 769-781, XP002496583.

Carrard G., et al., "Widely Different Off Rates of Two Closely Related Cellulose-Binding Domains from Trichoderma Reesei", European Journal of Biochemistry, 1999, vol. 262, pp. 637-643.

Coutinho J.B., et al., "The Nature of the Cellulose-Binding Domain Affects the Activities of a Bacterial Endoglucanase on Different Forms of Cellulose", 1993, vol. 113, pp. 211-217, DOI:10.1111/j.1574-6968.1993.tb06516.x, XP023970934.

Davies G., et al., "Structures and Mechanisms of Glycosyl Hydrolases," Structure, Sep. 15, 1995, vol. 3, pp. 853-859, DOI: 10.1016/S0969-2126(01)00220-9, XP004587916.

Gasteiger E., et al., "ExPASy: The proteomics Server for In-Depth Protein Knowledge and Analysis," Nucleic Acids Research, 2003, vol. 31, No. 13, pp. 3784-3788, DOI:10.1093/nar/gkg563, XP055595893.

(56)    References Cited

OTHER PUBLICATIONS

Henrissat B., et al., "Conserved Catalytic Machinery and the Prediction of a Common Fold for Several Families of Glycosyl Hydrolases," Proceedings of the National Academy of Sciences, USA, 1996, vol. 93, p. 5674.
Herve C., et al., "Carbohydrate-Binding Modules Promote the Enzymatic Deconstruction of Intact Plant Cell Walls by Targeting and Proximity Effects," Proceedings of the National Academy of Sciences, USA, 2010, vol. 107, pp. 15293-15298, doi:10.1073/pnas. 1005732107, XP055011486.
International Preliminary Report on Patentability for International Application No. PCT/US2021/041932, mailed Jan. 26, 2023, 8 Pages.
International Search Report and Written Opinion for International Application No. PCT/US2021/041932, mailed Oct. 12, 2021, 12 Pages.
Kelley L.A., et al., "The Phyre2 Web Portal for Protein Modeling, Prediction and Analysis," Nature Protocols, 2015, vol. 10, No. 6, pp. 845-858.
Klontz E.H., et al., et al., "Molecular Basis of Broad Spectrum N-Glycan Specificity and Processing of Therapeutic IgG Monoclonal Antibodies by Endoglycosidase S2," ACS Central Science, 2019, vol. 5, pp. 524-538.
Lombard V., et al., "The Carbohydrate-Active Enzymes Database (CAZy) in 2013," Nucleic Acids Research, 2014, vol. 42, pp. D490-D495, DOI: 10.1093/nar/gkt1178, XP055519748.
Malaker S.A., et al., "The Mucin-Selective Protease StcE Enables Molecular and Functional Analysis of Human Cancer-Associated Mucins," Proceedings of the National Academy of Sciences, USA, 2019, vol. 116, pp. 7278-7287.
Mitchell A.L., et al., "InterPro in 2019: Improving Coverage, Classification and Access to Protein Sequence Annotations," Nucleic Acids Research, 2019, vol. 47, pp. D351-D360, DOI:10.1093/nar/gky1100, XP055621187.
Moxon E.R., et al., "The Role of Bacterial Polysaccharide Capsules as Virulence Factors," Current Topics in Microbiology and Immunology, 1990, vol. 150, pp. 65-85.
Office Action for Canadian Application No. 3071713, dated Dec. 9, 2024, 6 pages.
Sambrook J., et al., "Molecular Cloning: A Laboratory Manual", Current Protocols, Cold Spring Harbor Laboratory Press: Cold Spring Harbor, 32 Pages, Nov. 1989, vol. 1, 2, 3.
Search report for Chinese Application No. 201880052952.4, dated Jun. 11, 2021, 3 pages.
Shoseyov O., et al., "Carbohydrate Binding Modules: Biochemical Properties and Novel Applications," Microbiology and Molecular Biology Review, 2006, vol. 70, No. 2, pp. 283-295, DOI:10.1128/MMBR.00028-05, XP002496582.
Volkov I.Y., et al., "Prospects for Practical Application of Substrate-Binding Modules of Glycosyl Hydrolases", Applied Biochemistry and Microbiology, vol. 40, No. 5, pp. 499-504, 2004, 8 Pages.
Wantuch P.L., et al., "Characterization of the ß-Glucuronidase Pn3pase as the Founding Member of Glycoside Hydrolase Family GH169", Glycobiology, 2021, vol. 31, No. 3, pp. 266-274.
Wantuch P.L., et al., "Invasive Pneumococcal Disease in Relation to Vaccine Type Serotypes," Human Vaccines & Immunotherapeutics, 2019, vol. 15, No. 4, pp. 874-875.
Price et al., Glycoengineered Outer Membrane Vesicles: A Novel Platform for Bacterial Vaccines. Sci Rep 6, 24931 (2016).
Puchta et al., Characterization of inflammatory responses during intranasal colonization with Streptococcus pneumoniae. J Vis Exp, e50490 (2014).
Rice et al., Studies of anti-pneumococcal serum; complement-fixing activity of fractionated rabbit serum. J Immunol 54, 267-274 (1946).
Richter et al., Pneumococcal serotypes before and after introduction of conjugate vaccines, United States, 1999-2011(1.). Emerg Infect Dis 19, 1074-1083 (2013).
Rio et al., Purification of RNA using TRIzol (TRI reagent). Cold Spring Harb Protoc 2010, pdb prot5439 (2010).

Romero-Steiner et al., Use of opsonophagocytosis for serological evaluation of pneumococcal vaccines. Clin Vaccine Immunol 13, 165-169 (2006).
Shaw et al., Production of specific pneumococcus carbohydrate-splitting enzymes in media to which the specific substrate was not added. J Immunol 64, 27-32 (1950).
Shida et al., Transfer of Bacillus alginolyticus, Bacillus chondroitinus, Bacillus curdlanolyticus, Bacillus glucanolyticus, Bacillus kobensis, and Bacillus thiaminolyticus to the genus Paenibacillus and emended description of the genus Paenibacillus. Int J Syst Bacteriol 47, 289-298 (1997).
Sickles et al., A Systematic Study of Microorganisms Which Decompose the Specific Carbohydrates of the Pneumococcus. J Bacteriol 28, 415-431 (1934).
Sievers et al., Fast, scalable generation of high-quality protein multiple sequence alignments using Clustal Omega. Mol Syst Biol 7, 539 (2011).
Simell et al., The fundamental link between pneumococcal carriage and disease. Expert Rev Vaccines 11, 841-855 (2012).
Song et al., Pneumococcal vaccine and opsonic pneumococcal antibody. J Infect Chemother 19, 412-425 (2013).
Sugimoto et al., Invasive pneumococcal disease caused by mucoid serotype 3 Streptococcus pneumoniae: a case report and literature review. BMC Res Notes 10, 21 (2017).
Tatusova et al., BLAST 2 Sequences, a new tool for comparing protein and nucleotide sequences. FEMS Microbiol Lett 174, 247-250 (1999).
Tin Tin Htar et al., Effectiveness of pneumococcal vaccines in preventing pneumonia in adults, a systematic review and meta-analyses of observational studies. PLoS One 12, e0177985 (2017).
Torriani et al., Inducible polysaccharide depolymerases of Bacillus palustris. J Biol Chem 237, 3-13 (1962).
Traxler et al., Natural products in soil microbe interactions and evolution. Nat Prod Rep 32, 956-970 (2015).
Uetanabaro et al., Paenibacillus agarexedens sp. nov., nom. rev., and Paenibacillus agaridevorans sp. nov. Int J Syst Evol Microbiol 53, 1051-1057 (2003).
UniProtKB—A0A0Q9N3M1 (A0A0Q9N3M1_9BACL), Protein: Uncharacterized protein, Gene ASL 11_17645, Organism Paenibacillus sp. Soil750, accessed via the world wide web uniprot.org/uniprot/A0A0Q9N3M1 on Nov. 26, 2018.
Valguarnera et al., Glycoengineered Outer Membrane Vesicles as a Platform for Vaccine Development. Methods Enzymol 597, 285-310 (2017).
Van Epps "Rene Dubos: unearthing antibiotics", vol. 203, No. 2, p. 259, Feb. 20, 2006.
Walhout et al., Gateway recombinational cloning: application to the cloning of large numbers of open reading frames or ORFeomes. Methods Enzymol 328, 575-592 (2000).
Wantuch et al., Current status and future directions of invasive pneumococcal diseases and prophylactic approaches to control them. Hum Vaccin Immunother 14, 2303-2309 (2018).
Watson et al., Interruption of capsule production in Streptococcus pneumonia serotype 3 by insertion of transposon Tn916. Infect Immun 58, 3135-3138 (1990).
Weinberger et al., Association of serotype with risk of death due to pneumococcal pneumonia: a meta-analysis. Clin Infect Dis 51, 692-699 (2010).
Winkelstein, The role of complement in the host's defense against Streptococcus pneumoniae. Rev Infect Dis 3, 289-298 (1981).
Winkelstein, Complement and the host's defense against the pneumococcus. Crit Rev Microbiol 11, 187-208 (1984).
Xie et al., Comparative genomic analysis of N2-fixing and non-N2-fixing Paenibacillus spp.: organization, evolution and expression of the nitrogen fixation genes. PLoS Genet 10, e1004231 (2014).
Yin et al., dbCAN: a web resource for automated carbohydrate-active enzyme annotation. Nucleic Acids Res 40, W445-451 (2012).
Zafar et al., Capsule Type and Amount Affect Shedding and Transmission of Streptococcus pneumoniae. mBio 8, (2017).
Zhang et al., Cellular effectors mediating Th17-dependent clearance of pneumococcal colonization in mice. J Clin Invest 119, 1899-1909 (2009).

(56) References Cited

OTHER PUBLICATIONS

Zhao et al., Serotype distribution and antibiotic resistance of *Streptococcus pneumoniae* isolates from 17 Chinese cities from 2011 to 2016. BMC Infect Dis 17, 804 (2017).

Middleton et al., "Enzymatic hydrolysis of pneumococcal type III polysaccharide", Glycobiology, p. 1440, (2016).

Bacillus circulans Jordan strain 32352 (ATCC 14175), product sheet, accessed Jul. 13, 2022 on the world wide web at atcc.org/products/14175.

Sadowski M.I., et al., "The Sequence-structure Relationship and Protein Function Prediction", Current Opinion in Structural Biology, vol. 19, No. 3, Jun. 2009, pp. 357-362, Published May 4, 2009, doi: 10.1016/j.sbi.2009.03.008.

Seffernick J.L., et al., "Melamine Deaminase and Atrazine Chlorohydrolase: 98 Percent Identical but Functionally Different", Journal of Bacteriology, Apr. 2001, vol. 183, No. 8, pp. 2405-2410.

Tang S., et al., "Identification of Dehalobacter Reductive Dehalogenases That Catalyse Dechlorination of Chloroform, 1,1,1-Trichloroethane and 1,1-dichloroethane", Philosophical Transactions of the Royal Society B Biological Sciences, vol. 368, No. 1616, Mar. 11, 2013, pp. 1-10. 20120318, doi: 10.1098/rstb.2012.0318, PMID: 23479748, PMCID: PMC3638459.

* cited by examiner

FIG. 1

-3) βDGlc*p*A (1-4) βDGlc*p* (1-

FIG. 2

```
WP_079915027.1   -----------------------------MAIGTSYRLRQALNRSCIALAASALLASAAASFT---   34
WP_113018908.1   MNNMISRKGWKQ------------------------AKRPFSALTAGMLAVSMALGLAPA       36
WP_068663733.1   -------------------------------MGLLKKHCAALTAAIMLTSAAVSLA--       25
KRE82476.1       -------------------------------~MGLLKKHYAALTAALMLTSAAVSFA--       25
WP_082593776.1   ---MVCCNRWLVRAERKQPLCCTGFIIDREVCRMGLLKKHYAALTAALMLTSAAVSFA--       55
WP_056617367.1   -------------------------------MGLFKKHCAALTAALMLSSVAISFA--       25
WP_028553222.1   -------------------------------MGLLRKHCAALTAALMLTSVAVSFA--       25
                                                    .:   **:*. :   * *  .::

WP_079915027.1   -----AGTTHAAPVNLEADYALSEGQLVRTEQFNNTNYTPLPVHVVDELKGIRTKVVRDF     89
WP_113018908.1   FPETAQAEVSPTAQVLTADYGTSAGPLIRTEQFNNTNYAPLPVHVVDELKGIKTKIVRDF     96
WP_068663733.1   -----PQAAQAASMNMEADYAVSEGPLVRTEQFNNTNYTPLPVHVVDELKGIKTKVVRDF     80
KRE82476.1       -----PQSVHAASVNMEADYAVSEGPLVRTEQFNNTNYTPLPVHVVDELKGIKTKVVRDF     80
WP_082593776.1   -----PQSVHAASVNMEADYAVSEGPLVRTEQFNNTNYTPLPVHVVDELKGIKTKVVRDF    110
WP_056617367.1   -----PQSVHAASVNMEADYAVSEGPLVRTEQFNNTNYTPLPVHVVDELKGIKTKVVRDF     80
WP_028553222.1   -----PQSVHAASVNMEADYAVSEGPLVRTEQFNNTNYTPLPVHVVDELKGIKTKVVRDF     80
                      .  :   : ***. * * *:**********:***********:**:****

WP_079915027.1   VKINWYYNKDEANSDYLAYSIDDPRN-ATNPDLQHGRKETYDFMSQFTDGILLSLAYSYG    148
WP_113018908.1   VKINWYYNKDPNNSDLLAYSIETPENLETNPDLQHGRKETYDFMGQFADSILISLAYSYG    156
WP_068663733.1   VKINWYYNKDSANSDYLAYSIDDARN-ATNPDLLSARKETYDFMSQFSDSLLISLAYSYG    139
KRE82476.1       VKINWYYNKDSANSDYLAYSIDDARN-ATNPDLLSARKETYDFMSQFSDSLLISLAYSYG    139
WP_082593776.1   VKINWYYNKDSANSDYLAYSIDDARN-ATNPDLLSARKETYDFMSQFSDSLLISLAYSYG    169
WP_056617367.1   VKINWYYNKDSANSDYLAYSIDDARN-ATNPDLLSARKETYDFMSQFSDSLLISLAYSYG    139
WP_028553222.1   VKINWYYNKDSTNSDYLAYSIDDARN-ANNPDLLSARKETYDFMSQFSDSLLISLAYSYG    139
                 *********  *** *****:  .* .****  .*******.**:*.:*:*******

WP_079915027.1   GDANPQKNRLLAGETEMNWPEFDKAMKKIIYTLKEKNPKIEYIEVGNEPNLEPAYYGHVK    208
WP_113018908.1   GDTNPGKNRLLSGETTMNWDEYDKAMRVIIKTLKEKNPKLEYIEVGNEPNLEPAYFGHVK    216
WP_068663733.1   GDANPEKNRLIAGETTMNWPEFDKAMKKIIFTLKEKNPELEYIEVGNEPNLEPAFYGHTK    199
KRE82476.1       GDANPEKNRLIAGETTMNWIEFDKAMKKIIYTLKEKNPELEYIEVGNEPNLEPAFYGHTK    199
WP_082593776.1   GDANPEKNRLIAGETTMNWIEFDKAMKKIIYTLKEKNPELEYIEVGNEPNLEPAFYGHTK    229
WP_056617367.1   GDANPEKNRLIAGETTMNWPEFDKAMKKIIYTLKEKNPELEYIEVGNEPNLEPAFYGHTK    199
WP_028553222.1   GDANPEKNRLIAGETTMNWPEFDKAMKKIIYTLKEKNPKLEYIEVGNEPNLEPAFYGHTK    199
                 **:** ****:*** *** *:****: ** *******:.************:.**.*

WP_079915027.1   DDIPGYMRMYQGMSEAVKWVNAQ-------GLAGQPLKVGGPVLSGYNFEKQKQFVDLAY    261
WP_113018908.1   DDIPGYMRMYEGMSKAVVWVNQQLGLNDTFGSNGVRLKVGGPVLSGYNFAKQKEFVDIAY    276
WP_068663733.1   EDIPGYMRMYQGMSEAVKWVNTQ-------GLAGQSVKVGGPVLSGYNFDKQKQFVDIAY    252
KRE82476.1       EDIPGYMRMYQGMSEAVKWVNTQ-------GLTGQSVKVGGPVLSGYNFDKQKQFVDIAY    252
WP_082593776.1   EDIPGYMRMYQGMSEAVKWVNTQ-------GLTGQSVKVGGPVLSGYNFDKQKQFVDIAY    282
WP_056617367.1   DDIPGYMRMYQGMSEAVKWVNTQ-------GLTGHSVKVGGPVLSGYNFDKQKQFVDIAY    252
WP_028553222.1   EDIPGYMRMYQGMSEAVKWVNTQ-------GLTGQSVKVGGPVLSGYNFDKQKQFVDIAY    252
                 :*********:***:** *** *        *  *  :***********.***:***:**

WP_079915027.1   AASYQVDFVSWHRYQEDVRMNETQEIEMKSYLHKFYPNAITIVSEYGWKGGGGLSDPTNN    321
WP_113018908.1   QNHYQVDFVSWHRYRQEITENETQAIQMRNYLSDKYPDATLIVSEYGWKGGGGLTDSTNN    336
WP_068663733.1   ANGYQVDFVSWHRYQEDVRMNETQEIEMKGYLHRFYPNATTIVSEYGWKGGGDLSDATNN    312
KRE82476.1       ANGYQVDFVSWHRYQEDVRMNETQEIQMKTYLHQFYPNATTIVSEYGWKGGGGLSDATNN    312
WP_082593776.1   ANGYQVDFVSWHRYQEDVRMNETQEIQMKTYLHQFYPNATTIVSEYGWKGGGGLSDATNN    342
WP_056617367.1   ANGYQVDFVSWHRYQEDVRMNETQEIQMKGYLHQFYPNATTIVSEYGWKGGGGLSDATNN    312
WP_028553222.1   ANGYQVDFVSWHRYQEDVRMNETQEIEMKGYLHRFYPNATTIVSEYGWKGGGGLSDATNN    312
                    *********::::  **** *:*: **   **:*  **********.*:* ***

WP_079915027.1   VGLAKQAAFMTDSASYYARGGTDIPMNWVAVHTLNAYFKNQFDVDYALSNGDTTNWQTFM    381
WP_113018908.1   VALAKQAAFMTDSAYFYERGGVDIPMNWVAVHTLNAYFKNQFDVDYALSNGT-VGWQEFN    395
WP_068663733.1   VGLAKQAAFMTDSAYFYARGGTDIPMNWVAVHTLNAYFKNQFDVDYALSTGDTTNWQSFT    372
KRE82476.1       VGLAKQAAFMTDSAYFYARGGTDIPMNWVAVHTLNAYFKNQFDVDYALSNGDTTNWQSFT    372
WP_082593776.1   VGLAKQAAFMTDSAYFYARGGTDIPMNWVAVHTLNAYFKNQFDVDYALSNGDTTNWQSFT    402
WP_056617367.1   VGLAKQAAFMTDSAYFYARGGTDIPMNWVAVHTLNAYFKNQFDVDYALSNGDTMNWQSFT    372
WP_028553222.1   VGLAKQAAFMTDSAYFYARGGTDIPMNWVAVHTLNAYFKNQFDVDYALSNGDTTNWQSFT    372
                 *.********** :* ***.*********************.*    .** *
```

FIG. 2 (Cont.)

```
WP_079915027.1    NPNPRALQYLNLRGWRESASTS-KPMKIKEIRFFDSSNNPIPIPNPANDPNIAAVTDGDD    440
WP_113018908.1    SNYTDPVRYMNLRGWRESATTSGRQVKIQEIEFYDPAGNKIAVPNTAGDPLIAVATDGDE    455
WP_068663733.1    NSDPRSLQYLNLRGWRESASTS-KPMKIKEIRFFDSNNNPIPIPNVLNDPSIAAVTDNDD    431
KRE82476.1        NSDPRSLQYLNLRGWRESASTS-KPMKIKEIRFFDSSNNPIQIPNVINDPSIAAVTDNDD    431
WP_082593776.1    NSDPRSLQYLNLRGWRESASTS-KPMKIKEIRFFDSSNNPIQIPNVINDPSIAAVTDNDD    461
WP_056617367.1    NSDPRSLQYLNLRGWRESASTS-KPMKIKEIRFFDSSNNLIPIPNALNDPSIAAVTDNDD    431
WP_028553222.1    NSDPRSLQYLNLRGWRESASTS-KPMKIKEIRFFDSSNNPIPIPNVLNDPSIAAVTDNDD    431
                  . ::*:**********:** : :**:**.*:*  .* * :** .** **..**.*:

WP_079915027.1    ATQFIQADYWTWLKFDLGPSAPGIARVDIKWGNPDINTFQLIGTSDKLKYYEALGRTFYT    500
WP_113018908.1    STQFLQSDYWTWLRFDLGAEY-QISKIRIKWGDSQVYKFQVVGTSDKLKYHELLGKTFFT    514
WP_068663733.1    ATQFTQSDYWTWLKFDLGTNAPAVARVDIKWGNTDINTFQLIGTSDKLKYYEVLGHTFFT    491
KRE82476.1        ATQFTQSDYWTWLKFDLGANAPAIARVDIKWGNTDINTFQLIGTSDKLKYYEVLGHTFFT    491
WP_082593776.1    ATQFTQSDYWTWLKFDLGANAPAIARVDIKWGNTDINTFQLIGTSDKLKYYEVLGHTFFT    521
WP_056617367.1    ATQFTQSDYWTWLKFDLGSNAPAIARVDIKWGNTDINTFQLIGTSDKLKYYEVLGHTFFT    491
WP_028553222.1    ATQFTQSDYWTWLKFDLGSNAPAIARVDIKWGNTDINTFQLIGTSDKLKYYEVLGHTFFT    491
                  :*** *:*****:****  . :::: ****: :: :**::******* :* **:**:*

WP_079915027.1    PYFNTMRMFARLGDTRVKATGGSSDIYGTRMLATKNSDSKATMMVWNKQGDGAASSNVSI    560
WP_113018908.1    PYFNTMRMLSRLGDEKVAVTGSDTGNTGVRLLATKNSDSKATMMVWNHQLDGKASKEVSV    574
WP_068663733.1    PYFNTMRMFAQLGDTRVKTSGGSMEIYGTRMLATKNSDTKATMMVWNKQGDGTASANVDI    551
KRE82476.1        PYFNTMRMLAQLGDMRVKATGGSTDIYGIRMLATKNSDTKATMMVWNKQGDGAASANVDI    551
WP_082593776.1    PYFNTMRMLAQLGDMRVKATGGSTDIYGIRMLATKNSDTKATMMVWNKQGDGAASANVDI    581
WP_056617367.1    PYFNTMRMFAQLGDTRVKASGGSTDIYGTRMLATKNNDTKATMMVWNKQGDGTASANVDI    551
WP_028553222.1    PYFNTMRMFAQLGDTRVKTSGGSTDIYGTRMLATKNSDTKATMMVWNKQGDGTASANVDI    551
                  ********::*** :* .:*..   * *:*****.*:*********:* ** ** :*.:

WP_079915027.1    DVKHLPPGFEGKSVRIKKYLVDETHSNYAYNKIDELQLFDETIANTADNLTINATLNRNA    620
WP_113018908.1    QVKNLPASFQGKSIRYKKYLVDATHSNYAYNKNDSLEVVGQGTMNITGTEIFNETLTPNA    634
WP_068663733.1    SVKNLPAGFQGKSVRYKKLLVDESHSNHAYNKRDDLQMVDEGIVNLTDTIVLSQTLEKNA    611
KRE82476.1        SVKNLPAGFQGKSVRYKKLLVDESHSNHAYNKIDDLQMVDEGIVNLTDTIVLSQTLEKNA    611
WP_082593776.1    SVKNLPAGFQGKSVRYKKLLVDESHSNHAYNKIDDLQMVDEGIVNLTDTIVLSQTLEKNA    641
WP_056617367.1    SVKNLPAGFQGKSVRYKKMLVDESHSNHAYNKIDDLQMVDEGIVNLTDTIVLSQTLEKNA    611
WP_028553222.1    SVKNLPAGFQGKSVRYKKMLVDESHSNHAYNKVDDLQMVDEGIVNLTGTIVLSQTLDKNA    611
                  .**:** .*:**:* ** *** :***:**** *.*::..:   * :.. :. ** **

WP_079915027.1    VMLIELEAVDPSIQNIVSAGKEVTSTTGMTNMPALVDGNSLTAAVAADSSYPQTIQMDLG    680
WP_113018908.1    VMLIELEAVDSSINNIVSAGKTAT--GDLQNLAALVDGDERTSAAAANNSYPQSVVIDLE    692
WP_068663733.1    VMLIELEAVDPSIKNIVSAGKAVTLSPGMTGGANLVDGYDTTAAVAATNTYPQTVTVDLG    671
KRE82476.1        VMLIELEAVDPSIKNIVSAGKTVTLSPGMTGGANLVDGHDTTAAVSATNTYPQTVTVDLG    671
WP_082593776.1    VMLIELEAVDPSIKNIVSAGKTVTLSPGMTGGANLVDGHDTTAAVSATNTYPQTVTVDLG    701
WP_056617367.1    VMLIELEAVDPSIKNIVSAGKTVTLSPGMTGGANLVDGYETTAAVAATNTYPQTVTVDLG    671
WP_028553222.1    VMLIELEAVDPSIKNIVSAGKTVTLSQGMTGGANLVDGYDTTAAMAANNTYPQTVTVDLS    671
                  ********** **:******* .*  .:.   **** .*:* :* .:***:: :**

WP_079915027.1    RPYELSGMQIDWTNSASRDFSYAIATSLDGTSYHTVADQ---TDPASAVPRGNSLDWFQT    737
WP_113018908.1    RNFTVSGAEIKWSNAELQSYHYSISTSTDGGSYSTVVDSTYG-----AWSKGSSLHWFPA    747
WP_068663733.1    KSYQLAGMGIDWTNSASRGYTYTIESSLDGTHFTLASDMTFSSNPTYVPPLGNSLAWFTG    731
KRE82476.1        KSYQLAGMGIDWTNSASRGYTFKIETSLDGVNFTLASDMTFSSNPAYVPPLGNSLAWFTG    731
WP_082593776.1    KSYQLAGMGIDWTNSASRGYTFKIETSLDGVNFTLASDMTFSSNPAYVPPLGNSLAWFTG    761
WP_056617367.1    KSYQLAGMGIDWTSSASRGYTYKIETSLDGVNFTLASDMTFSSNPAYVPPLGNSLAWFTG    731
WP_028553222.1    KPYQLAGMGIDWTSASRGYTYKIETSLDGINFTLASDKTFSSNPAYVPPLGNSLAWFTG    731
                  : : ::*  *.*: :  :.:  : * :* **   :  .*      . *.** **

WP_079915027.1    KARYVKLTVTRSTFDGPLSINDVKVFAEALYKNGFDTTEDKNAMAAWTTVGFGSKSTPWT    797
WP_113018908.1    TARYVKLTVTGSYTGQPLSIDDISIFADGLYKNSFETPEERD-LSAWKLRGYGNKYTAWD    806
WP_068663733.1    KARYVKLTVTGSTYDGPLSINEVKVFADGMYKNGFESVADRD-TSAWTMTGYSSVSTPWT    790
KRE82476.1        KARYVKLTVTGSTYDGPLSINEVKLFADGMYKNGFESVADRD-TSAWTMIGYSSASTPWT    790
WP_082593776.1    KARYVKLTVTGSTYDGPLSINEVKLFADGMYKNGFESVADRD-TSAWTMIGYSSASTPWT    820
WP_056617367.1    KARYVKLTVTGSTYDGPLSINEVKVFADGMYKNGFESVADRD-TSAWTMTGYSSASTPWT    790
WP_028553222.1    KARYVKLTVTGSTYDGPLSINEVKVFADGMYKNGFESAADRD-TSTWTMIGYSSASTPWT    790
                  .********* *   ****:::.:**:.:***.*::  :::  ::*.   *:.. * *

WP_079915027.1    TVTDSVYHNTFVQPMDLFSTTP-SFAIFGD-SLKDYGVEARVRTTD---SGNVQMGLIAR    852
WP_113018908.1    FGTDTVTGNTYAVPHETFGDTSDNFGFFGDNSWADYGIEARVKIDNPAHTGDVKMGVTAR    866
WP_068663733.1    FATDSVTNNTYAIPVSTYGTTP-SFAILGD-DMKDYGVEARVKVANSSYAGNVQMGLLAR    848
KRE82476.1        FATDSVTNNTYAIPENTYGTTP-SFAILGD-DLKDYGVEARVKVANSSYTGQVQMGLLAR    848
WP_082593776.1    FATDSVTNNTYAIPENTYGTTP-SFAILGE-DLKDYGVEARVKVANSSYTGQVQMGLLAR    878
WP_056617367.1    FATDSVTNNTYAIPVNTYGTTP-SFAILGD-DLKDYGVEARVKVTNSSYTGNVQMGLLAR    848
WP_028553222.1    FATDSVTNNTYAIPVNTYGTTP-SFALLGE-DLKDYGVEARVKVANSSYTGQVQMGLLAR    848
                  **:*  **:. * . :. *  .*.::**:  .  ***:****:  :  :*:*:**: **
```

FIG. 2 (Cont.)

```
WP_079915027.1    ATDYN-------NLYYFKLYRSSSAHQAVLEKRVN-----GTTTVLKSVDLADPIQSNRWYR    902
WP_113018908.1    AGKGRADEHRNLHYSLLLVRGAGTSKLVLQRDNTDMPSGKKNIELDSVVLDSIDPTRWYT    926
WP_068663733.1    ASTYN-------SHYYFKLMRTNTTNQAILEKRIN-----GTTTVLATVDLPAAIDSSKWYK    898
KRE82476.1        AGTYN-------NQYYFKLMRTSTTNQAILEKRIN-----GTTTVLATVDLPTAIDSSKWYK    898
WP_082593776.1    AGTYN-------NQYYFKLMRTSTTNQAILEKRIN-----GTTTVLATVDLPTAIDSSKWYK    928
WP_056617367.1    ASTYN-------SQYYFKLMRTSTTNQAILEKRIS-----GTTTVLATIDLSTPIDSSKWYK    898
WP_028553222.1    ASTYN-------SQYYFKLMRTSTANQAILEKRIS-----GTTTVLATVDLPTAIDSSKWYK    898
                  *    .       * : * *    : : :*::   .    *...:    :   *: .:**

WP_079915027.1    LNLEAVGTTLRASIDGVQVIELTDASRA---------SGKFGLRSHESIAGFDDVKVYPIV    954
WP_113018908.1    LRLEAVGDNLKGYLDGTLMVEYTDNNVYDGNPARLSAGWAGVRGSKTKVQFDDIHVYPIM    986
WP_068663733.1    LNLETIGTAIKGYVDGVLVFDTTDTSRT---------SGKFGLRSHDALASFDDVRVYPIV    950
KRE82476.1        LNLETIGTTLKGYVDGQLVIETTDTSRA---------SGKFGLRSHDALASFDDVRVYPIV    950
WP_082593776.1    LNLETIGTTLKGYVDGQLVIETTDTSRA---------SGKFGLRSHDALASFDDVRVYPIV    980
WP_056617367.1    LNLETIGTTIKGYVDGVLVIETTDTSRT---------SGKFGLRSHDALASFDDVRVYPIV    950
WP_028553222.1    LNLETIGTTLKGYVDGELVIETTDASRT---------SGKFGLRSHDALASFDDVRVYPIV    950
                  *.**::*   ::. :**   :.: **  .         :*  *:*. .: . ***:*****:

WP_079915027.1    PLLGDIKVNSVSIEGFHPHLNNYTVLVPST-SSAVTVTATVYGTANTVASPA-SGQVTFD    1012
WP_113018908.1    PLLGDIQVNGASISGFNPLKNEYEVKLAGPGSDKATVTGTVYGGANAVVYPASSGELALG    1046
WP_068663733.1    PLLGSIKVDGVIINGFDPRINSYTVLVPSS-TSTVTVTGSAYGTGSIAVLPA-SGQVTFD    1008
KRE82476.1        PMLGSIKVDGVTINGFDPKINSYTVLVPSS-TSTVTVTGSAYGTGSISVSPA-SGQVTFD    1008
WP_082593776.1    PMLGSIKVDGVTINGFDPKINSYTVLVPSS-TSTVTVTGSAYGTGSISVSPA-SGQVTFD    1038
WP_056617367.1    PLLGSIQVDGVTINGFDPKINSYTVLVPSS-TSTVTVTGSAYGTGSISVSPA-SGQVTFD    1008
WP_028553222.1    PLLGSIKVDGVAINGFDPKINSYTVLVPST-TSTVTVTGSAYGTGSIAVSPA-SGQVTFD    1008
                  *:**.*:*:... *.**.*  *.* * :   :. .***.:.** ..  . ** **::::.

WP_079915027.1    AVGQERSYTVAALSTEGNGANYYKINLRTASADTSLSNLRLSVITDALTAPGQQLPESIV    1072
WP_113018908.1    GTGENVVHMISSLSTAGNGATYYKVSLRKASEDATLSSLKLSVIPDSGAYNPNELAPGDI    1106
WP_068663733.1    AVGQEKTYMIAALSSEGNGANYLLRLKQASSDATLSSLRLSVVTDPLTSPGQKLPAMSI    1068
KRE82476.1        AVGQEKIYTMAALSSEGNGANYYSLRLKQASSDATLSSLRLSMVTDPLTAPGQKLPAMSI    1068
WP_082593776.1    AVGQEKIYTMAALSSEGNGANYYSLRLKQASSDATLSSLRLSMVTDPLTAPGQKLPAMSI    1098
WP_056617367.1    AVGQEKTYTIAALSSEGNGANYYSLRLKQASSDATLSSLRLSVVTDPLTSPGQKLPAMSI    1068
WP_028553222.1    AVGQEKTYMIAALSSEGNGANYYSFRLKQASPDATLSSLRLSVVTDPLTDPGQKLPAMSI    1068
                  ..*::   : :::**: ****.**  .  *: ** *::**.*:**:: *  :    ::*     :

WP_079915027.1    ALVPGQTEYTIHVPSRTAYVKVVEAIPTVSNVASVQITNATLVNGSGTATVKVTSEAGTT    1132
WP_113018908.1    LLIPGVYEYDVKIPSRTAYVSVKEALPTVSNLATAVAANTAIVNGQGTITVDVTAESGKI    1166
WP_068663733.1    ALIPGQMNYTIHVPSRTNYVKVVEAVPTASNVATAQISDGVMVNGTGTAKVTVTSEAGTT    1128
KRE82476.1        ALIPGQTNYSIHVPSRTNYVKVVEAVPTASNVATAQISDGVMVNGTGTAMVTVTSEAGTT    1128
WP_082593776.1    ALIPGQTNYSIHVPSRTNYVKVVEAVPTASNVATAQISDGVMVNGTGTAMVTVTSEAGTT    1158
WP_056617367.1    ALIPGQTEYTIHVPSRTNYVKVVEAVPTASNVSTAQISDGVMVNGTGTAKVTVTSEAGTT    1128
WP_028553222.1    ALIPRQTDYTIHVPSRTNYVKVVEAVPTASNVATAQISDAVMVNGTGIAKVTVTSEAGTS    1128
                  *:*   :*  :::****  **.* **:**.**::. :: .:*** *   * **:*:*.

WP_079915027.1    AEYMLNIRANPEAAAGTVLYEENFESGAYNQDAATGWNNGAVPNGAASHLRVADEDQGKV    1192
WP_113018908.1    QRYTLHLTANEEAPLGTILYEENFENGSYNQDASTGWRNMD--NTQGQHLRVADDVSGKV    1224
WP_068663733.1    SVYTLNLVANAEAPTGAVLYQENFDNGSYNSDPSFGWNNGATPNAASSHLRVVDEEQGKV    1188
KRE82476.1        MVYTLNLVANAAAPTGAVLYQEDFENGSYNSDLSVGWNNGATPNAASSHLRVVDEEQGKV    1188
WP_082593776.1    MVYTLNLVANAAAPTGAVLYQEDFENGSYNSDLSVGWNNGATPNAASSHLRVVDEEQGKV    1218
WP_056617367.1    TVYTLHLVANAEAPTGAVLYQENFENGSFNSDPSTGWNNGATPNGASSHLRVVDEDQGKV    1188
WP_028553222.1    TVYTLHLVANAEAPIGAVLYQEDFENGSYNVDPATGWNNGATPNGASSHLRVVDEDQGKV    1188
                  * *::  **  *  *:*:**:*:*:.:**:* * : **.*    * ..****.*: .***

WP_079915027.1    LEKYTTTSMAFTVGQSGWTDYDVRARVKAQASPSLPGIIARASDDAKNFYMLRIHNGTNG    1252
WP_113018908.1    LEKHTNDNMPFVVGNSSWTNYEVRARVRATADTGLPGIIARASDDARNFYMLRIHNGENN    1284
WP_068663733.1    LEKYTTTSMAFTVGQSAWTNYDVRARVKAQVGTALPGVIARASDDAKNFYMLRIHNGTNG    1248
KRE82476.1        LEKYTTTSTAFTVGQSAWTNYDVRARVKAQVGTSLPGVIARASDDAKNFYMLRIHNGTNG    1248
WP_082593776.1    LEKYTTTSTAFTVGQSAWTNYDVRARVKAQVGTSLPGVIARASDDAKNFYMLRIHNGTNG    1278
WP_056617367.1    VEKYTTTSMAFTVGQSAWTNYDVRARVKAQVGTSLPGVIARASDDAKNFYMLRIHNGTNG    1248
WP_028553222.1    LEKYTTTSMAFTVGQSAWKNYDVRARVKAQVGTSLPGVIARASDDAKNFYMLRIHNGTNG    1248
                  :**:*. .  *.**:*.*.:*:*****:*  .. .***:*******:********** *.
```

FIG. 2 (Cont.)

```
WP_079915027.1    LPGGSTGYVILGRVVNGTLRELDSKKIPYPYVVGNWYQLRLVVDSNRIKGYVDDSLIYDE    1312
WP_113018908.1    LAGGSTGYIALGRVVNNSLKESAI-KKPFPYEEGKWYQLRLIVNGNRLIGYVDDKLVFDV    1343
WP_068663733.1    LAGGSTGYVALGRMVNSSLKELDSKKIPYPYIVGNWYQLRLVVEGNHLKGYVDDNLIFDE    1308
KRE82476.1        LAGGSTGYVALGRMVNGSLKELDSKKIPYPYIAGNWYQLRLVVDGDHIKGYVDDNLIFDE    1308
WP_082593776.1    LAGGSTGYVALGRMVNGSLKELDSKKIPYPYIAGNWYQLRLVVDGDHIKGYVDDNLIFDE    1338
WP_056617367.1    LAGGSTGYVSLGRMVNGSLKELDSKKIPYPYIVGNWYQLRLVVDGSHLKGYVDDNLIFDE    1308
WP_028553222.1    LAGGSTGYVALGRMVNGSLKELDSKKIPYPYIVGNWYQLRLVVDGNHLKGYVDDNLIFDE    1308
                  * ******: ***:**.:*:*    * *:** *:*****:*:..::  ****.*::*

WP_079915027.1    VDNG-SLFPTNPPALMQGKAGIRVANQAARIDDFQVSHLAAL---PADSVKPVITLNGPA    1368
WP_113018908.1    TDTGSGLFPDNPPPLTQGKAGIRVANRPAQIDDYVVALLPGDNTPVPDVVKPVITLNGDG    1403
WP_068663733.1    IDNG-ALFSSNPPTLIQGKAGIRVANQAARIDDFLVTELTDD---V---------------    1350
KRE82476.1        IDNG-ALFSSNPPPLTQGKAGIRVANQAARIDDFLVTELTDD---V---------------    1350
WP_082593776.1    IDNG-ALFSSNPPPLTQGKAGIRVANQAARIDDFLVTELTDD---V---------------    1380
WP_056617367.1    IDNG-ALFSVNPPALTQGKAGIRVANQAARIDDFLVTELTDD---V---------------    1350
WP_028553222.1    IDNG-SLFSSNPPALTQGKAGIRVANQAARIDDFVVTELTDD---V---------------    1350
                  *.* .** *** * *********: *;****: *: *

WP_079915027.1    VVEVLAGSTYTDAGATAADDVDGDLTSRIQVSGSVDTSTPGTYTLVYTVMDNAHNVADPV    1428
WP_113018908.1    AISIPVGSEYTDAGATATDNVDGDLTAAIAVTGQVNTAVPGVYTLRYNVSDAAGNAANEV    1463
WP_068663733.1    ------------------------------------------------------------    1350
KRE82476.1        ------------------------------------------------------------    1350
WP_082593776.1    ------------------------------------------------------------    1380
WP_056617367.1    ------------------------------------------------------------    1350
WP_028553222.1    ------------------------------------------------------------    1350

WP_079915027.1    VRTVTVTAAGDKPFTVIANGG-LNRTNGLSAKVDVTRTPGSVDHAGREVVYFQLLKGSTP    1487
WP_113018908.1    IRTVTVFAVIGEGKSFVVTGGLVDQAQGLTARVNVIPVAGAQVHDGDEVVYFQLLKGNTP    1523
WP_068663733.1    -----VVVPPVETLLPFTLEGQ-LNRSNGLNASVLVNRAANAADHPGTEVVFFQLLQGTTP    1405
KRE82476.1        -----VVVPPVDTPLPFSIEGQ-LNRSHGLHASVLVNRTAGAPDHSGTEVVFFQLLKGTTP    1405
WP_082593776.1    -----VVVPPVDTPLPFSIEGQ-LNRSHGLHASVLVNRTAGAPDHSGTEVVFFQLLKGTTP    1435
WP_056617367.1    -----VVVPPVETPVPFSIEGQ-LNRSNGLSASVLVSRTPNATDHAGTEVVFFQLLKGTTP    1405
WP_028553222.1    -----VVVPPVDTPVPFSIQGQ-LNRSNGLSASVLVSHTANAVDHPGTEVVFFQLLKGTTP    1405
                       .*      .  *   ::::::** * * *   . .:  * * ***:****:*.**

WP_079915027.1    VSHVALESELTNGGSLTGHFDVPDAEEGTYTVHVFIIDMLDSIEGSLPIPLSNKVIVE    1545
WP_113018908.1    VSYVALKSDITDLTTFVAHFDVPDPENTAYSIRVLVVDQLFPANGELPAALSDKVVLD    1581
WP_068663733.1    VSYVAMESEIGAGNRVAGHFDVPDPENMSYHVHAFVVSSWDLLNESLPLSLSNKLDLE    1463
KRE82476.1        VAYVAMESEIGAGNRVVGHFDVADPENLGYHVHAFVVGSWDLLNESMPLSLSNKLDIE    1463
WP_082593776.1    VAYVAMESEIGAGNRVVGHFDVADPENLGYHVHAFVVGSWDLLNESMPLSLSNKLDIE    1493
WP_056617367.1    VSYVAMENDIGTGNRVVGHFDVADPDNLSYHVHAFVVSSWDLLNESLPVSLSNKLDMK    1463
WP_028553222.1    VSYVAIEGEMGSGNRIVGHFDVADPENESYHVHAFVVSSLDLLNESLPIALSNKLDLE    1463
                  *::**::.::     ...**** * ::  * ::.:::.     : .:* **:*: :.
```

FIG. 4A

```
Pbac_3551    ref seq >WP_079915027.1 hypothetical protein
    1 maigtsyrlr qalnrscial aasallasaa asftagttha apvnleadya lsegqlvrte
   61 qfnntnytpl pvhvvdelkg irtkvvrdfv kinwyynkde ansdylaysi ddprnatnpd
  121 lqhgrketyd fmsqftdgil lslaysyggd anpqknrlla getemnwpef dkamkkiiyt
  181 lkeknpkiey ievgnepnle payyghvkdd ipgymrmyqg mseavkwvna qglagqplkv
  241 ggpvlsgynf ekqkqfvdla yaasyqvdfv swhryqedvr mnetqeiemk sylhkfypna
  301 itivseygwk gggglsdptn nvglakqaaf mtdsasyyar ggtdipmnwv avhtlnayfk
  361 nqfdvdyals ngdttnwqtf mnpnpralqy lnlrgwresa atskpmkike irffdssnnp
  421 ipipnpandp niaavtdgdd atqfiqadyw twlkfdlgps apgiarvdik wgnpdintfq
  481 ligtsdklky yealgrtfyt pyfntmrmfa rlgdtrvkat ggssdiygtr mlatknsdsk
  541 atmmvwnkqg dgaasenvsi dvkhlppgfe gksvrikkyl vdethsnyay nkidelqlfd
  601 etiantadnl tinatlnrna vmlieleavd psiqnivsag kevtsttgmt nmpalvdgns
  661 ltaavaadss ypqtiqmdlg rpyelsgmqi dwtnsaardf syaiatsldg tsyhtvadqt
  721 dpasavprgn sldwfqtkar yvkltvtrst fdgplsindv kvfaealykn gfdttedkna
  781 maawttvgfg skstpwttvt dsvyhntfvq pmdlfsttps faifgdslkd ygvearvrtt
  841 dsgnvqmgli aratdynnly yfklyrassa hqavlekrvn gtttvlksvd ladpiqsnrw
  901 yrlnleavgt tlrasidgvq vieltdasra sgkfglrshe siagfddvkv ypivpllgdi
  961 kvnsvsiegf hphlnnytvl vpstssavtv tatvygtant vaspasgqvt fdavgqersy
 1021 tvaalstegn ganyykinlr tasadtslsn lrlsvitdal tapgqqlpes ivalvpgqte
 1081 ytihvpsrta yvkvveaipt venvaavqit natlvngsgt atvkvtseag ttaeymlnir
 1141 anpeaaagtv lyeenfesga ynqdaatgwn ngavpngaas hlrvadedqg kvlekyttts
 1201 maftvgqsgw tdydvrarvk aqaspslpgi iarasddakn fymlrihngt nglpggstgy
 1261 vilgrvvngt lreldskkip ypyvvgnwyq lrlvvdsnri kqyvddsliy devdngalfp
 1321 tnppalmqgk agirvanqaa riddfqvshl aalpadsvkp vitlngpavv evlagstytd
 1381 agataaddvd gdltsriqvs gsvdtstpgt ytlvytvmdn ahnvadpvvr tvtvtasgdk
 1441 pftvianggl nrtnglsakv dvtrtpgsvd hagrevvyfq llkgstpvsh valeseltng
 1501 gsltghfdvp daoegtytvh vfiidmldsi egslpiplsn kvive
```

FIG. 4E

SEQ ID NO:1

```
atggctattggaacatcatataggctgcgtcaggcattgaaccgatcctgtatcgcgcttgcggccagtgccttgct
ggcatcggctgcagcaagcttcaccgcaggaacgactcatgcggcaccgtgaatctggaagcggattatgccttaa
gtgaagggcagcttgtccgcacggagcaattcaacaatacgaattacacgccgcttccggttcatgtcgtcgatgaa
ctcaaagggatccggaccaaggtcgtaagagattttgttaaaattaattggtactacaacaaggatgaggcgaacag
cgattatttggcttattccatcgacgacccgcgtaacgcgacgaacccggatttacagcatggccgcaaggaaacgt
atgatttcatgtcccagtttaccgatggcattctcctatctctcgcttattcctatggaggtgacgcgaatccgcag
aaaaaccgcctcctagccggcgagaccgaaatgaactggcctgaattcgacaaggcgatgaagaaaatcatttatac
gttgaaggagaaaaatccgaagatcgaatatatcgaggtgggcaacgagccgaacctggagcctgcctattatggac
atgtgaaggatgatattcccggctacatgcgcatgtatcagggcatgtcggaagcggtaaaatgggtaaacgcacag
ggcttggccgggcagccgctgaaagtaggcggaccggtattatccggctacaatttcgagaagcagaagcagttcgt
cgatcttgcctacgccgcaagctatcaggtcgattttgtgtcatggcaccgataccaggaggacgtgcggatgaacg
aaacgcaggaaatcgaaatgaaaagctatctgcacaagttttatccgaatgctataaccattgttagcgaatacggc
tggaagggggcgggggcttaagtgatccgacgaacaacgtcggactggcgaagcaagcggcgtttatgacggactc
ggcatcctattatgcccgtggagggacggatattccgatgaactgggtagcggtccatacactgaatgcgtatttca
agaaccagttcgatgtcgactatgctttaagcaatggggatacgacgaattggcagacatttatgaatcctaatcca
agggctttacaatatttgaacctgcgcgggtggagggagtcggcatcgacctccaagccgatgaagatcaaggaaat
tcgttttttgacagcagtaacaacccgattccaatcccgaatccggcaaacgacccgaatattgcggcggttacgg
acggtgacgatgcgacgcagtttatccaagcagactactggacctggctcaagtttgatctggggccatcggctccc
gggattgccagggttgatatcaagtgggggaatcccgatatcaacaccttccagctcattggcactagtgataaatt
gaaatattacgaggcgctgggccgcacttttctacaccccgtattttaacacaatgcggatgttcgcccggctcgggg
acacccgggtgaaagcaaccggcggcagcagtgacatctatgggacacggatgctggcgacgaagaacagcgattcc
aaagcgacgatgatggtgtggaacaaacagggagacggggcggcctcatccaatgtcagcatcgatgtgaagcatct
gccgccaggctttgaagggaagagtgtacggatcaaaaagtatttggtcgacgagacccatagcaattatgcctaca
acaaatcgacgagctccagttgttcgacgaaaccatagcgaacacggcggacaatctgacgattaacgctacgttg
aatagaaatgcggtaatgctgatagagctggaggcggttgatcctagcatccaaaatatcgtgtctgccggcaagga
agttacctctacgacaggaatgacgaatatgccggcgctggtggacggcaatagtctgactgctgctgtcgcagccg
atagcagctatccgcaaactatacaaatggatctcggcagaccctatgagttatcagggatgcaaatcgattggacg
aacagcgcatcgagagatttcagctacgcaatagcgacgagcttggatggcacgtcgtaccatacggtagcggatca
aaccgacccggcttccgcagtcccaagagggaacagtttggactggttccaaaccaaggcgcggtatgtgaagctga
cggtgacgcgctccaccttcgatggcccgctatcgattaacgatgtaaaggtttttgccgaagcgctgtacaaaaac
gggttcgacaccaccgaggataagaatgcgatggcggcatggacgacggttggctttggatcgaaatccaccccatg
gaccaccgtgacggacagtgtttaccataacacattcgtgcaaccgatggacctattcagcacgacacctagcttcg
ccattttggtgacagtcttaaggattatggagtggaagcgcgggtcagaactacggacagtggaaacgtgcaaatg
gggcttattgcccgagcgaccgattacaataacttgtattacttcaagctgtaccgaagcagctccgcgcatcaggc
agtgctggagaagcgcgtcaatggaacgacaaccgtgcttaagtcggtggatttggctgatccgattcagtcgaacc
gctggtataggctgaatttggaagctgtcggaacaacgctgcgagcttctattgacggtgttcaggttatcgagctt
acggatgccagccgggcttccggtaaattcgggctgcgaagccatgaatccatcgccggcttcgacgatgtcaaagt
gtatccgattgttccgctgcttggcgatattaaggtgaacagcgtatctattgagggcttccatccgcatttgaaca
actacactgtacttgtcccatcgacgagctctgcagtaaccgtgacggcaaccgtctacggtacggccaataccgtg
gcgtccccggcctccgggcaggtgaccttcgacgcggttggccaagagaggtcgtacacagtagctgcgctgtcgac
tgaaggcaatggggcgaattattacaagataaacttgcggacggcaagcgccgatacatcgcttagcaacctgaggc
tgtcggtcattacggacgctctgacagccccgggccaacaattacccgaatcgatcgttgctctggttccgggtcaa
acggaatacacgattcacgttccttcccgtacggcttatgtcaaggtggtagaggcgatcccgacggtaagcaatgt
ggcttcagttcaaatcactaacgcaactttggtgaacggctcgggtaccgcaacggtaaaagtaacctccgaagccg
gaacgacggcggaatatatgctgaatatccgggcgaacccggaggcggctgccgggacggtgctgtacgaagaaat
tttgagagcggagcttacaatcaagacgcagcgaccggttggaataacggtgccgtaccgaatggtgcagcttcaca
tctacgcgttgcggatgaggatcagggcaaggtgctggagaagtatgacgaccagcatggcctttacggtcggtc
aaagcggttggacagattacgatgtaaagggccagagttaaagcgcaggccagcccgtcactgccaggcattattgcg
cgcgcatccgacgatgccaaaaactttttatatgctgcgcattcataacggcacgaatggactgcctggcggaagcac
ggggtatgtcattcttggccgtgtcgtgaacgggacgctccgcgagctggacagcaaaaaaatcccatacccgtatg
tggtcggtaactggtatcagcttcgtcttgtcgtggatagtaatcggatcaaaggctatgtggacgatagcctgatc
tatgacgaagtagataacggatcgttattcccgacgaatcctcctgcactgatgcaaggcaaggcggggatccgggt
ggcaaaccaggcagcccgcatcgatgattttcaggtatcccatcttgctgccctacccgcagattcggtgaagccgg
tgataaccctgaacgggccggcagtggttgaagtattggctggcagcacgtatacggatgcaggagcgacggcggcg
```

FIG. 4E (Cont.)

```
gatgatgtggacggcgatctgacaagccgcattcaagtgagcggcagtgtggacacgtcgacgccaggaacgtacac
gctggtctataccgtaatggacaacgcacataatgtagcggacccggttgtacgcactgtaacggtaaccgctgcgg
gggataagccgtttactgtcattgcaaatggcgggctgaaccggacgaacggtttgagtgctaaggtcgacgttacc
cgcacacccggctcggtagatcatgcgggtagggaagtcgtttactttcagcttcttaagggcagcactcccgtatc
ccatgttgcgttggaaagcgagcttacgaatggcggcagcctgacaggccatttcgatgtgccggatgctgaagagg
gcacttatacggttcatgtgtttatcatcgatatgctcgactctatagagggatccttgccgattccgttatcgaat
aaggtgatcgtggagtag
```

PROTEINS HAVING PNEUMOCOCCAL CAPSULE DEGRADING ACTIVITY AND METHODS OF USE

CROSS-REFERENCE TO RELATED APPLICATIONS

This application is a continuation application of U.S. patent application Ser. No. 16/636,503, filed Feb. 2, 2020, now issued U.S. Pat. No. 11,690,900, which is the § 371 U.S. National Stage of International Application No. PCT/US2018/046521, filed Aug. 13, 2018, which claims the benefit of U.S. Provisional Application Ser. No. 62/545,094, filed Aug. 14, 2017, and U.S. Provisional Application Ser. No. 62/652,046, filed Apr. 3, 2018, the disclosures of which are incorporated by reference herein in their entireties.

GOVERNMENT FUNDING

This invention was made with government support under 1R01AI123383-01A1, awarded by the National Institutes of Health. The government has certain rights in the invention.

SEQUENCE LISTING

This application contains a Sequence Listing electronically submitted via Patent Center to the United States Patent and Trademark Office as an XML file entitled "0235-000271US02.xml" having a size of 44 kilobytes and created on May 17, 2023. The information contained in the Sequence Listing is incorporated by reference herein.

BACKGROUND

Diseases caused by *Streptococcus pneumoniae* (Spn) have long been a major threat to human health with alarming mortality rates. One disease, pneumonia, affects approximately 450 million people globally (7% of the population) and results in about 4 million deaths per year. Prevention of pneumococcal disease relies today on vaccination of the susceptible population. Pneumococcal vaccines are made empirically and are variably/poorly immunogenic especially among young children, the elderly, and immunocompromised individuals. The mainstay of drug therapy for pneumococcal disease is antibiotic treatment; however, widespread use of antibiotics against *S. pneumoniae* has led to spread of drug resistance pneumococcal strains. In 2015, according to CDC, pneumococcal bacteria were resistant to one or more antibiotics in 30% of the cases.

*S. pneumoniae* has over 90 unique capsular serotypes, each differing in monosaccharide composition and linkage, as well as other modifications such as acetylation. While conjugate vaccines have been effective for preventing carriage and disease caused by most *S. pneumoniae* serotypes included in the vaccines, the exception has been serotype 3.

SUMMARY

Described herein is the identification and cloning of a Pn3Pase gene expressed by a *Paenibacillus* strain. The Pn3Pase enzyme degrades the capsular polysaccharide of the *S. pneumoniae* serotype 3, which is among the most virulent serotypes with high morbidity and mortality rates. Capsular polysaccharide is the major virulence factor of *S. pneumoniae* (Spn), and most unencapsulated bacteria are not infective. The enzyme successfully degrades the capsular polysaccharide on the surface of the live bacterium. Moreover, the bacterium is susceptible to phagocytosis in the presence of the enzyme.

Provided herein is a genetically modified cell that includes a mature Pn3Pase protein. In one embodiment, the genetically modified cell includes a polynucleotide including a coding region, where the coding region includes a nucleotide sequence encoding a mature Pn3Pase protein. The protein can include an amino acid sequence having at least 80% identity with an amino acid sequence selected from SEQ ID NO:2, where the amino terminal amino acid is selected from any one of residues 2 to 64 of SEQ ID NO:2 and the carboxy terminal amino acid is residue 1545 of SEQ ID NO:2. In one embodiment, the protein includes an amino acid sequence having at least 80% identity with amino acids 41-1545 of SEQ ID NO:2. In one embodiment, the genetically modified cell can be a eukaryotic cell, such as a mammalian cell, a yeast cell, or an insect cell. In one embodiment, the genetically modified cell can be a prokaryotic cell, such as *E. coli*. In one embodiment, the protein includes a heterologous amino acid sequence, such as a tag.

Also provided herein are compositions. In one embodiment, a composition includes the genetically modified cell. In one embodiment, a composition includes an isolated, optionally purified, mature P3nPase protein. In one embodiment, a composition includes an isolated polynucleotide, where the polynucleotide includes a coding region encoding a mature Pn3Pase protein. The mature P3nPase protein can include an amino acid sequence having at least 80% identity with an amino acid sequence selected from SEQ ID NO:2, where the amino terminal amino acid is selected from residues 2 to 64 of SEQ ID NO:2 and the carboxy terminal amino acid is residue 1545 of SEQ ID NO:2. In one embodiment, the protein includes an amino acid sequence having at least 80% identity with amino acids 41-1545 of SEQ ID NO:2. In one embodiment, a composition further includes a pharmaceutically acceptable carrier.

Also provided herein are methods. In one embodiment, a method includes incubating a cell under conditions suitable for expression of a protein having Pn3Pase activity. The cell can include a polynucleotide including a coding region, where the coding region includes a nucleotide sequence encoding a mature Pn3Pase protein, where the protein has Pn3Pase activity, and where the cell expresses the mature Pn3Pase protein under suitable conditions. The protein can include an amino acid sequence having at least 80% identity with an amino acid sequence selected from SEQ ID NO:2, where the amino terminal amino acid is selected from any one of residues 2 to 64 of SEQ ID NO:2 and the carboxy terminal amino acid is residue 1545 of SEQ ID NO:2. In one embodiment, the protein includes an amino acid sequence having at least 80% identity with amino acids 41-1545 of SEQ ID NO:2. The cell can be a wild-type cell, e.g., a *Paenibacillus* strain, such as *Paenibacillus* sp. 32352, or a genetically modified cell where the polynucleotide encoding the is an exogenous polynucleotide. The method can further include isolating or purifying the protein. In one embodiment, the cell can be a eukaryotic cell, such as a mammalian cell, a yeast cell, or an insect cell. In one embodiment, the genetically modified cell can be a prokaryotic cell, such as *E. coli*. In one embodiment, the protein includes a heterologous amino acid sequence, such as a tag.

In one embodiment, a method includes contacting a *Streptococcus pneumoniae* including a type III capsular polysaccharide with a mature Pn3Pase protein, where the contacting is under conditions suitable for enzymatic hydrolysis of type III capsular polysaccharide, where the amount of type III capsular polysaccharide on the surface of the *S. pneumoniae* is reduced compared to the *S. pneumoniae* that is not contacted with the Pn3Pase protein. In another embodiment, a method is for increasing deposition of at least one complement component on the surface of a *Streptococcus pneumoniae*. In one embodiment, the method can include contacting a *Streptococcus pneumoniae* including a type III capsular polysaccharide with a mature Pn3Pase protein, where the deposition of at least one complement component on the surface of the *S. pneumoniae* is increased compared to the *S. pneumoniae* that is not contacted with the Pn3Pase protein. The protein can include an amino acid sequence having at least 80% identity with an amino acid sequence selected from SEQ ID NO:2, where the amino terminal amino acid is selected from any one of residues 2 to 64 of SEQ ID NO:2 and the carboxy terminal amino acid is residue 1545 of SEQ ID NO:2. In one embodiment, The protein includes an amino acid sequence having at least 80% identity with amino acids 41-1545 of SEQ ID NO:2. In one embodiment, the *S. pneumoniae* is present in conditions suitable for replication of the *S. pneumoniae*. In one embodiment, the mature Pn3Pase protein is an isolated Pn3Pase protein. In one embodiment, the contacting includes exposing the *S. pneumoniae* to a genetically modified cell that expresses the mature Pn3Pase protein. In one embodiment, the *S. pneumoniae* has increased susceptibility to phagocytosis by macrophages, increased complement-mediated killing by neutrophils, or a combination thereof, compared to the *S. pneumoniae* that is not contacted with the Pn3Pase protein. In one embodiment, the *S. pneumoniae* is present in a subject.

In one embodiment, a method is for treating an infection in a subject and includes administering an effective amount of a composition that includes a mature Pn3Pase protein having Pn3Pase activity to a subject having or at risk of having an infection caused by a serotype 3 *S. pneumoniae*. In one embodiment, the method is for treating a symptom in a subject and includes administering an effective amount of a composition including a mature Pn3Pase protein having Pn3Pase activity to a subject having or at risk of having an infection caused by a serotype 3 *S. pneumoniae*. In one embodiment, a method is for decreasing colonization in a subject and includes administering an effective amount of a composition including a including a mature Pn3Pase protein having P3nPase activity to a subject colonized by or at risk of being colonized by a serotype 3 *S. pneumoniae*. The protein can include an amino acid sequence having at least 80% identity with an amino acid sequence selected from SEQ ID NO:2, where the amino terminal amino acid is selected from any one of residues 2 to 64 of SEQ ID NO:2 and the carboxy terminal amino acid is residue 1545 of SEQ ID NO:2. In one embodiment, the protein includes an amino acid sequence having at least 80% identity with amino acids 41-1545 of SEQ ID NO:2. In one embodiment, the subject is a human.

Also provided is a mature Pn3Pase protein disclosed herein for use in therapy, mature Pn3Pase protein disclosed herein for use as a medicament, and a mature Pn3Pase protein disclosed herein for use in the treatment of a condition.

Further provided is the use of a mature Pn3Pase protein disclosed herein for preparation of a medicament for the treatment of pneumonia, pneumococcal meningitis, otitis media, bacteremia, sepsis, or a combination thereof; a composition including a mature P3nPase protein described herein for use in treating or preventing an infection or a symptom caused by a serotype 3 *S. pneumoniae*; and a protein, composition, or method including one or more features described herein.

As used herein, "genetically modified cell" refers to a cell into which has been introduced an exogenous polynucleotide, such as an expression vector. For example, a cell is a genetically modified cell by virtue of introduction into a suitable cell of an exogenous polynucleotide that is foreign to the cell. "Genetically modified cell" also refers to a cell that has been genetically manipulated such that endogenous nucleotides have been altered. For example, a cell is a genetically modified cell by virtue of introduction into a suitable cell of an alteration of endogenous nucleotides. An example of a genetically modified cell is one having an altered regulatory sequence, such as a promoter, to result in increased or decreased expression of an operably linked endogenous coding region.

As used herein, the term "protein" refers broadly to a polymer of two or more amino acids joined together by peptide bonds. The term "protein" also includes molecules which contain more than one protein joined by a disulfide bond, or complexes of proteins that are joined together, covalently or noncovalently, as multimers (e.g., dimers, tetramers). Thus, the terms peptide, oligopeptide, enzyme, and polypeptide are all included within the definition of protein and these terms are used interchangeably. It should be understood that these terms do not connote a specific length of a polymer of amino acids, nor are they intended to imply or distinguish whether the protein is produced using recombinant techniques, chemical or enzymatic synthesis, or is naturally occurring.

As used herein, a "mature protein" refers to a protein having an amino acid sequence that is identical to or having structural similarity with a protein that has been processed after translation to result in its final form. Post-translation processing can include N-terminal processing or C-terminal truncation. As used herein, a "preprocessed protein" refers to a protein that has been translated from a mRNA and has not undergone post-translation processing to result in a mature protein.

As used herein, an "isolated" substance, for instance a protein, is one that has been removed from its natural environment, produced using recombinant techniques, or chemically or enzymatically synthesized. For instance, a protein or a polynucleotide can be isolated. Preferably, a substance is purified, i.e., is at least 60% free, preferably at least 75% free, and most preferably at least 90% free from other components with which they are naturally associated.

As used herein, the term "polynucleotide" refers to a polymeric form of nucleotides of any length, either ribonucleotides or deoxynucleotides, and includes both double- and single-stranded RNA and DNA. A polynucleotide can be obtained directly from a natural source, or can be prepared with the aid of recombinant, enzymatic, or chemical techniques. A polynucleotide can be linear or circular in topology. A polynucleotide may be, for example, a portion of a vector, such as an expression or cloning vector, or a fragment. A polynucleotide may include nucleotide sequences having different functions, including, for instance, coding regions, and non-coding regions such as regulatory regions.

As used herein, a "detectable moiety" or "label" is a molecule that is detectable, either directly or indirectly, by spectroscopic, photochemical, biochemical, immunochemical, or chemical means. For example, useful labels include $^{32}P$, fluorescent dyes, electron-dense reagents, enzymes and their substrates (e.g., as commonly used in enzyme-linked immunoassays, e.g., alkaline phosphatase and horse radish peroxidase), biotin-streptavidin, digoxigenin, proteins such as antibodies, or haptens and proteins for which antisera or monoclonal antibodies are available. The label or detectable moiety is typically bound, either covalently, through a linker or chemical bound, or through ionic, van der Waals or hydrogen bonds to the molecule to be detected.

As used herein, the terms "coding region" and "coding sequence" are used interchangeably and refer to a nucleotide sequence that encodes a protein and, when placed under the control of appropriate regulatory sequences expresses the encoded protein. The boundaries of a coding region are generally determined by a translation start codon at its 5' end and a translation stop codon at its 3' end. A "regulatory sequence" is a nucleotide sequence that regulates expression of a coding sequence to which it is operably linked. Non-limiting examples of regulatory sequences include promoters, enhancers, transcription initiation sites, translation start sites, translation stop sites, and transcription terminators. The term "operably linked" refers to a juxtaposition of components such that they are in a relationship permitting them to function in their intended manner. A regulatory sequence is "operably linked" to a coding region when it is joined in such a way that expression of the coding region is achieved under conditions compatible with the regulatory sequence.

A polynucleotide that includes a coding region may include heterologous nucleotides that flank one or both sides of the coding region. As used herein, "heterologous nucleotides" refer to nucleotides that are not normally present flanking a coding region that is present in a wild-type cell. Thus, a polynucleotide that includes a coding region and heterologous nucleotides is not a naturally occurring molecule. For instance, a coding region present in a wild-type microbe and encoding a Pn3Pase protein is flanked by homologous sequences, and any other nucleotide sequence flanking the coding region is considered to be heterologous. Examples of heterologous nucleotides include, but are not limited to regulatory sequences. Typically, heterologous nucleotides are present in a polynucleotide described herein through the use of standard genetic and/or recombinant methodologies well known to one skilled in the art. A polynucleotide described herein may be included in a suitable vector.

A protein described herein may include heterologous amino acids present at the N-terminus, the C-terminus, or a combination thereof. As used herein, "heterologous amino acids" refer to amino acids that are not normally present flanking a protein that is naturally present in a wild-type cell. Thus, a protein that includes heterologous amino acids is not a naturally occurring molecule. For instance, a naturally occurring Pn3Pase protein present in a wild-type microbe does not have additional amino acids at either the N-terminal end or the C-terminal end, and any other amino acids present at the N-terminal end or the C-terminal end are considered to be heterologous. Examples of heterologous amino acid sequences are described herein, and include, but are not limited to affinity purification tags. Typically, heterologous amino acids are present in a protein described herein through the use of standard genetic and/or recombinant methodologies well known to one skilled in the art.

As used herein, an "exogenous polynucleotide" refers to a polynucleotide that is not normally or naturally found in a cell. As used herein, the term "endogenous polynucleotide" refers to a polynucleotide that is normally or naturally found in a cell. An "endogenous polynucleotide" is also referred to as a "native polynucleotide."

The terms "complement" and "complementary" as used herein, refer to the ability of two single stranded polynucleotides to base pair with each other, where an adenine on one strand of a polynucleotide will base pair to a thymine or uracil on a strand of a second polynucleotide and a cytosine on one strand of a polynucleotide will base pair to a guanine on a strand of a second polynucleotide. Two polynucleotides are complementary to each other when a nucleotide sequence in one polynucleotide can base pair with a nucleotide sequence in a second polynucleotide. For instance, 5'-ATGC and 5'-GCAT are complementary. The term "substantial complement" and cognates thereof as used herein refer to a polynucleotide that is capable of selectively hybridizing to a specified polynucleotide under stringent hybridization conditions. Stringent hybridization can take place under a number of pH, salt, and temperature conditions. The pH can vary from 6 to 9, preferably 6.8 to 8.5. The salt concentration can vary from 0.15 M sodium to 0.9 M sodium, and other cations can be used as long as the ionic strength is equivalent to that specified for sodium. The temperature of the hybridization reaction can vary from 30° C. to 80° C., preferably from 45° C. to 70° C. Additionally, other compounds can be added to a hybridization reaction to promote specific hybridization at lower temperatures, such as at or approaching room temperature. Among the compounds contemplated for lowering the temperature requirements is formamide. Thus, a polynucleotide is typically substantially complementary to a second polynucleotide if hybridization occurs between the polynucleotide and the second polynucleotide. As used herein, "specific hybridization" refers to hybridization between two polynucleotides under stringent hybridization conditions.

In the comparison of two amino acid sequences, structural similarity may be referred to by percent "identity" or may be referred to by percent "similarity." "Identity" refers to the presence of identical amino acids. "Similarity" refers to the presence of not only identical amino acids but also the presence of conservative substitutions. The sequence similarity between two proteins is determined by aligning the residues of the two proteins (e.g., a candidate amino acid sequence and a reference amino acid sequence, such as a mature Pn3Pase protein, e.g., amino acids 41-1545 of SEQ ID NO:2) to optimize the number of identical amino acids along the lengths of their sequences; gaps in either or both sequences are permitted in making the alignment in order to optimize the number of shared amino acids, although the amino acids in each sequence must nonetheless remain in their proper order. Sequence similarity may be determined, for example, using sequence techniques such as the BEST-FIT algorithm in the GCG package (Madison WI), or the Blastp program of the BLAST 2 search algorithm, as described by Tatusova, et al. (*FEMS Microbiol Lett* 1999, 174:247-250), and available through the World Wide Web, for instance at the internet site maintained by the National Center for Biotechnology Information, National Institutes of Health. Preferably, sequence similarity between two amino acid sequences is determined using the Blastp program of the BLAST 2 search algorithm. Preferably, the default values for all BLAST 2 search parameters are used. In the comparison of two amino acid sequences using the BLAST search algorithm, structural similarity is referred to as "identities." Thus, reference to a protein described herein, such as a mature Pn3Pase protein, e.g., amino acids 41-1545 of SEQ ID NO:2, can include a protein with at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity with the reference protein. Alternatively, reference to a protein described herein, such as a mature Pn3Pase protein, e.g., amino acids 41-1545 of SEQ ID NO:2, can include a protein with at least 80% similarity, at least 81% similarity, at least 82% similarity, at least 83% similarity, at least 84% similarity, at least 85% similarity, at least 86% similarity, at least 87% similarity, at least 88% similarity, at least 89% similarity, at least 90% similarity, at least 91% similarity, at least 92% similarity, at least 93% similarity, at least 94% similarity, at least 95% similarity, at least 96% similarity, at least 97% similarity, at least 98% similarity, or at least 99% similarity with the reference protein.

The sequence similarity between two polynucleotides is determined by aligning the residues of the two polynucleotides (e.g., a candidate nucleotide sequence and a reference nucleotide sequence encoding a mature Pn3Pase protein) to optimize the number of identical nucleotides along the lengths of their sequences; gaps in either or both sequences are permitted in making the alignment in order to optimize the number of shared nucleotides, although the nucleotides in each sequence must nonetheless remain in their proper order. Sequence similarity may be determined, for example, using sequence techniques such as GCG FastA (Genetics Computer Group, Madison, Wisconsin), MacVector 4.5 (Kodak/IBI software package) or other suitable sequencing programs or methods known in the art. Preferably, sequence similarity between two nucleotide sequences is determined using the Blastn program of the BLAST 2 search algorithm, as described by Tatusova, et al. (1999, *FEMS Microbiol Lett.,* 174:247-250), and available through the World Wide Web, for instance at the internet site maintained by the National Center for Biotechnology Information, National Institutes of Health. Preferably, the default values for all BLAST 2 search parameters are used. In the comparison of two nucleotide sequences using the BLAST search algorithm, sequence similarity is referred to as "identities." The sequence similarity is typically at least 50% identity, at least 55% identity, at least 60% identity, at least 65% identity, at least 70% identity, at least 75% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity.

As used herein, "in vitro" refers to an artificial environment and to processes or reactions that occur within an artificial environment. In vitro environments can include, but are not limited to, a test tube. As used herein, the term "in vivo" refers to a natural environment that is within the body of a subject.

Conditions that "allow" an event to occur or conditions that are "suitable" for an event to occur, such as an enzymatic reaction, or "suitable" conditions are conditions that do not prevent such events from occurring. Thus, these conditions permit, enhance, facilitate, and/or are conducive to the event.

The term "and/or" means one or all of the listed elements or a combination of any two or more of the listed elements.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

The terms "comprises" and variations thereof do not have a limiting meaning where these terms appear in the description and claims.

It is understood that wherever embodiments are described herein with the language "include," "includes," or "including," and the like, otherwise analogous embodiments described in terms of "consisting of" and/or "consisting essentially of" are also provided.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

Reference throughout this specification to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout this specification are not necessarily referring to the same embodiment of the disclosure. Furthermore, the particular features, configurations, compositions, or characteristics may be combined in any suitable manner in one or more embodiments.

The above summary of the present disclosure is not intended to describe each disclosed embodiment or every implementation of the present disclosure. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

In the description herein particular embodiments may be described in isolation for clarity. Unless otherwise expressly specified that the features of a particular embodiment are incompatible with the features of another embodiment, certain embodiments can include a combination of compatible features described herein in connection with one or more embodiments.

BRIEF DESCRIPTION OF THE FIGURES

The following detailed description of illustrative embodiments of the present disclosure may be best understood when read in conjunction with the following drawings.

FIG. 1 shows a repeating unit structure of *Streptococcus pneumoniae* (Spn) serotype 3 capsular polysaccharide.

FIG. 2 shows an amino acid alignment of seven glycoside hydrolases from *Paenibacillus*. WP_079915027.1 (SEQ ID NO:2), WP_113018908.1 (SEQ ID NO:4), WP_068663733.1 (SEQ ID NO:5), KRE82476.1 (SEQ ID NO:6), WP_082593776.1 (SEQ ID NO:7), WP_056617367.1 (SEQ ID NO:8), and WP_028553222.1 (SEQ ID NO:9).

(FIG. 3A) Growth of *Paenibacillus* sp. 32352 (Pbac) on minimal medium plus 2% (w/v) glucose, Pn3P, cellulose, or nothing as carbon source. (FIG. 3B) SDS-PAGE coomassie blue stained gel of concentrated culture supernatant of Pbac grown on glucose (lane 1) or Pn3P (lane 2). (FIG. 3C) Proposed locus of Pn3P utilization organization based on the Rapid Annotation Server (Aziz et al. 2008, BMC Genomics 9, 75) (RAST) annotation. (FIG. 3D) Real-Time PCR of select genes within putative locus in Pbac grown on 2% glucose or Pn3P, shown as fold change in expression in Pn3P culture versus glucose culture.

FIGS. 4A-4E show Pn3Pase identification and domain schematic of primary amino acid sequence. (FIG. 4A) Amino acid sequence (SEQ ID NO:2) and accession of Pn3Pase. (FIG. 4B) Separation of recombinant Pn3Pase depolymerized tritium radioisotope labeled Pn3P by size exclusion chromatography, measured by counts per minute in each 1 ml fraction. (FIG. 4C) Dot blot of recombinant Pn3Pase depolymerized cold Pn3P probed with Pn3P monoclonal antibody. (FIG. 4D) Schematic of predicted domains of Pn3Pase by InterPro. (FIG. 4E) A nucleotide sequence (SEQ ID NO:1) encoding a Pn3Pase.

(FIG. 7A) Time course assay of recombinant Pn3Pase depolymerized tritium radioisotope labeled Pn3P separated by size exclusion chromatography, measured by counts per minute in each 1 ml fraction. (FIG. 7B) Optimization of recombinant Pn3Pase in three different buffer conditions, measured by concentration of glucuronic acid reducing end generated in μg/ml. (FIG. 7C) Metal dependence determination with Mg2+ and Ca2+ reaction supplements, measured by concentration of glucuronic acid reducing end generated in μg/ml. Statistical significance was determined with the two-tailed Student t-test ** P<0.01

(FIG. 8A) Growth curve of WU2 in THY broth in the presence of 100 ug/ml Pn3Pase following the OD at 600 nm. (FIG. 8B-8C) Competition ELISA in which acapsular WU2, or Pn3Pase treated WU2 was used to compete for Pn3P specific antibody binding to Pn3P coated ELISA plate. Data is presented as percent inhibition of antibody binding. (FIG. 8D) Transmission Electron Microscopy of WU2 (upper left), acapsular derivative (upper right), and representative Pn3Pase treated WU2 (bottom panels). Statistical significance was determined with the two-tailed Student t test  P<0.01, * P<0.001.

FIGS. 9A-3B show the effects of Pn3Pase treatment on type 3 Spn viability. (FIG. 9A) Growth curve of WU2 in THY broth in the presence of 100 μg/ml Pn3Pase following the OD at 600 nm. (FIG. 9B) WU2 survival in PBS in the presence of 100 μg/ml active or heat inactivated Pn3Pase.

(FIGS. 10A-B) Competition ELISA in which acapsular WU2, WU2 treated with heat-inactivated Pn3Pase, or WU2 treated with Pn3Pase at two different concentrations (2 μg/ml or 10 μg/ml) were used to compete for Pn3P specific antibody binding to Pn3P coated ELISA plate. Data is presented as percent inhibition of antibody binding. Statistical significance was determined with the two-tailed Student t test  P<0.01, * P<0.001. Transmission electron microscopy images of WU2 mock treated with 2 μg/ml heat-inactivated Pn3Pase (FIG. 10C), acapsular WU2 strain (FIG. 10D) and 2 μg/ml active-Pn3Pase treated WU2 (FIG. 10E). Bottom panels are imaged at 15000× direct magnification and top panels are imaged at 10000× direct magnification (FIGS. 10C-10E).

(FIG. 11A) RAW 264.7 macrophage containing fluorescent streptococci following Heat inactivated (left) or active (right) Pn3Pase treatment. Streptococci, CFSE, green. Macrophage, Biotinylated-WGA, Streptavidin-APC, red. (FIG. 11B) Influence of Pn3Pase treatment and complement on macrophage uptake of CFSE labeled Spn quantified by flow cytometry. (FIG. 11C) Pn3Pase dose dependent effect on the percent of fluorescent phagocytes. Statistical significance was determined with the two-tailed Student t test *** P<0.001.

(FIG. 14A) Groups of mice were intranasally inoculated with 106 log-phase bacteria in 10 μl PBS. All inocula were chased with either 50 g of Pn3Pase or buffer control (10 1). Groups were dosed with the enzyme at either day 0 (WU2+Pn3Pase*1), day 0 and 3 (WU2+Pn3Pase*2), or day 0, 3, and 7 (WU2+Pn3Pase*3). Bacterial load was quantified on day 10. Serial dilutions of nasal lavage fluid were plated in duplicate to determine CFU values. (FIG. 14B) IL-6 and (FIG. 14C) TNFα concentrations in nasal lavage fluid was determined by ELISA. Statistical significance was determined with the two-tailed Student t test * P<0.05, ** P<0.01.

DETAILED DESCRIPTION OF ILLUSTRATIVE EMBODIMENTS

Proteins

Figure 1:
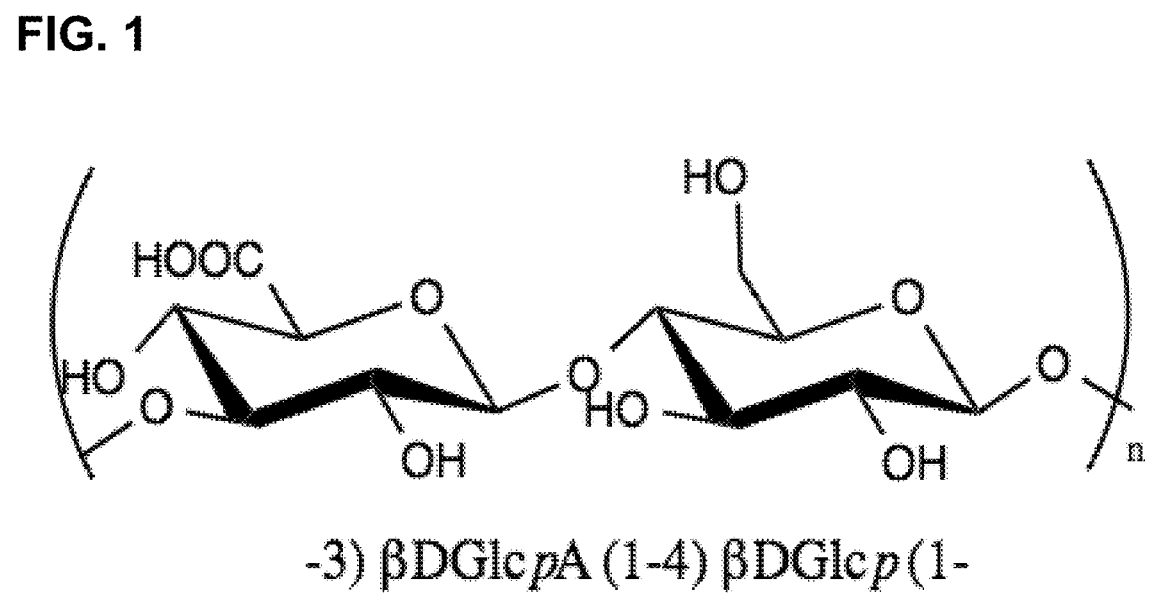
Figure 3A:
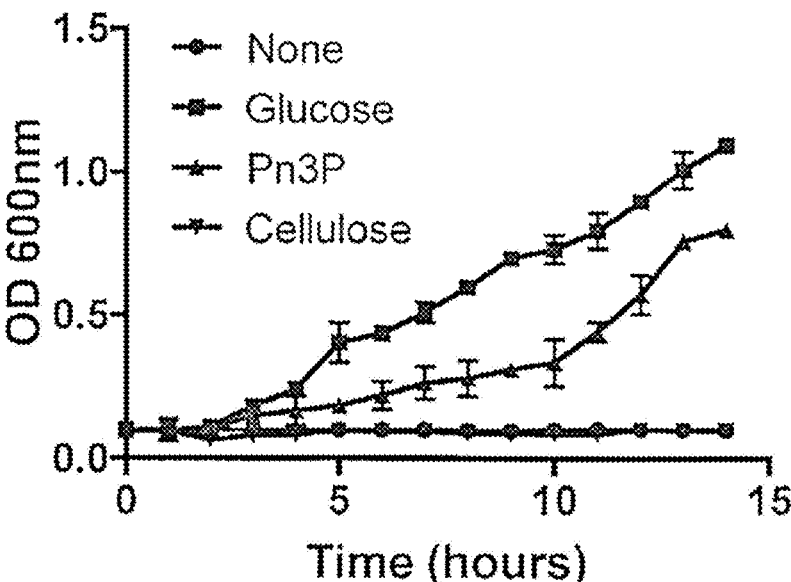
FIGS. 3A-3D show culture of *Paenibacillus* sp. 32352 in minimal medium with Pn3P as carbon source.

Provided herein are genetically modified cells and methods for using the cells. The genetically modified cells can produce a protein having Pn3Pase activity. A protein having Pn3Pase activity is referred to herein as a Pn3Pase protein or a Pn3Pase. A protein having Pn3Pase activity degrades type III capsular polysaccharide of *Streptococcus pneumoniae* (Spn). This capsular polysaccharide is also known as Pneumococcal type-3 polysaccharide (Pn3P) and is expressed by serotype 3 (also referred to as type 3) *S. pneumoniae*. The structure of Pn3P is shown in FIG. 1.

Whether a protein has Pn3Pase activity can be determined by in vitro assays. In one embodiment, an in vitro assay is carried out as described herein (see Example 1). Briefly, Pn3P can be labeled with a detectable moiety, exposed to a protein being tested for Pn3Pase activity, and the reaction products resolved using a method that permits detection of differences in molecular weight. Pn3P can be obtained using methods that are known to the skilled person and routine or can be purchased from American Type Culture Collection, ATCC (Manassas, VA). Methods for detecting changes in molecular weight of polysaccharides are known to the skilled person and are routine.

A Pn3Pase protein can be, and in some embodiments preferably is, a mature protein. In one embodiment, a Pn3Pase protein is encoded by a coding sequence obtained from a wild-type cell where the protein has been processed to remove one or more amino acids from the N-terminal end to result in a mature protein, e.g., the protein lacks a signal sequence. Thus, a mature protein can lack, when compared to a preprocessed Pn3Pase protein encoded by a coding sequence obtained from a wild-type cell, at least one, at least two, at least three, at least four, at least five, at least six, at least seven, at least eight, at least nine, at least ten, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, at least 60, at least 61, at least 62, or at least 63 amino acids from the amino terminus of the preprocessed protein. In another embodiment, a Pn3Pase protein is encoded by a coding region that does not include nucleotides encoding amino acids corresponding to a signal sequence.

An example of a Pn3Pase protein is depicted at SEQ ID NO:2, where the Pn3Pase protein is a preprocessed protein. Examples of a mature Pn3Pase protein include an amino acid sequence having an N-terminal amino acid that is selected from amino acid 2-64 of SEQ ID NO:2 and the C-terminal amino acid is residue 1545 of SEQ ID NO:2. Other examples of Pn3Pase proteins include those having sequence similarity with the amino acid sequence of SEQ ID NO:2 or a mature Pn3Pase protein that includes a subset of amino acids of SEQ ID NO:2. A Pn3Pase protein having sequence similarity with the amino acid sequence of SEQ ID NO:2 or a portion thereof has Pn3Pase activity. A preprocessed or mature Pn3Pase protein may be isolated from a microbe, such as a member of the genera *Bacillus*, such as *B. circulans*. A specific example of a microbe is *Bacillus circulans* Jordan strain 32352 (ATCC 14175). Data from determining the nucleotide sequence of *Bacillus circulans* indicates this bacterium should be reclassified in the genus *Paenibacillus*, as its nearest neighbors phylogenetically lie within this classification. *Paenibacillus* species were previously included within the *Bacillus* genus until they were deemed appropriately dissimilar (Ash et al., 1993, *Antonie Van Leeuwenhoek* 64:253-260). Classification into the *Paenibacillus* genus was confirmed by the presence of the unique group 3 bacilli (Paenibacilli) nucleotide sequence (TCGATACCCTTGGTGCCGAAGT, SEQ ID NO:3) on 16s ribosomal RNA (Ash et al., 1993, *Antonie Van Leeuwenhoek* 64:253-260). A Pn3Pase protein can also be produced using recombinant techniques, or chemically or enzymatically synthesized using routine methods. A recombinantly-produced protein may include the entire amino acid sequence translatable from an mRNA transcript, or a portion thereof that encodes a mature Pn3Pase protein.

The amino acid sequence of a Pn3Pase protein having sequence similarity to SEQ ID NO:2 or a portion thereof corresponding to a mature Pn3Pase protein may include conservative substitutions of amino acids. A conservative substitution is typically the substitution of one amino acid for another that is a member of the same class. For example, it is well known in the art of protein biochemistry that an amino acid belonging to a grouping of amino acids having a particular size or characteristic (such as charge, hydrophobicity, and/or hydrophilicity) may generally be substituted for another amino acid without substantially altering the secondary and/or tertiary structure of a protein. For the purposes of this disclosure, conservative amino acid substitutions are defined to result from exchange of amino acids residues from within one of the following classes of residues: Class I: Gly, Ala, Val, Leu, and Ile (representing aliphatic side chains); Class II: Gly, Ala, Val, Leu, Ile, Ser, and Thr (representing aliphatic and aliphatic hydroxyl side chains); Class III: Tyr, Ser, and Thr (representing hydroxyl side chains); Class IV: Cys and Met (representing sulfur-containing side chains); Class V: Glu, Asp, Asn and Gln (carboxyl or amide group containing side chains); Class VI: His, Arg and Lys (representing basic side chains); Class VII: Gly, Ala, Pro, Trp, Tyr, Ile, Val, Leu, Phe and Met (representing hydrophobic side chains); Class VIII: Phe, Trp, and Tyr (representing aromatic side chains); and Class IX: Asn and Gln (representing amide side chains). The classes are not limited to naturally occurring amino acids, but also include artificial amino acids, such as beta or gamma amino acids and those containing non-natural side chains, and/or other similar monomers such as hydroxyacids.

Guidance concerning how to make phenotypically silent amino acid substitutions is provided in Bowie et al. (1990, Science, 247:1306-1310), wherein the authors indicate proteins are surprisingly tolerant of amino acid substitutions. For example, Bowie et al. disclose that there are two main approaches for studying the tolerance of a protein sequence to change. The first method relies on the process of evolution, in which mutations are either accepted or rejected by natural selection. The second approach uses genetic engineering to introduce amino acid changes at specific positions of a cloned gene and selects or screens to identify sequences that maintain functionality. As stated by the authors, these studies have revealed that proteins are surprisingly tolerant of amino acid substitutions. The authors further indicate which changes are likely to be permissive at a certain position of the protein. For example, most buried amino acid residues require non-polar side chains, whereas few features of surface side chains are generally conserved. Other such phenotypically silent substitutions are described in Bowie et al, and the references cited therein.

Guidance on how to modify the amino acid sequences of proteins disclosed herein is also provided at FIG. 2. FIG. 2 depicts a Clustal Omega amino acid alignment of glycoside hydrolase proteins expressed by *Paenibacillus*. Clustal Omega is a multiple sequence alignment program (Sievers et al., 2011, Molecular Systems Biology 7: 539, doi:10.1038/msb.2011.75; Goujon et al., 2010, Nucleic acids research 38 (Suppl 2):W695-9, doi:10.1093/nar/gkg313). In FIG. 2 an asterisk (*) indicates positions which have a single, fully conserved residue; a colon (:) indicates conservation between groups of strongly similar properties, roughly equivalent to scoring >0.5 in the Gonnet PAM 250 matrix; a period (.) indicates conservation between groups of weakly similar properties, roughly equivalent to scoring=<0.5 and >0 in the Gonnet PAM 250 matrix. By reference to this figure, the skilled person can predict which alterations to an amino acid sequence are likely to modify enzymatic activity, as well as which alterations are unlikely to modify enzymatic activity.

Pn3Pase proteins include conserved domains including a glycoside hydrolase, family 39 domain (amino acids 180-353 of SEQ ID NO:2), galactose-binding domain-like (amino acids 621-765 of SEQ ID NO:2), a domain of unknown function DUF1080 (amino acids 781-950 of SEQ ID NO:2) with structural similarity to an endo-1,3-1,4-beta glucanase, and a concanavalin A-like lectin/glucanase domain (amino acids 1,209-1,348 of SEQ ID NO:2). In one embodiment, a Pn3Pase protein has the characteristic of displaying slightly better activity in sodium phosphate buffer at pH 7.2 than in MES buffer pH 6.0, and significantly worse in Tris buffer at pH 8.0 (see example 1). In another embodiment, a Pn3Pase protein displays a concentration-dependent preference for Ca2+, as it produces a higher concentration of reducing end GlcA in presence of 10 mM Ca2+ (see example 1).

A Pn3Pase protein described herein can be expressed as a fusion protein that includes a Pn3Pase protein described herein and heterologous amino acids. For instance, the additional amino acid sequence may be useful for purification of the fusion protein by affinity chromatography. Amino acid sequences useful for purification can be referred to as a tag, and include but are not limited to a polyhistidine-tag (His-tag) and maltose-binding protein. Representative examples may be found in Hopp et al. (U.S. Pat. No. 4,703,004), Hopp et al. (U.S. Pat. No. 4,782,137), Sgarlato (U.S. Pat. No. 5,935,824), and Sharma Sgarlato (U.S. Pat. No. 5,594,115). Various methods are available for the addition of such affinity purification moieties to proteins. Optionally, the additional amino acid sequence, such as a His-tag, can then be cleaved.

Polynucleotides

Also provided herein are isolated polynucleotides encoding a Pn3Pase protein. A polynucleotide encoding a protein having Pn3Pase activity is referred to herein as a Pn3Pase polynucleotide. Pn3Pase polynucleotides may have a nucleotide sequence encoding a protein having the amino acid sequence shown in SEQ ID NO:2, or a portion thereof. An example of the class of nucleotide sequences encoding such a protein is SEQ ID NO:1 or a portion thereof. It should be understood that a polynucleotide encoding a Pn3Pase protein represented by SEQ ID NO:2 is not limited to the nucleotide sequence disclosed at SEQ ID NO:1, but also includes the class of polynucleotides encoding such proteins as a result of the degeneracy of the genetic code. For example, the naturally occurring nucleotide sequence SEQ ID NO:1 is but one member of the class of nucleotide sequences encoding a protein having the amino acid sequence SEQ ID NO:2. The class of nucleotide sequences encoding a selected protein sequence is large but finite, and the nucleotide sequence of each member of the class may be readily determined by one skilled in the art by reference to the standard genetic code, wherein different nucleotide triplets (codons) are known to encode the same amino acid.

A Pn3Pase polynucleotide may have sequence similarity with the nucleotide sequence of SEQ ID NO:1 or a portion thereof, for instance nucleotides encoding a mature Pn3Pase protein. Pn3Pase polynucleotides having sequence similarity with the nucleotide sequence of SEQ ID NO:1, or a portion thereof, encode a Pn3Pase protein. A Pn3Pase polynucleotide may be isolated from a microbe, such as *Paenibacillus* sp., or may be produced using recombinant techniques, or chemically or enzymatically synthesized. A Pn3Pase polynucleotide may further include heterologous nucleotides flanking the open reading frame encoding the Pn3Pase protein. Typically, heterologous nucleotides may be at the 5' end of the coding region, at the 3' end of the coding region, or the combination thereof. The number of heterologous nucleotides may be, for instance, at least 10, at least 100, or at least 1000.

A polynucleotide described herein may be present in a vector. A vector is a replicating polynucleotide, such as a plasmid, phage, or cosmid, to which another polynucleotide may be attached so as to bring about the replication of the attached polynucleotide. Construction of vectors containing a polynucleotide of the disclosure employs standard ligation techniques known in the art. See, e.g., Sambrook et al, Molecular Cloning: A Laboratory Manual., Cold Spring Harbor Laboratory Press (1989). A vector may provide for further cloning (amplification of the polynucleotide), i.e., a cloning vector, or for expression of the polynucleotide, i.e., an expression vector. The term vector includes, but is not limited to, plasmid vectors, viral vectors, cosmid vectors, and artificial chromosome vectors. Examples of viral vectors include, for instance, adenoviral vectors, adeno-associated viral vectors, lentiviral vectors, retroviral vectors, and herpes virus vectors. Typically, a vector is capable of replication in a microbial host, for instance, a microbe such as *E. coli*, or in a eukaryotic host, for instance, a yeast cell, a mammalian cell, or an insect cell. In one embodiment the vector is a plasmid.

Selection of a vector depends upon a variety of desired characteristics in the resulting construct, such as a selection marker, vector replication rate, and the like. In some aspects, suitable host cells for cloning or expressing the vectors herein include prokaryotic cells. Vectors may be introduced into a host cell using methods that are known and used routinely by the skilled person. For example, calcium phosphate precipitation, electroporation, heat shock, lipofection, microinjection, and viral-mediated nucleic acid transfer are common methods for introducing nucleic acids into host cells.

Polynucleotides encoding a Pn3Pase protein may be obtained from microbes, for instance, a microbe such as *Paenibacillus* sp., or produced in vitro or in vivo. For instance, methods for in vitro synthesis include, but are not limited to, chemical synthesis with a conventional DNA/RNA synthesizer. Commercial suppliers of synthetic polynucleotides and reagents for such synthesis are well known.

An expression vector optionally includes regulatory sequences operably linked to the coding region. The disclosure is not limited by the use of any particular promoter, and a wide variety of promoters are known. Promoters act as regulatory signals that bind RNA polymerase in a cell to initiate transcription of a downstream (3' direction) coding region. The promoter used may be a constitutive or an inducible promoter. It may be, but need not be, heterologous with respect to the host cell. The promoter useful in methods described herein may be, but is not limited to, a constitutive promoter, a temperature sensitive promoter, a non-regulated promoter, or an inducible promoter. In one embodiment, a promoter is one that functions in a member of the domain Bacteria. In one embodiment, a promoter is one that functions in a eukaryote.

An expression vector may optionally include a ribosome binding site and a start site (e.g., the codon ATG) to initiate translation of the transcribed message to produce the protein. It may also include a termination sequence to end translation. A termination sequence is typically a codon for which there exists no corresponding aminoacetyl-tRNA, thus ending protein synthesis. The polynucleotide used to transform the host cell may optionally further include a transcription termination sequence.

A vector introduced into a host cell to result in a genetically modified cell optionally includes one or more marker sequences, which typically encode a molecule that inactivates or otherwise detects or is detected by a compound in the growth medium. For example, the inclusion of a marker sequence may render the transformed cell resistant to an antibiotic, or it may confer compound-specific metabolism on the transformed cell. Examples of a marker sequence include, but are not limited to, sequences that confer resistance to kanamycin, ampicillin, chloramphenicol, tetracycline, streptomycin, and neomycin.

Proteins described herein may be produced using recombinant DNA techniques, such as an expression vector present in a cell. Such methods are routine and known in the art. The proteins may also be synthesized in vitro, e.g., by solid phase peptide synthetic methods. The solid phase peptide synthetic methods are routine and known in the art. A protein produced using recombinant techniques or by solid phase peptide synthetic methods may be further purified by routine methods, such as fractionation on immunoaffinity or ion-exchange columns, ethanol precipitation, reverse phase HPLC, chromatography on silica or on an anion-exchange resin such as DEAE, chromatofocusing, SDS-PAGE, ammonium sulfate precipitation, gel filtration using, for example, Sephadex G-75, or ligand affinity.

Genetically Modified Cells

Also provided is a genetically modified cell having a polynucleotide encoding a Pn3Pase described herein. Compared to a control cell that is not genetically modified, a genetically modified cell can exhibit production of a Pn3Pase, or can exhibit increased production of a Pn3Pase. A polynucleotide encoding a Pn3Pase may be present in the cell as a vector or integrated into genomic DNA, such as a chromosome or a plasmid, of the genetically modified cell. A cell can be a eukaryotic cell or a prokaryotic cell, such as a member of the domain Bacteria Examples of host cells that are members of the domain Bacteria that can be genetically modified to include a polynucleotide encoding a Pn3Pase described herein include, but are not limited to, *Escherichia* (such as *Escherichia coli*), and *Salmonella* (such as *Salmonella enterica, Salmonella typhi, Salmonella typhimurium*).

Examples of host cells that are eukaryotic cells that can be genetically modified to include a polynucleotide encoding a Pn3Pase include, but are not limited to, yeast such as *Saccharomyces cerevisiae* and *Pichia* spp., insect cells, and mammalian cells.

Compositions

Also provided are compositions that include a Pn3Pase protein described herein or a polynucleotide encoding a Pn3Pase protein. Such compositions typically include a pharmaceutically acceptable carrier. As used herein "pharmaceutically acceptable carrier" includes saline, solvents, dispersion media, coatings, antibacterial and antifungal agents, isotonic and absorption delaying agents, and the like, compatible with pharmaceutical administration. Additional active agents can also be incorporated into the compositions.

A composition may be prepared by methods well known in the art of pharmaceutics. In general, a composition can be formulated to be compatible with its intended route of administration. Administration may be systemic or local. Examples of routes of administration include parenteral (e.g., intravenous, intradermal, subcutaneous, intraperitoneal, intramuscular), enteral (e.g., oral), and topical (e.g., epicutaneous, inhalational, transmucosal) administration. Appropriate dosage forms for enteral administration of the compound of the present disclosure include, but are not limited to, tablets, capsules or liquids. Appropriate dosage forms for parenteral administration may include intravenous or intraperitoneal administration. Appropriate dosage forms for topical administration include, but are not limited to, nasal sprays, metered dose inhalers, dry-powder inhalers or by nebulization.

Solutions or suspensions can include the following components: a sterile diluent such as water for administration, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates; electrolytes, such as sodium ion, chloride ion, potassium ion, calcium ion, and magnesium ion, and agents for the adjustment of tonicity such as sodium chloride or dextrose. pH can be adjusted with acids or bases, such as hydrochloric acid or sodium hydroxide.

Compositions can include sterile aqueous solutions (where water soluble) or dispersions and sterile powders for the extemporaneous preparation of sterile solutions or dispersions. For parenteral administration, suitable carriers include physiological saline, bacteriostatic water, phosphate buffered saline (PBS), and the like. A composition is typically sterile and, when suitable for injectable use, should be fluid to the extent that easy syringability exists. It should be stable under the conditions of manufacture and storage and preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile solutions can be prepared by incorporating the active compound (e.g., a Pn3Pase protein described herein or a polynucleotide encoding the protein) in the required amount in an appropriate solvent with one or a combination of ingredients routinely used in pharmaceutical compositions, as required, followed by filtered sterilization. Generally, dispersions are prepared by incorporating the active compound into a sterile vehicle, which contains a basic dispersion medium and any other appropriate ingredients. In the case of sterile powders for the preparation of sterile injectable solutions, preferred methods of preparation include vacuum drying and freeze-drying which yields a powder of the active ingredient plus any additional desired ingredient from a previously sterilized solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier. Pharmaceutically compatible binding agents and/or other useful materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation (e.g., topical administration), the active compounds can be delivered in the form of an aerosol spray from a pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

In those embodiments where a polynucleotide encoding a recombinant protein is administered, any method suitable for administration of polynucleotide agents can be used, such as gene guns, bio injectors, and skin patches as well as needle-free methods such as micro-particle DNA vaccine technologies (Johnston et al., U.S. Pat. No. 6,194,389).

The active compounds may be prepared with carriers that will protect the compound against rapid elimination from the body, such as a controlled release formulation, including implants. Biodegradable, biocompatible polymers can be used, such as ethylene vinyl acetate, polyanhydrides, polyglycolic acid, collagen, polyorthoesters, and polylactic acid. Such formulations can be prepared using standard techniques. Liposomal suspensions can also be used as pharmaceutically acceptable carriers. These can be prepared according to methods known to those skilled in the art.

Toxicity and therapeutic efficacy of the active compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Recombinant proteins exhibiting high therapeutic indices are preferred.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration used. For a compound used in the methods described herein, the therapeutically effective dose can be estimated initially from animal models. A dose may be formulated in animal models to achieve a circulating plasma concentration range that includes the IC50 (i.e., the concentration of the test compound which achieves a half-maximal inhibition of signs of disease, such as obesity). Such information can be used to more accurately determine useful doses in humans. Levels in plasma may be measured using routine methods.

The compositions can be administered one or more times per day to one or more times per week, including once every other day. The skilled artisan will appreciate that certain factors may influence the dosage and timing required to effectively treat a subject, including but not limited to the severity of the condition, previous treatments, the general health and/or age of the subject, and other diseases present. Moreover, treatment of a subject with an effective amount of an active compound can include a single treatment or, preferably, can include a series of treatments.

Methods of Use

Also provided are methods. In one embodiment, a method is for making Pn3Pase protein described herein. In one embodiment, the method includes incubating a cell under suitable conditions for expression of a Pn3Pase protein. The cell can be, but it not limited to, a genetically modified cell or a naturally occurring cell that produces a Pn3Pase protein. An example of a naturally occurring cell is a *Paenibacillus* strain, such as *Paenibacillus* sp. 32352. Optionally, the method includes introducing into a host cell a vector that includes a coding region encoding a Pn3Pase protein. In one embodiment, the method includes isolating or purifying the Pn3Pase protein from a cell or from a medium. In those embodiments where the Pn3Pase protein includes additional amino acids useful for isolating or purifying the protein, the method can also include cleavage of the additional amino acids from the Pn3Pase protein.

In one embodiment, a method is for cleaving a Pn3P molecule. In one embodiment, the method includes exposing a Pn3P molecule to a Pn3Pase protein. The P3nP molecule can be part of a *Streptococcus pneumoniae* microbe, e.g., the Pn3P molecule can be the capsular polysaccharide of an *S. pneumoniae*, or the Pn3P molecule can be separate from an *S. pneumoniae* microbe, e.g., the Pn3P molecule can be isolated. In one embodiment, the *S. pneumoniae* microbe is serotype 3. In one embodiment, the Pn3P molecule is in vivo, and in another embodiment, the Pn3P molecule is in vitro.

In one embodiment, a method is for reducing the amount of type III capsular polysaccharide on the surface of *Streptococcus pneumoniae*. The method includes contacting a *Streptococcus pneumoniae* having type III capsular polysaccharide present on its surface with a Pn3Pase protein. The Pn3Pase protein can be isolated or purified, and can be present in a composition. In one embodiment, the contacting can include exposing the microbe to a genetically modified cell that expresses the Pn3Pase protein. The contacting can be under conditions suitable for enzymatic hydrolysis of type III capsular polysaccharide. Optionally, the the *Strep-*

*tococcus pneumoniae* with the reduced amount of type III capsular polysaccharide has increased susceptibility to phagocytosis by macrophages, increased complement-mediated killing by neutrophils, or a combination thereof, compared to the *Streptococcus pneumoniae* that is not contacted with the Pn3Pase protein. In one embodiment, the *S. pneumoniae* microbe is serotype 3. In one embodiment, the *S. pneumoniae* microbe is in vivo, and in another embodiment, the *S. pneumoniae* microbe is in vitro.

In one embodiment, a method is for increasing deposition of at least one complement component on the surface of *Streptococcus pneumoniae*. The method includes contacting a *Streptococcus pneumoniae* having type III capsular polysaccharide present on its surface with a Pn3Pase protein. The Pn3Pase protein can be isolated or purified, and can be present in a composition. In one embodiment, the contacting can include exposing the microbe to a genetically modified cell that expresses the Pn3Pase protein. The contacting can be under conditions suitable for enzymatic hydrolysis of type III capsular polysaccharide. In one embodiment, the *S. pneumoniae* microbe is serotype 3. In one embodiment, the *S. pneumoniae* microbe is in vivo, and in another embodiment, the *S. pneumoniae* microbe is in vitro.

In one embodiment, a method includes treating an infection in a subject caused by *Streptococcus pneumoniae*. The subject used in a method described herein can be an animal such as, but not limited to, a murine (e.g., mouse or rat) or a human. The method includes administering an effective amount of the composition to an animal having an infection caused by *Streptococcus pneumoniae*. Optionally, the method can include determining whether the *Streptococcus pneumoniae* causing the infection has decreased. Methods for determining whether an infection is caused by a *Streptococcus pneumoniae* are routine and known in the art. The infection can be localized or systemic. An example of a localized *Streptococcus pneumoniae* infection is colonization of the nasal cavity, e.g., the nasopharynx. In one embodiment, topical administration of a composition described herein can be used to reduce nasopharyngeal colonization in a subject. Another example of a localized *Streptococcus pneumoniae* infection of the lung, e.g., pneumococcal pneumonia. In one embodiment, topical administration of a composition by, for instance, aerosol, can be used to reduce pneumococcal pneumonia in a subject. An example of a systemic *Streptococcus pneumoniae* infection is the presence of *Streptococcus pneumoniae* in the blood of a subject (e.g., bacteremia or sepsis). In one embodiment, parenteral administration of a composition can be used to reduce a systemic *Streptococcus pneumoniae* infection in a subject. In this aspect of the disclosure, an "effective amount" of a composition of the present disclosure is the amount able to elicit the desired response in the recipient, e.g., a reduction in the amount of *Streptococcus pneumoniae* present in a subject. The reduction can be a reduction in the number of *S. pneumoniae* in the nasopharynx, lung, or blood of a subject. The reduction can be a decrease of at least 2-fold, at least 3-fold, or at least 4-fold in the subject compared to the subject before administering the composition. In one embodiment, the *S. pneumoniae* microbe is serotype 3.

In another embodiment, a method includes treating one or more symptoms of certain conditions in animals that may be caused by infection by a *Streptococcus pneumoniae*. *Streptococcus pneumoniae* infections cause invasive pneumococcal disease. Examples of conditions caused by invasive pneumococcal disease include pneumonia, pneumococcal meningitis, otitis media, bacteremia, and sepsis. Symptoms associated with these conditions include chills, cough, rapid breathing, difficulty breathing, chest pain (pneumonia), stiff neck, fever, headache, confusion and photophobia (pneumococcal meningitis), and confusion, shortness of breath, elevated heart rate, pain or discomfort, over-perspiration, fever, and shivering (sepsis). In one embodiment, the *S. pneumoniae* microbe is serotype 3.

Treatment of one or more of these conditions can be prophylactic or, alternatively, can be initiated after the development of a condition described herein. Treatment that is prophylactic, for instance, initiated before a subject manifests a symptom of a condition caused by *Streptococcus pneumoniae*, is referred to herein as treatment of a subject that is "at risk" of developing the condition. Typically, an animal "at risk" of developing a condition is an animal likely to be exposed to a *Streptococcus pneumoniae* causing the condition. Accordingly, administration of a composition can be performed before, during, or after the occurrence of the conditions described herein. Treatment initiated after the development of a condition may result in decreasing the severity of the symptoms of one of the conditions, including completely removing the symptoms. In this aspect of the disclosure, an "effective amount" is an amount effective to prevent the manifestation of symptoms of a condition, decrease the severity of the symptoms of a condition, and/or completely remove the symptoms. In one embodiment, the *S. pneumoniae* microbe is serotype 3.

The potency of a composition described herein can be tested according to standard methods. For instance, the use of mice as an experimental model for *Streptococcus pneumoniae* infection in humans is well established.

Kits

The present disclosure also provides a kit for making a Pn3Pase protein. In one embodiment, the kit includes a vector that includes a coding region encoding a Pn3Pase protein in an amount sufficient for transforming a cell. In one embodiment, the kit includes a genetically modified cell that includes a coding region encoding a Pn3Pase protein in a suitable packaging material.

In another embodiment, the present disclosure also provides a kit directed to using a Pn3Pase protein. In one embodiment, the kit includes Pn3Pase protein, isolated or optionally purified, in a suitable packaging material.

Optionally, other reagents such as buffers or a pharmaceutically acceptable carrier (either prepared or present in its constituent components, where one or more of the components may be premixed or all of the components may be separate), and the like, are also included. In one embodiment, the protein, vector, or genetically modified cell may be present with a buffer, or may be present in separate containers. Instructions for use of the packaged components are also typically included.

As used herein, the phrase "packaging material" refers to one or more physical structures used to house the contents of the kit. The packaging material is constructed by known methods, preferably to provide a sterile, contaminant-free environment. The packaging material has a label, which indicates that the contents can be used for transforming a cell or producing Pn3Pase protein. In addition, the packaging material contains instructions indicating how the materials within the kit are used. As used herein, the term "package" refers to a solid matrix or material such as glass, plastic, paper, foil, and the like, capable of holding within fixed limits a vector or a genetically modified cell. Thus, for example, a package can include a glass or plastic vial used to contain appropriate quantities of a Pn3Pase protein.

"Instructions for use" typically include a tangible expression describing the reagent concentration or at least one method parameter.

ILLUSTRATIVE ASPECTS

Aspect 1. A genetically modified cell comprising a mature Pn3Pase protein, wherein the protein has Pn3Pase activity.

Aspect 2. A genetically modified cell comprising a polynucleotide comprising a coding region, wherein the coding region comprises a nucleotide sequence encoding a mature Pn3Pase protein, and wherein the protein has Pn3Pase activity.

Aspect 3. The genetically modified cell of Aspect 1 or 2 wherein the protein comprises an amino acid sequence having at least 80% identity with an amino acid sequence selected from SEQ ID NO:2, wherein the amino terminal amino acid is selected from any one of residues 2 to 64 of SEQ ID NO:2 and the carboxy terminal amino acid is residue 1545 of SEQ ID NO:2.

Aspect 4. The genetically modified cell of any one of Aspects 1-3 wherein the protein comprises an amino acid sequence having at least 80% identity with amino acids 41-1545 of SEQ ID NO:2.

Aspect 5. The genetically modified cell of any one of Aspects 1-4 wherein the cell is a eukaryotic cell.

Aspect 6. The genetically modified cell of any one of Aspects 1-5 wherein the cell is a mammalian cell, a yeast cell, or an insect cell.

Aspect 7. The genetically modified cell of any one of Aspects 1-6 wherein the cell is a prokaryotic cell.

Aspect 8. The genetically modified cell of any one of Aspects 1-7 wherein the cell is *E. coli.*

Aspect 9. The genetically modified cell of any one of Aspects 1-8 wherein the protein comprises a heterologous amino acid sequence.

Aspect 10. The genetically modified cell of any one of Aspects 1-9 wherein the heterologous amino acid sequence comprises a tag.

Aspect 11. A composition comprising the genetically modified cell of any one of Aspects 1-10.

Aspect 12. A composition comprising an isolated mature P3nPase protein, wherein the protein has Pn3Pase activity.

Aspect 13. The composition of any one of Aspects 1-12 wherein the protein is purified.

Aspect 14. A composition comprising an isolated polynucleotide, wherein the polynucleotide comprises a coding region encoding a mature Pn3Pase protein, and wherein the protein has Pn3Pase activity.

Aspect 15. The composition of any one of Aspects 12-14 wherein the protein comprises an amino acid sequence having at least 80% identity with an amino acid sequence selected from SEQ ID NO:2, wherein the amino terminal amino acid is selected from residues 2 to 64 of SEQ ID NO:2 and the carboxy terminal amino acid is residue 1545 of SEQ ID NO:2.

Aspect 16. The composition of any one of Aspects 12-15 wherein the protein comprises an amino acid sequence having at least 80% identity with amino acids 41-1545 of SEQ ID NO:2.

Aspect 17. The composition of any one of Aspects 11-16 wherein the composition comprises a pharmaceutically acceptable carrier.

Aspect 18. A method comprising: incubating a cell under conditions suitable for expression of a protein having Pn3Pase activity, wherein the cell comprises a polynucleotide comprising a coding region, wherein the coding region comprises a nucleotide sequence encoding a mature Pn3Pase protein, wherein the protein has Pn3Pase activity, and wherein the cell expresses the mature Pn3Pase protein.

Aspect 19. The method of Aspect 18 wherein the protein comprises an amino acid sequence having at least 80% identity with an amino acid sequence selected from SEQ ID NO:2, wherein the amino terminal amino acid is selected from any one of residues 2 to 64 of SEQ ID NO:2 and the carboxy terminal amino acid is residue 1545 of SEQ ID NO:2.

Aspect 20. The method of any one of Aspects 18-19 wherein the protein comprises an amino acid sequence having at least 80% identity with amino acids 41-1545 of SEQ ID NO:2.

Aspect 21. The method of any one of Aspects 18-20 wherein the cell is a genetically modified cell and the polynucleotide is an exogenous polynucleotide.

Aspect 22. The method of any one of Aspects 18-21 further comprising isolating the protein.

Aspect 23. The method of any one of Aspects 18-21 further comprising purifying the protein.

Aspect 24. The method of any one of Aspects 18-21 wherein the cell is a eukaryotic cell.

Aspect 25. The method of any one of Aspects 18-24 wherein the cell is a mammalian cell, a yeast cell, or an insect cell.

Aspect 26. The method of any one of Aspects 18-25 wherein the cell is a prokaryotic cell.

Aspect 27. The method of any one of Aspects 18-26 wherein the prokaryotic cell is *E. coli.*

Aspect 28. The method of any one of Aspects 18-27 wherein the protein comprises a heterologous amino acid sequence.

Aspect 29. The method of any one of Aspects 18-28 wherein the heterologous amino acid sequence comprises a tag.

Aspect 30. A method comprising:

contacting a *Streptococcus pneumoniae* comprising a type III capsular polysaccharide with a mature Pn3Pase protein comprising Pn3Pase activity, wherein the contacting is under conditions suitable for enzymatic hydrolysis of type III capsular polysaccharide, wherein the amount of type III capsular polysaccharide on the surface of the *S. pneumoniae* is reduced compared to the *S. pneumoniae* that is not contacted with the Pn3Pase protein.

Aspect 31. A method for increasing deposition of at least one complement component on the surface of a *Streptococcus pneumoniae*, the method comprising:

contacting a *Streptococcus pneumoniae* comprising a type III capsular polysaccharide with a mature Pn3Pase protein comprising Pn3Pase activity, wherein the deposition of at least one complement component on the surface of the *S. pneumoniae* is increased compared to the *S. pneumoniae* that is not contacted with the Pn3Pase protein.

Aspect 32. The method of Aspect 30 or 31 wherein the protein comprises an amino acid sequence having at least 80% identity with an amino acid sequence selected from SEQ ID NO:2, wherein the amino terminal amino acid is selected from any one of residues 2 to 64 of SEQ ID NO:2 and the carboxy terminal amino acid is residue 1545 of SEQ ID NO:2.

Aspect 33. The method of any one of Aspects 30-32 wherein the protein comprises an amino acid sequence having at least 80% identity with amino acids 41-1545 of SEQ ID NO:2.

Aspect 34. The method of any one of Aspects 30-33 wherein the *S. pneumoniae* is present in conditions suitable for replication of the *S. pneumoniae*.

Aspect 35. The method of any one of Aspects 30-34 wherein the mature Pn3Pase protein is an isolated Pn3Pase protein.

Aspect 36. The method of any one of Aspects 30-35 wherein the contacting comprises exposing the *S. pneumoniae* to a genetically modified cell that expresses the mature Pn3Pase protein.

Aspect 37. The method of any one of Aspects 30-36 wherein the *S. pneumoniae* has increased susceptibility to phagocytosis by macrophages, increased complement-mediated killing by neutrophils, or a combination thereof, compared to the *S. pneumoniae* that is not contacted with the Pn3Pase protein.

Aspect 38. The method of any one of Aspects 30-37 wherein the *S. pneumoniae* is present in a subject.

Aspect 39. A method for treating an infection in a subject, the method comprising:

administering an effective amount of a composition comprising a mature Pn3Pase protein having Pn3Pase activity to a subject having or at risk of having an infection caused by a serotype 3 *S. pneumoniae*.

Aspect 40. A method for treating a symptom in a subject, the method comprising:

administering an effective amount of a composition comprising a mature Pn3Pase protein having Pn3Pase activity to a subject having or at risk of having an infection caused by a serotype 3 *S. pneumoniae*.

Aspect 41. A method for decreasing colonization in a subject, the method comprising:

administering an effective amount of a composition comprising a comprising a mature Pn3Pase protein having P3nPase activity to a subject colonized by or at risk of being colonized by a serotype 3 *S. pneumoniae*.

Aspect 42. The method of any one of Aspects 39-41 wherein the protein comprises an amino acid sequence having at least 80% identity with an amino acid sequence selected from SEQ ID NO:2, wherein the amino terminal amino acid is selected from any one of residues 2 to 64 of SEQ ID NO:2 and the carboxy terminal amino acid is residue 1545 of SEQ ID NO:2.

Aspect 43. The method of any one of Aspects 39-42 wherein the protein comprises an amino acid sequence having at least 80% identity with amino acids 41-1545 of SEQ ID NO:2.

Aspect 44. The method of any one of Aspects 39-43 wherein the subject is a human.

Aspect 45. A mature Pn3Pase protein disclosed herein for use in therapy.

Aspect 46. A mature Pn3Pase protein disclosed herein for use as a medicament.

Aspect 47. A mature Pn3Pase protein disclosed herein for use in the treatment of a condition.

Aspect 48. Use of a mature Pn3Pase protein disclosed herein for preparation of a medicament for the treatment of pneumonia, pneumococcal meningitis, otitis media, bacteremia, sepsis, or a combination thereof.

Aspect 49. The composition comprising a mature P3nPase protein described herein for use in treating or preventing an infection or a symptom caused by a serotype 3 *S. pneumoniae*.

Aspect 50. A protein, composition, or method including one or more features described herein.

EXAMPLES

The present invention is illustrated by the following examples. It is to be understood that the particular examples, materials, amounts, and procedures are to be interpreted broadly in accordance with the scope and spirit of the invention as set forth herein.

Example 1

Identification of the *Streptococcus pneumoniae* Type 3 Capsule-Specific Glycosyl Hydrolase Gene of *Paenibacillus* sp. 32352

Abstract

'*Bacillus circulans* Jordan 32352' was isolated from decaying organic matter in the New Jersey soil in the early 1930s. This soil-dwelling bacterium produced an enzyme capable of degrading the type 3 capsular polysaccharide (Pn3P) of *Streptococcus pneumoniae* (Spn). Early reports of this enzyme (Pn3Pase) demonstrated its inducibility by, and specificity for Pn3P. A number of studies since have employed Pn3Pase while investigating Pn3P biosynthesis and its antigenic properties. We set out to clone this enzyme for recombinant expression. We first sequenced the genome of this bacterial species and reclassified the Pn3Pase producing bacterium as "*Paenibacillus* sp. 32352". Here, we identified the gene of Pn3Pase through mass spectrometry-based proteomics. We cloned the gene for recombinant expression and characterized the oligosaccharide products generated upon the enzymatic depolymerization of Pn3P. We examined the effects of Pn3Pase on live, growing type 3 Spn, so that it may be investigated as a potential therapeutic agent against this hypervirulent serotype of Spn.

In 1930, Avery and Dubos isolated an organism from soil taken from cranberry bogs, which was capable of depolymerizing type 3 capsular polysaccharide of *Streptococcus pneumoniae* (Pn3P), a linear polymer of −3)βGlcA(1-4) βGlc(1-(1,2). The expression of this enzyme (Pn3Pase) was inducible in the presence of Pn3P, and the bacterium was able to grow with Pn3P as the sole carbon source. They described this bacterium as a sporulating, gram-negative, aerobic *bacillus* with peritrichous flagella. A few years later, Sickles and Shaw isolated two additional similar strains demonstrating the same enzymatic activity targeting Pn3P (3,4). These strains were designated as *Bacillus palustris*, before being accepted as synonymous to *Bacillus circulans* (4-6). Besides Pn3Pase, these strains demonstrated the ability to produce enzymes capable of depolymerizing *S. pneumoniae* capsular serotypes 2 and 8, although soluble protein in cell free extracts were inactive against these polysaccharides (3,7). There are numerous possible practical applications for these strains and enzymes. For example, investigators have applied the Sickles and Shaw Pn3Pase enzyme while examining Pn3P biosynthesis as well as its antigenic and immunological properties (8-11).

We obtained the '*Bacillus Circulans* Jordan strain 32352' (i.e., the Sickles and Shaw strain) from American Type Culture Collection, and sequenced its genome (12). 16S rRNA analysis revealed that this bacterium belonged in the Paenibacillae genus, and it is now identified as *Paenibacillus* sp. 32352 (Pbac). *Paenibacillus* species are of growing interest since the genus was established in 1991 (13). These microbes are a rich source of extracellular enzymes that catalyze a variety of reactions, which have demonstrated utility in numerous agricultural and medical applications (14-19). Database for carbohydrate-active enzyme annotation (dbCAN) of the *Paenibacillus* sp. 32352 genome indicates 665 carbohydrate active entries out of 7200 predicted genes, 252 of those exhibiting glycosyl hydrolase- or polysaccharide lyase-like architecture (20).

We set out to determine the identity of the gene producing Pn3Pase in order to express and utilize the enzyme's unique Pn3P-specific activity. We postulated the potential use of this enzyme as a therapeutic agent for serotype 3 *S. pneumoniae* infections. The capsular polysaccharide (CPS) is a major virulence factor for type 3 strains, as non-encapsulated mutants fail to colonize (21). The virulence mechanisms of CPS is to help Spn evade the immune system through resisting or inhibiting its phagocytosis by host macrophages while also limiting mucus-mediated clearance (22). The Pn3P component of the current 13-valent vaccine (PCV13) induces variable immune responses to serotype 3 (23,24). Individuals vaccinated with PCV13 require higher opsonophagocytosis assay serum titers for serotype 3 in comparison with other serotypes (25). Despite current vaccination programs against Spn, it remains one of the world's most lethal pathogens. In addition to vaccination and antibiotic delivery, alternative therapeutic approaches must be considered for fighting these and other encapsulated pathogens.

Described here is the identification of the *Paenibacillus* Pn3Pase through proteomics of culture supernatant preparations with Pn3P supplemented minimal media growth. We have cloned the Pn3Pase gene and expressed active enzyme in *E. coli*. We have characterized oligosaccharide products, and optimized conditions for Pn3P depolymerization. We assessed the ability of the enzyme to degrade the capsule on a live virulent type 3 Spn strain to begin investigating Pn3Pase as a potential therapeutic agent.

Results

Pn3P Utilization Induces Expression of Genes Organized into Locus

Figure 3B:
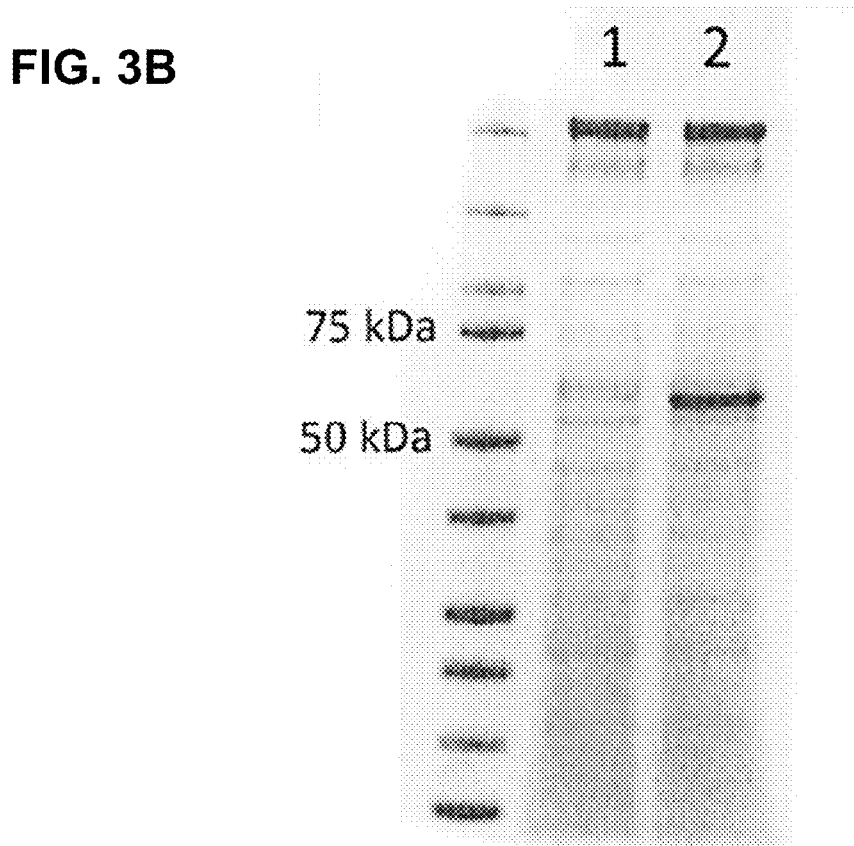
Figure 3C:
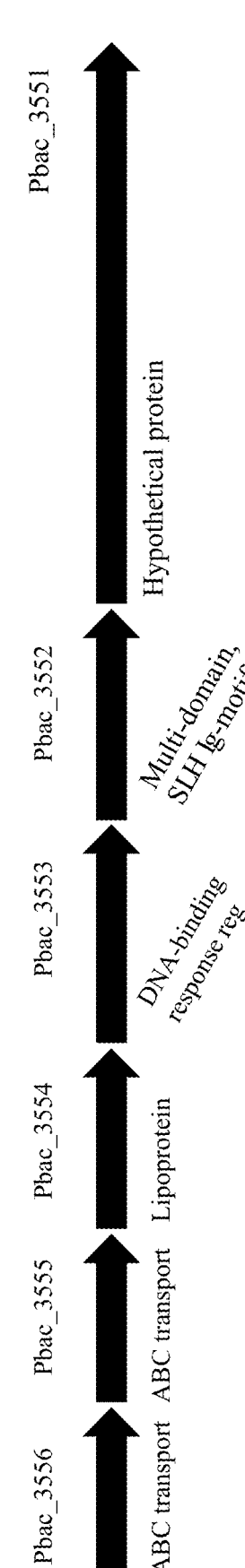
Figure 3D:
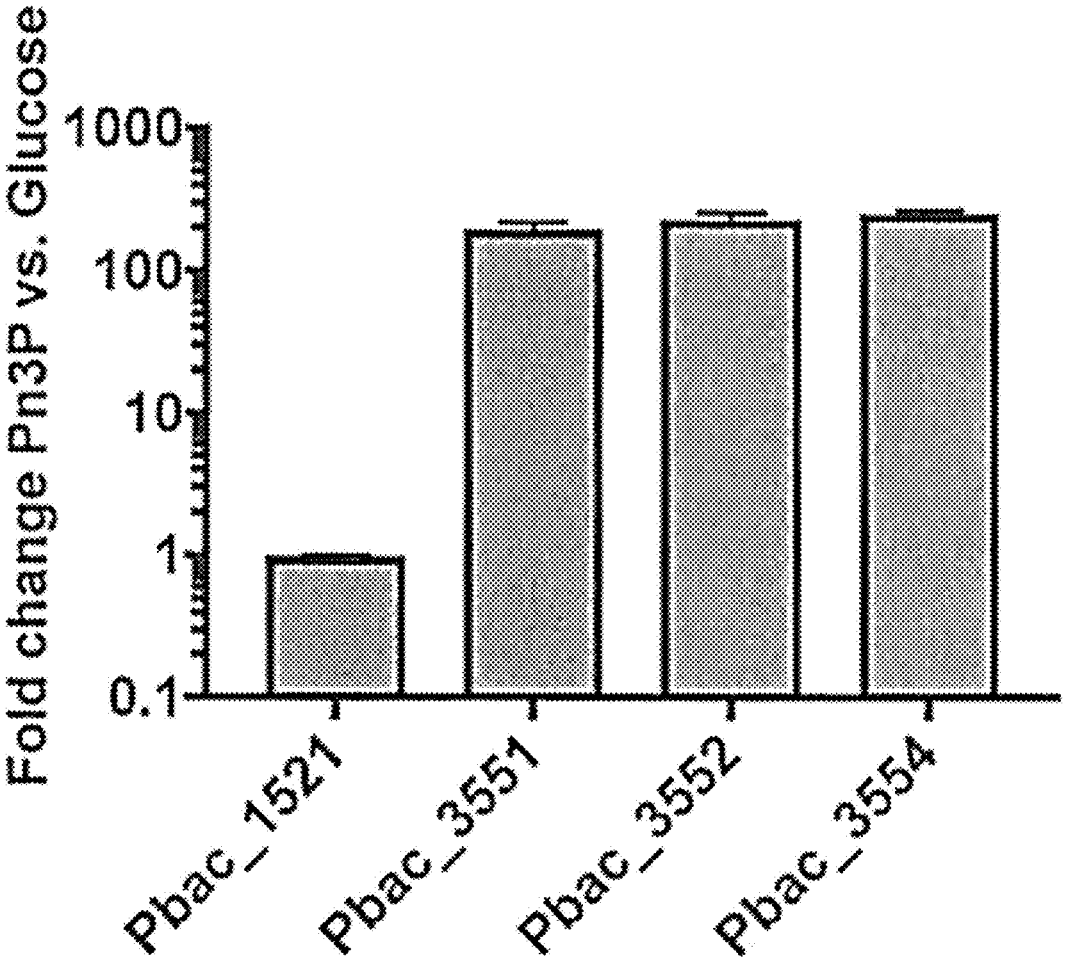

We began by culturing Pbac in minimal M9 media with either 2% glucose or Pn3P as the sole carbon source. Pbac growth was monitored for 14 h by OD 600 nm to achieve maximum Pn3Pase production, (FIG. 3A). Pbac was able to grow and utilize Pn3P and glucose, but was unable to utilize cellulose. Supernatants from these cultures were concentrated 20×, and proteins were visualized by coomassie staining. In the Pn3P growth conditions a prominent band ~55 kDa was observed (FIG. 3B). Proteomic analysis of these samples by in-solution trypsin digestion and LC-MS identified numerous proteins that were present in both samples. Two proteins, however, were significantly enriched in the Pn3P growth condition as highlighted in Table 1.

protein (Pbac_3551). Since two of these proteins are more abundant in the Pn3P growth conditions, we compared the transcription of three genes of this locus with the commonly expressed surface layer protein (Pbac_1521) in the glucose and Pn3P samples by RT-PCR. The transcription of genes 3551, 3552, and 3554 increase ~130-fold with Pn3P utilization, while mRNA expression of Pbac_1521 is unchanged between the two conditions (FIG. 3D).

Pn3Pase Identification and Domain Analysis

Figure 4B:
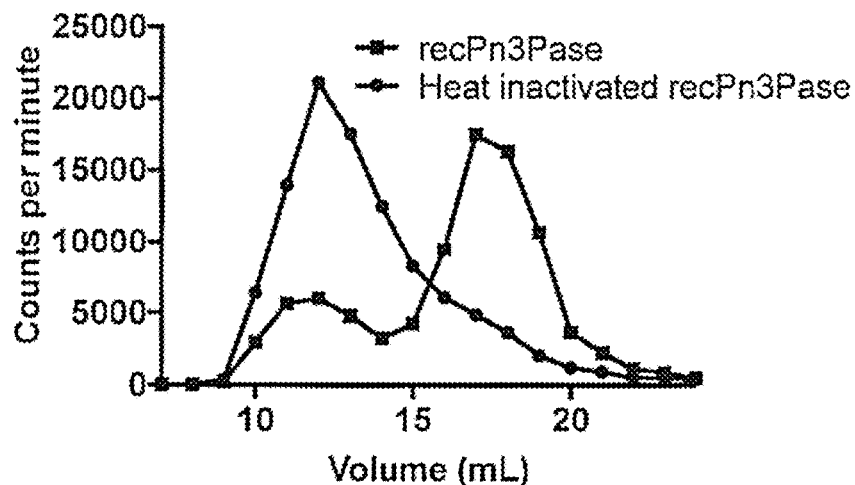
Figure 4C:
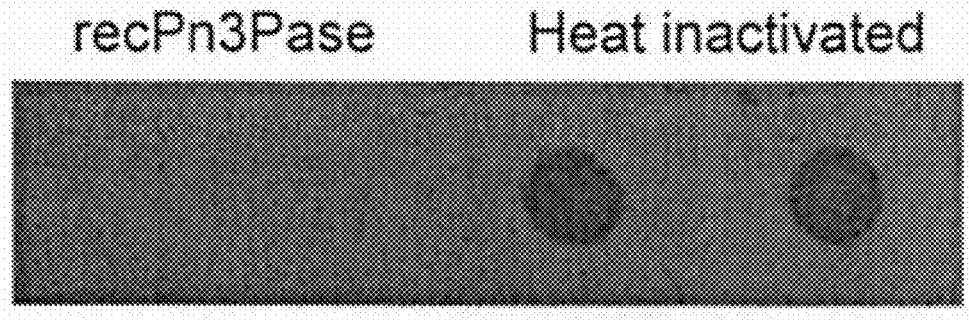

Pbac_3554, Pbac_3552, and Pbac_3551 were cloned and expressed in *E. coli* BL21 (DE3) cells to determine which upregulated gene product was responsible for Pn3P depolymerase activity. The hypothetical protein Pbac_3551 (Accession WP_079915027), with primary amino acid sequence shown in FIG. 4A, demonstrated rapid and efficient hydrolysis of tritium radio-isotope labeled Pn3P, as shown by counts per minute shift to lower molecular weight oligosaccharides when reaction products were separated by size exclusion chromatography (FIG. 4B). Reactions of recombinant Pn3Pase with unlabeled Pn3P were performed, spotted on a PVDF membrane, and probed with a Pn3P monoclonal antibody. Reactivity to the monoclonal antibody was completely abolished after 4 h Pn3Pase treatment of Pn3P (FIG. 4C).

Figure 4D:
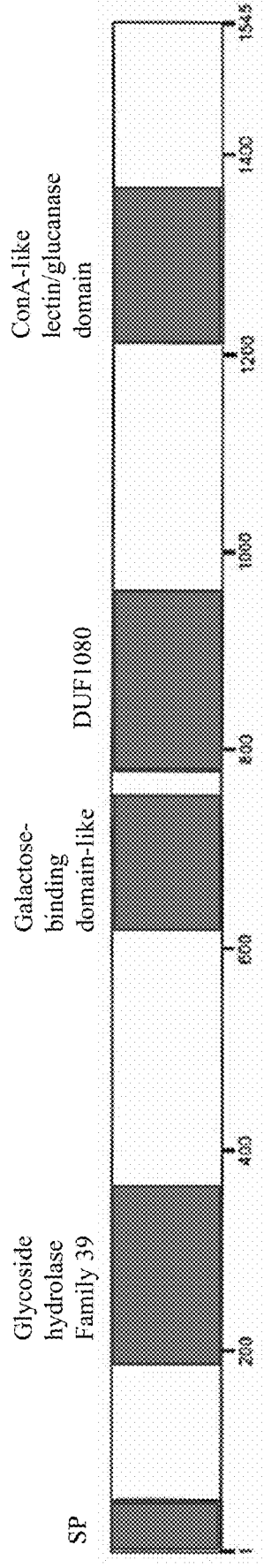

The translated protein sequence of Pbac_3551 is 1,545 amino acids. Predicted cleavage of the signal peptide by SignalP 4.1 server (26) from residues 1-40 would yield a mature protein of 164.1 kDa. Protein sequence analysis and classification by InterPro online software (27) recognized homology to glycoside hydrolase, family 39 from amino acids 180-353, galactose-binding domain-like from 621-765, a domain of unknown function DUF1080 from 781-950 with structural similarity to an endo-1,3-1,4-beta glucanase, and a concanavalin A-like lectin/glucanase domain from 1,209-1,348 (FIG. 4D). Although segments of this enzyme display some homology to numerous carbohydrate active proteins, no overall homology to known glycosyl hydrolase families across the length of the enzyme exist.

Characterization of Oligosaccharide Products

The oligosaccharide products of Pn3Pase hydrolysis were separated by size exclusion chromatography. This hydroly-

TABLE 1

Proteomic identification of culture supernatant proteins of *Paenibacillus* sp. 32352 grown in Pn3P. Highlighted are proteins unique to Pn3P grown culture.

| Gene | Description | Score | Coverage | # Unique Peptides | # PSMs | # AAs | MW [kDa] |
|---|---|---|---|---|---|---|---|
| Pbac_3554 | *Lipoprotein | 1301.24 | 82.02 | 49 | 597 | 506 | 55.9 |
| Pbac_1521 | Ig-like, group 2, Surface layer protein | 450.46 | 50.17 | 44 | 218 | 1190 | 128.7 |
| Pbac_6539 | Hypothetical protein | 237.19 | 31.20 | 17 | 82 | 577 | 64.1 |
| Pbac_5871 | NLP/P60 family protein | 103.53 | 61.54 | 6 | 35 | 156 | 16.9 |
| Pbac_1659 | Alpha/beta hydrolase fold (EC 3.8.1.5) | 94.98 | 66.07 | 13 | 72 | 280 | 30.1 |
| Pbac_3551 | Hypothetical protein NCBI ref seq: WP_079915027 | 39.14 | 16.70 | 6 | 53 | 1545 | 168.0 |

Figure 5A:
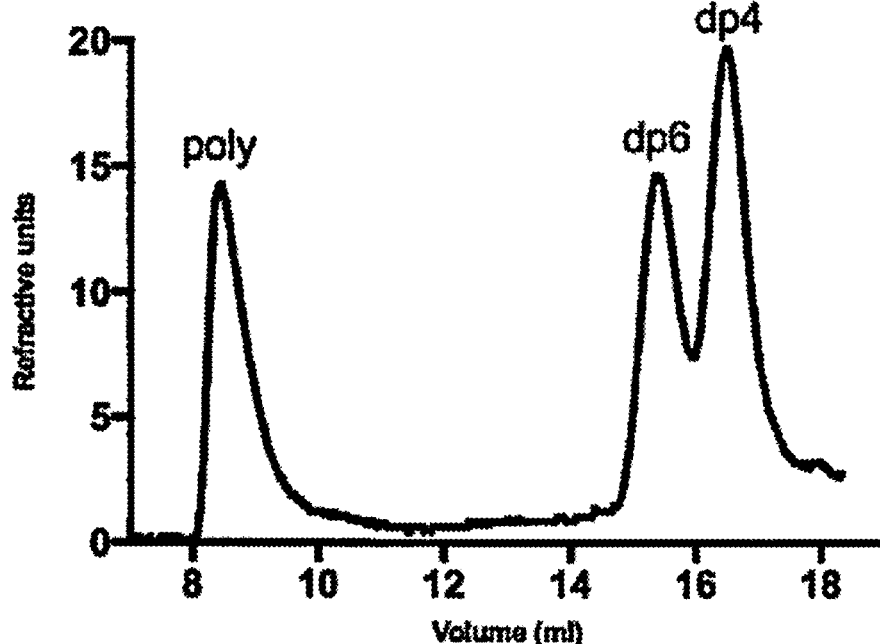
FIGS. 5A-5C show identification of oligosaccharide products by electrospray ionization mass spectrometry. Separation of oligosaccharide products (FIG. 5A) and mass spectra of the tetrasaccharide (FIG. 5B) and the hexasaccharide (FIG. 5C). Experimental molecular weights and the accuracies are shown in Table 1.
Figure 5B:
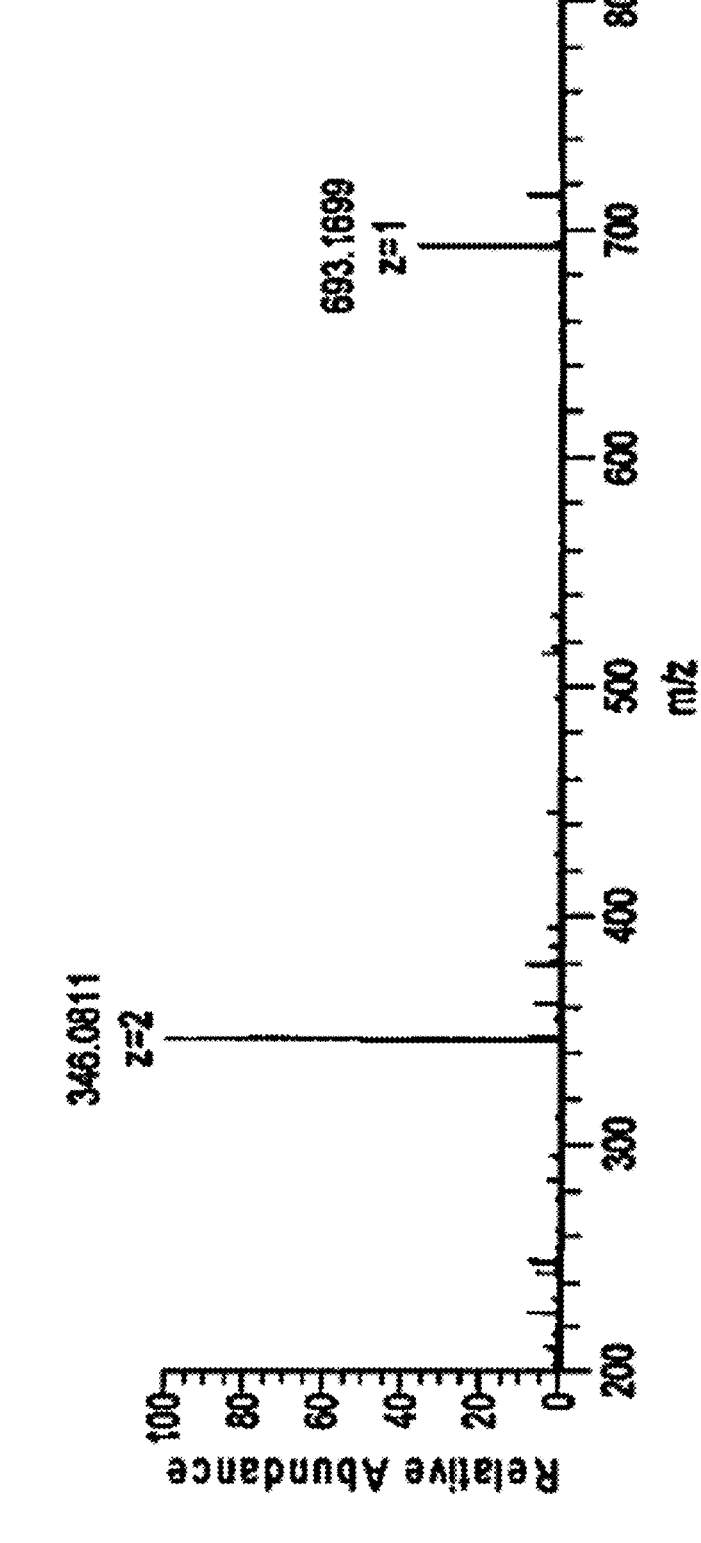
Figure 5C:
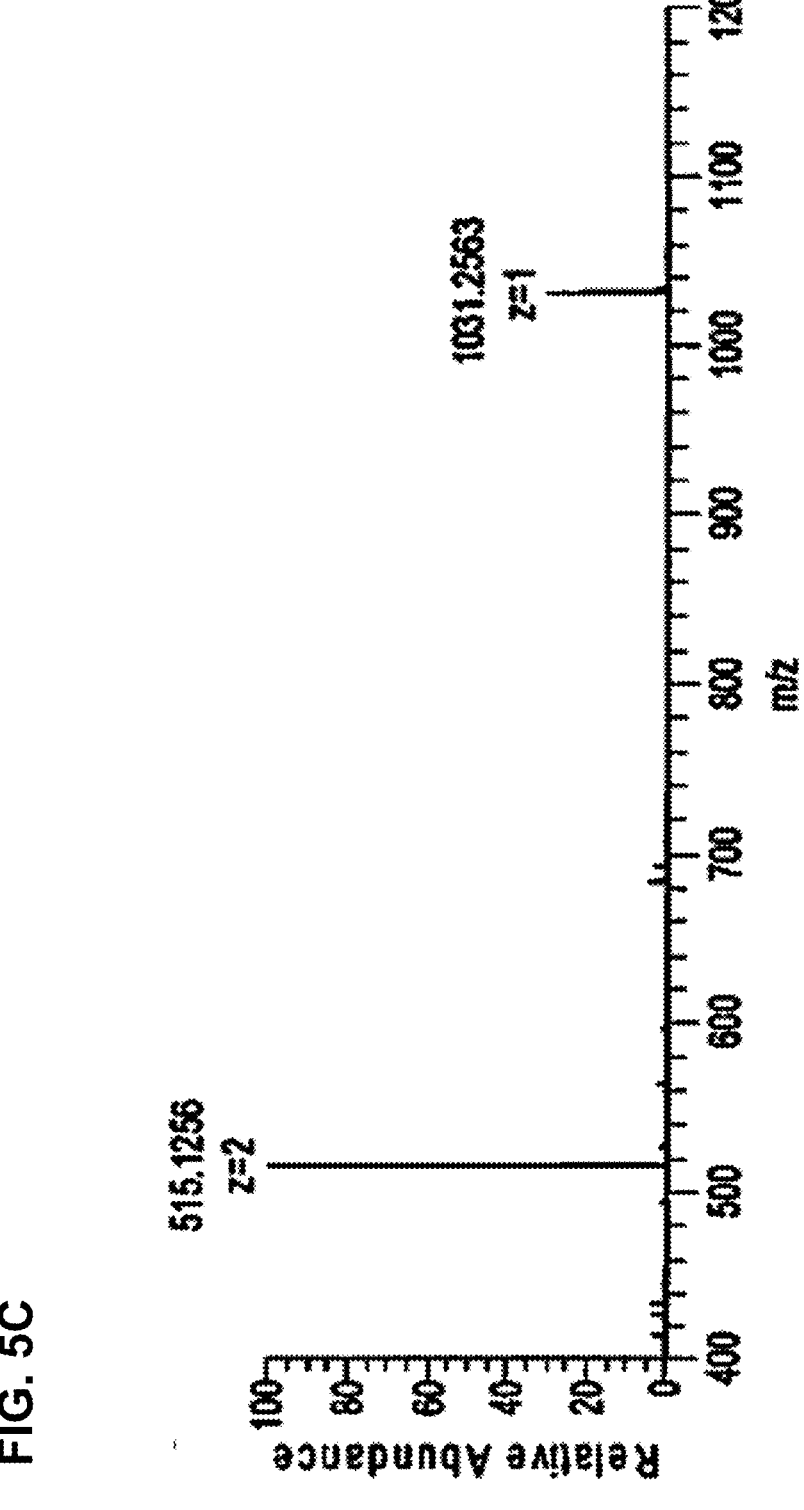
Figure 6A:
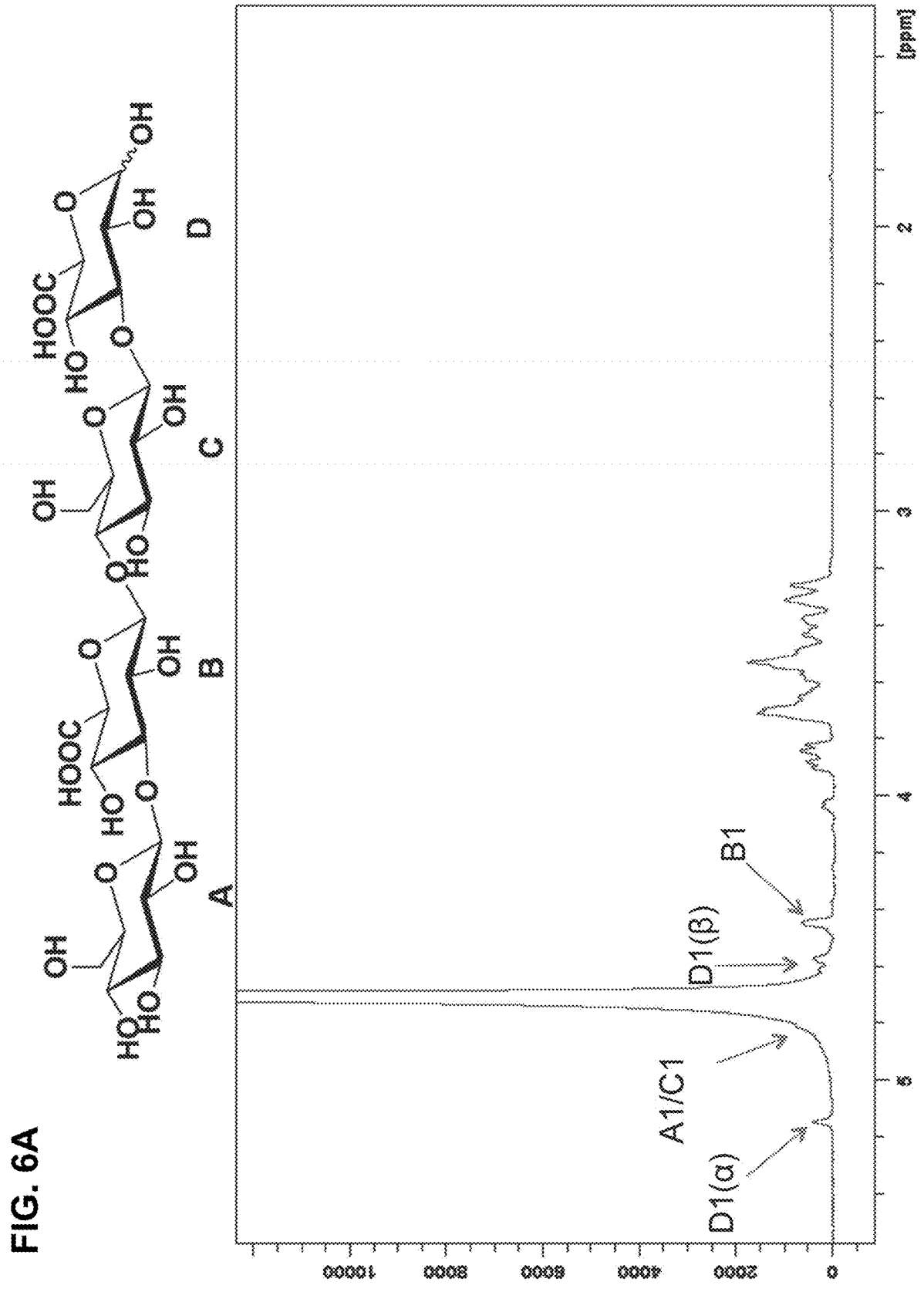
FIGS. 6A-6F show Nuclear Magnetic Resonance characterization of oligosaccharide products. 1H NMR spectrum (FIG. 6A), 2D HSQC NMR spectrum (FIG. 6B), and 2D COSY NMR spectrum (FIG. 6C) of the Pn3 tetrasaccharide. 1H NMR spectrum (FIG. 6D), 2D HSQC NMR spectrum (FIG. 6E), and 2D COSY NMR spectrum (FIG. 6F) of the Pn3 hexasaccharide.
Figure 6B:
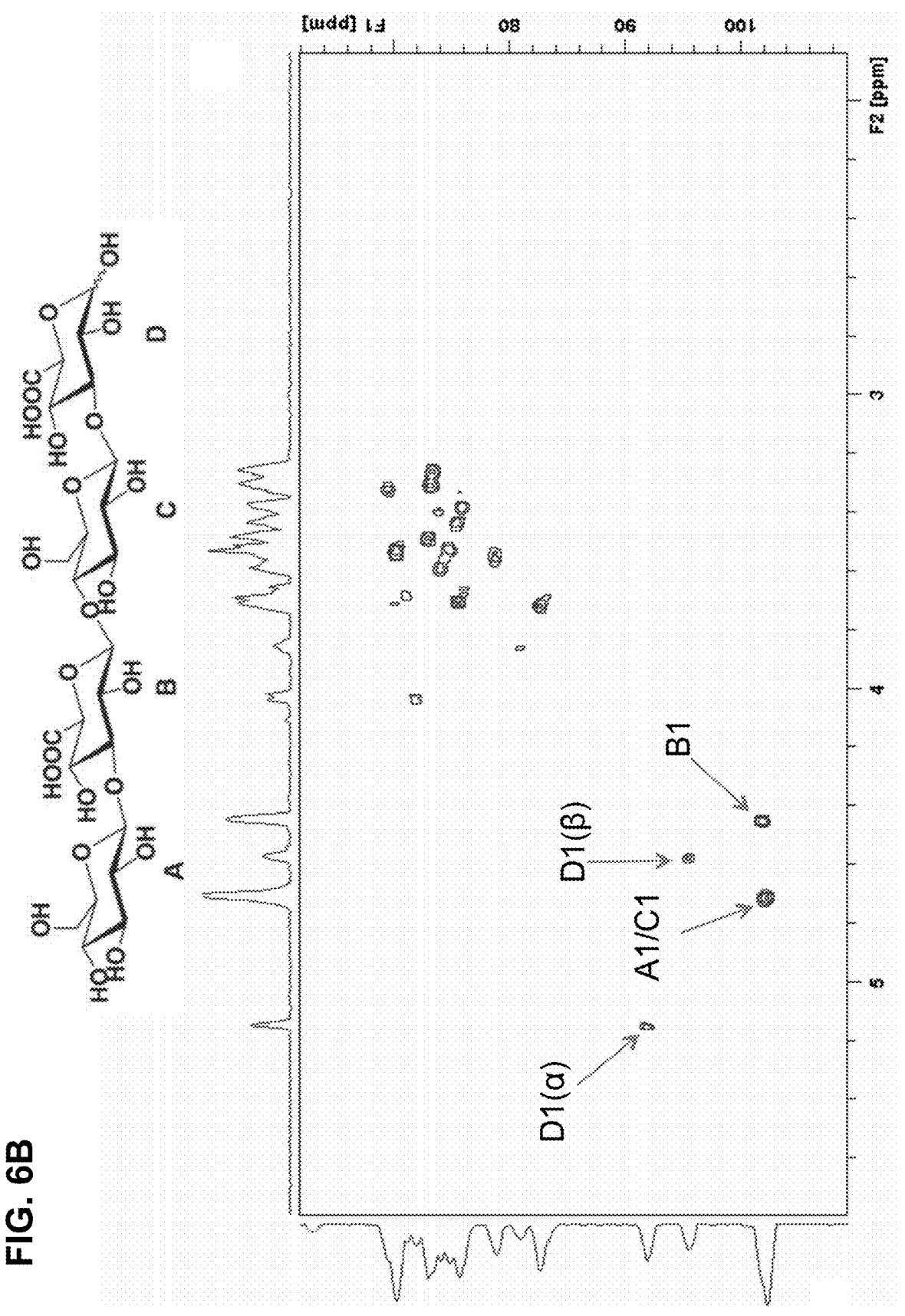
Figure 6C:
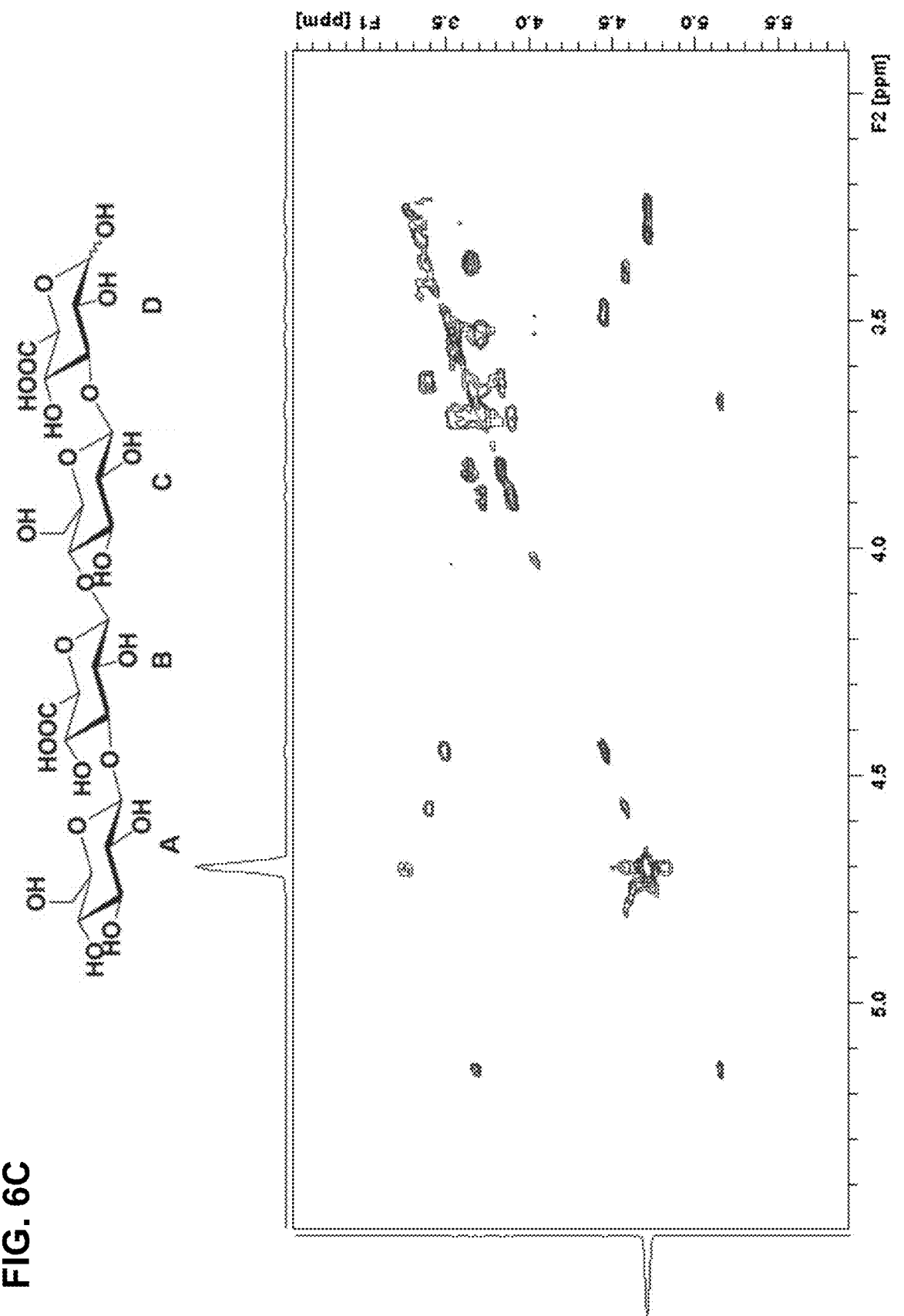
Figure 6D:
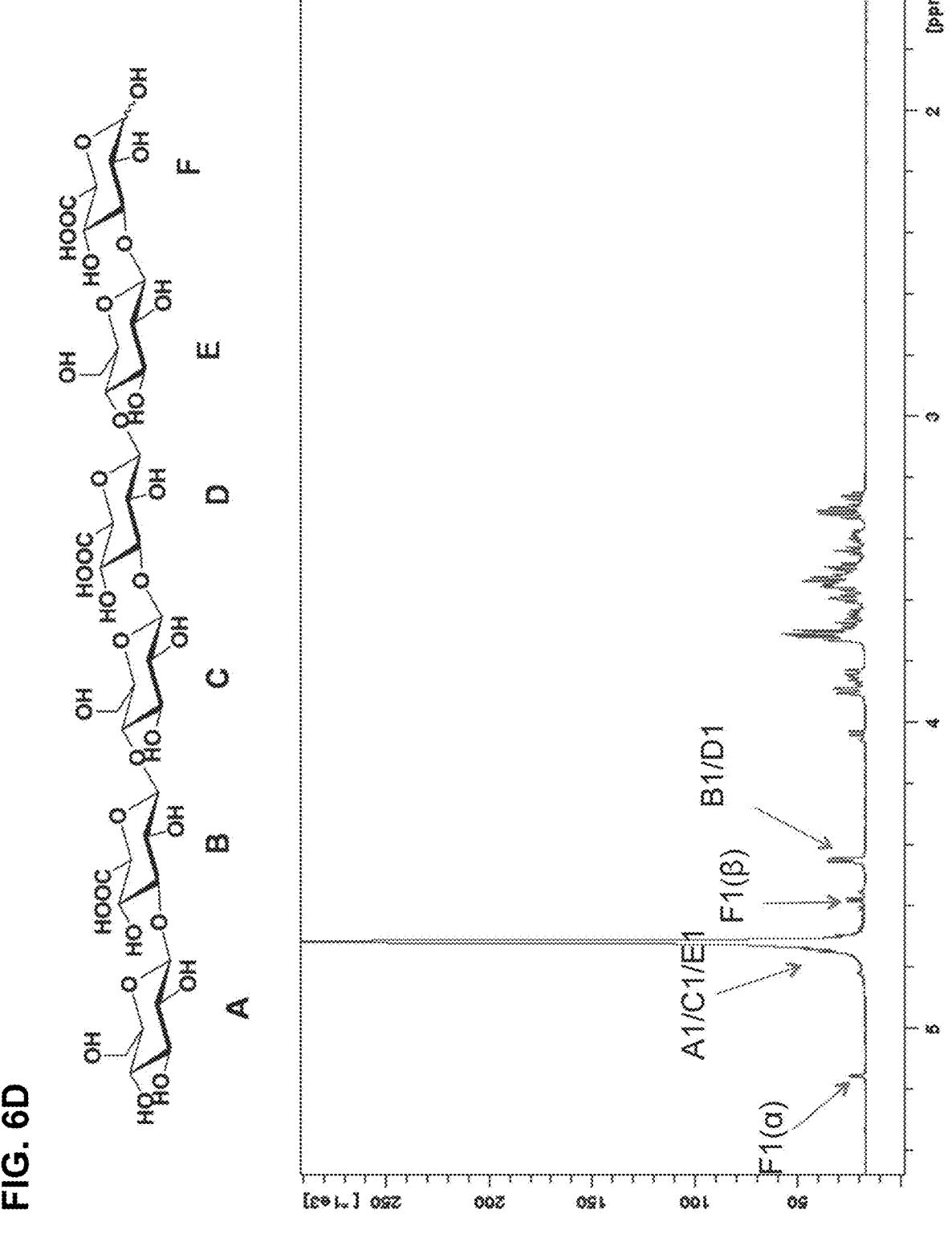
Figure 6E:
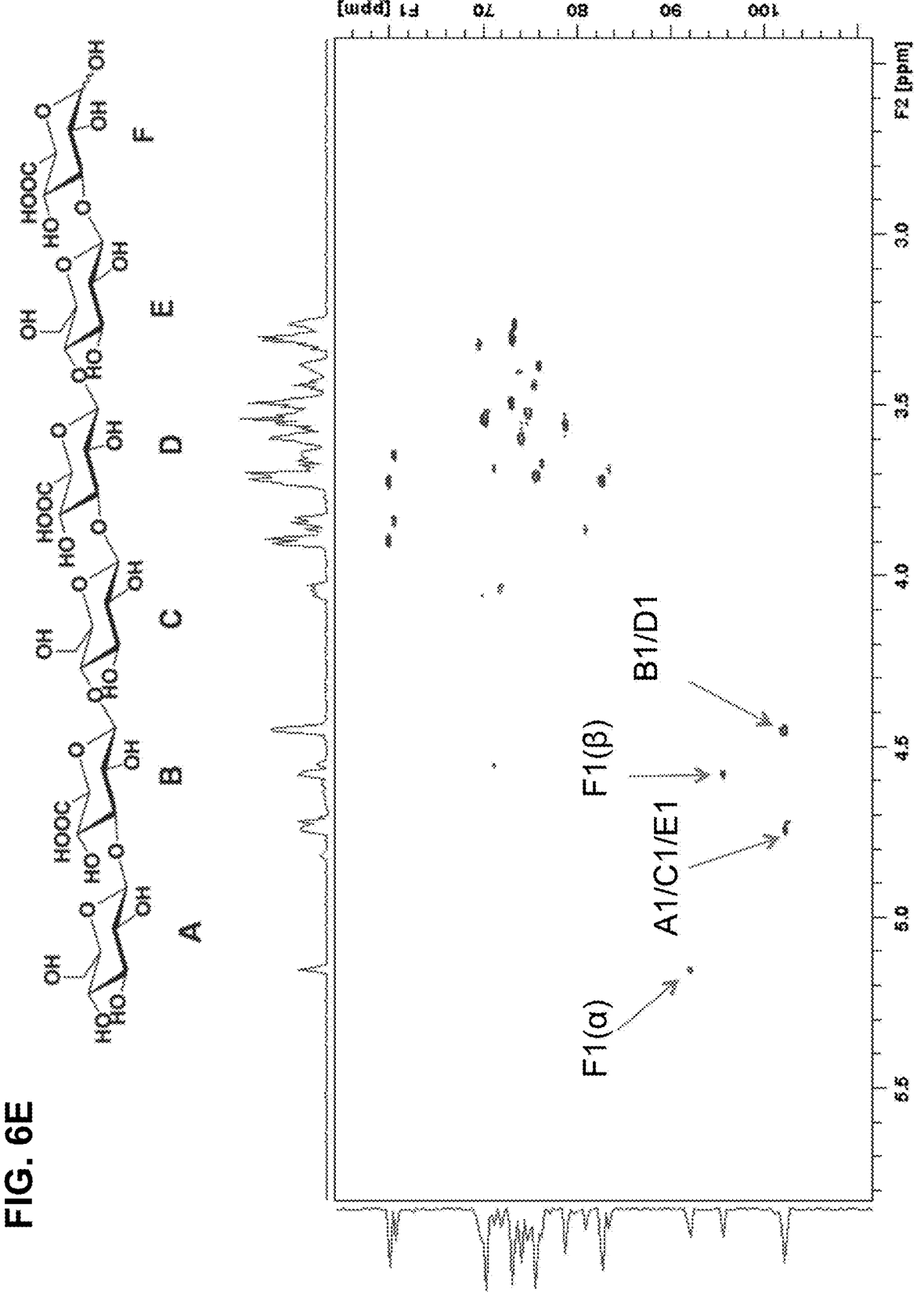
Figure 6F:
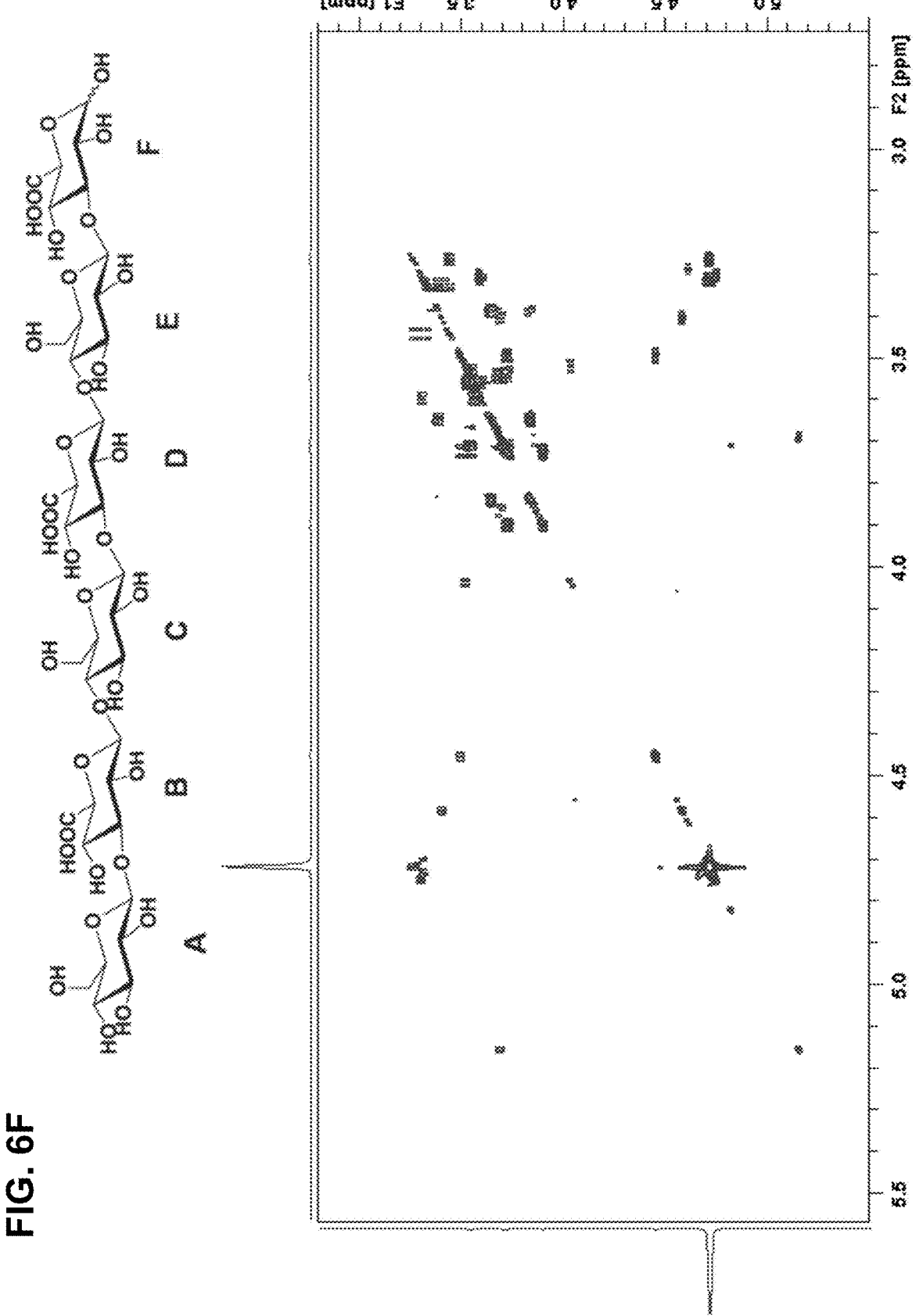

These two Pn3P induced Pbac proteins appear to be organized into a locus of Pn3P utilization (FIG. 3C) consisting of ABC-type polysaccharide transport system, permease component (Pbac_3556), probable ABC transporter permease protein ytcP (Pbac_3555), lipoprotein (Pbac_3554), DNA-binding response regulator, AraC family (Pbac_3553), multidomain protein with s-layer homology region, glug motif, ig motif (Pbac_3552), and hypothetical sis yielded two major product peaks eluting late in the Superdex peptide column corresponding to a tetrasaccharide and hexasaccharide (FIGS. 5A-C). The identities of these peaks were confirmed as tetrasaccharide (FIG. 5B) and hexasaccharide (FIG. 5C) by electrospray ionization mass spectrometry. Mass spectrometry data is summarized in Table 2.

TABLE 2

Different charge states of the tetrasaccharide and hexasaccharide detected by mass spectrometry.

|  | m/z observed | Charge state | Experimental M | Theoretical M | Error (ppm) |
|---|---|---|---|---|---|
| Tetrasaccharide | 693.1699 | 1 | 694.1777 | 694.1804 | −3.85 |
|  | 346.0811 | 2 | 694.1779 | 694.1804 | −3.66 |
| Hexasaccharide | 1031.2563 | 1 | 1032.2641 | 1032.2653 | −1.13 |
|  | 515.1256 | 2 | 1032.2669 | 1032.2653 | 1.51 |

The characterization of oligosaccharide products by NMR spectroscopy is presented in FIG. 6. All anomeric proton signals are assigned in representative $^1$H NMR spectra of tetra- and hexa-saccharides (FIG. 6). Anomeric proton signals of residue A, C and E at ~4.70 ppm were overlapped with HOD peak (FIGS. 6A, 4D) but showed up in 2D HSQC spectrum (FIGS. 6B, E). The $^3J_{HH}$ coupling constants of B-1 and D-1 were 8.22 Hz, demonstrating β-linkages. The signals at 5.15 ($^3J_{HH}$=3.69) and 4.58 ($^3J_{HH}$=8.05) ppm correspond to α- and β-configuration of GlcA residue F, respectively. By combining HSQC and COSY experiments (FIGS. 6C, F), we were able to identify that proton signal of F-5 possessed a high chemical shift (~4.05 ppm) suggesting that GlcA residue (F) was at the reducing end of the carbohydrate chain. These data demonstrate that Pn3Pase cleaves the β(1-4) linkage between glucuronic acid and glucose in the polysaccharide chain.

Pn3Pase Activity Analysis

Figure 7A:
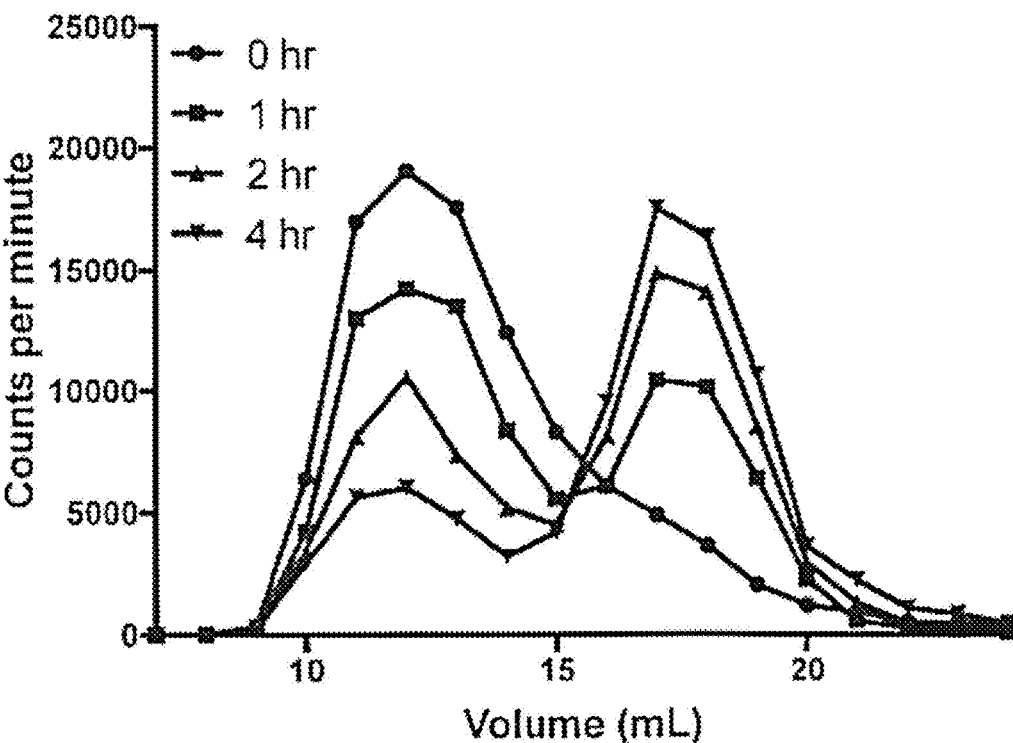
FIGS. 7A-7C show activity assessment of Pn3Pase.

A time course experiment was performed using tritiated Pn3P and the recombinant Pn3Pase to understand whether this enzymatic degradation proceeds through endolytic or exolytic cleavage. Reaction products were separated by size exclusion chromatography after proceeding for the given time. Low molecular weight oligosaccharides are generated early on in the reaction (FIG. 7A). Both an increase in CPM for the oligosaccharide elution volume, and corresponding decrease in CPM for the higher molecular weight polymer over time suggest an exolytic type cleavage (FIG. 7A) that preferentially generates tetrasaccharides and hexasaccharides (FIG. 5A). A gradual shift of the peak from left to right over time would be indicative of true random endolytic cleavage.

Figure 7B:
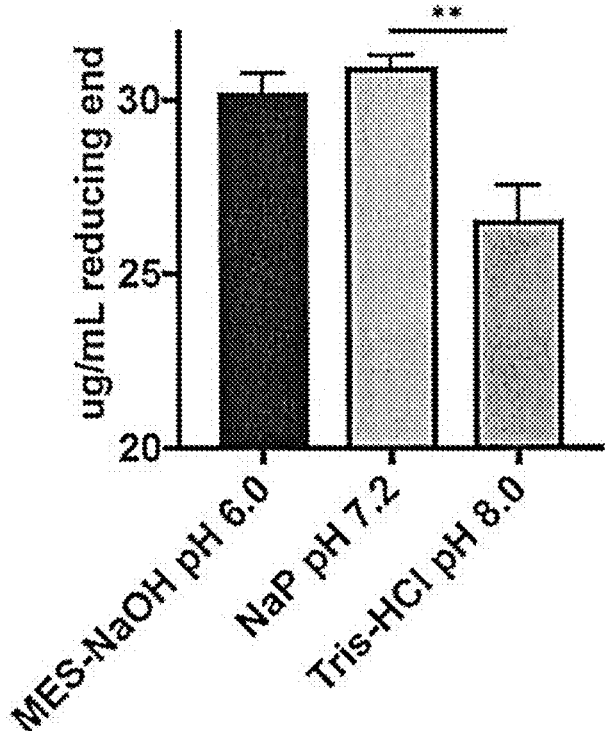
Figure 7C:
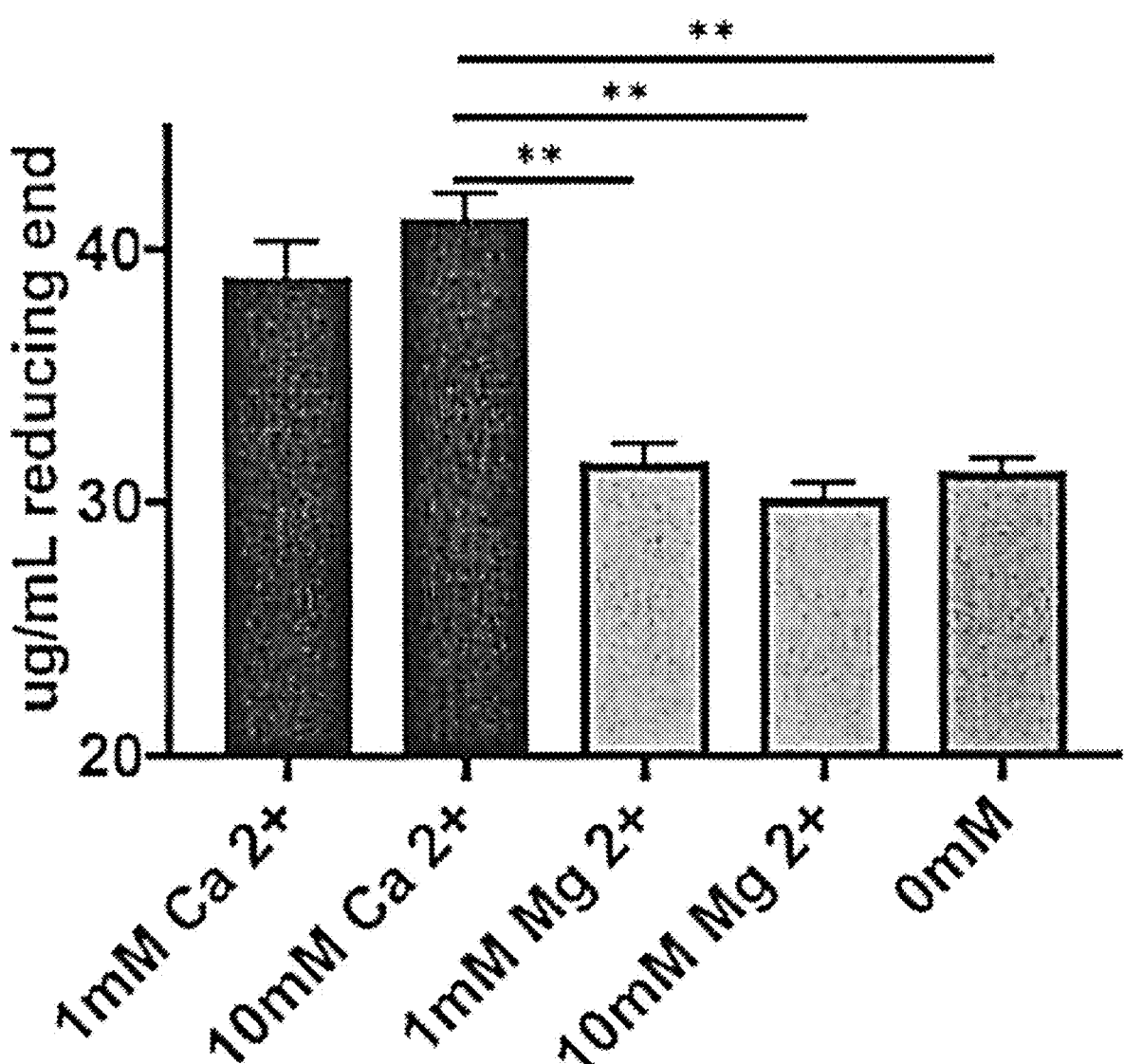

Two-hour reactions were performed in three different buffers at pH 6.0, 7.2, and 8.0, detecting the concentration of reducing end glucuronic acid by the p-hydroxybenzoic acid hydrazide (PAHBAH) method (43) to determine the optimum reaction conditions for Pn3Pase. Pn3Pase displays slightly better activity in sodium phosphate buffer at pH 7.2 than in MES buffer pH 6.0, but performs significantly worse in Tris buffer at pH 8.0 in Tris buffer pH 8.0 (FIG. 7B). Further optimization focusing on metal-ion dependence was performed with Mg$^{2+}$ and Ca$^{2+}$. Pn3Pase displays a concentration-dependent preference for Ca$^{2+}$, as it produces a higher concentration of reducing end GlcA in presence of 10 mM Ca$^{2+}$ (FIG. 7C).

Pn3Pase Removes Capsule from Growing Type 3 *Streptococcus pneumoniae*

Figures 8A, 8B, 8C, 8D:
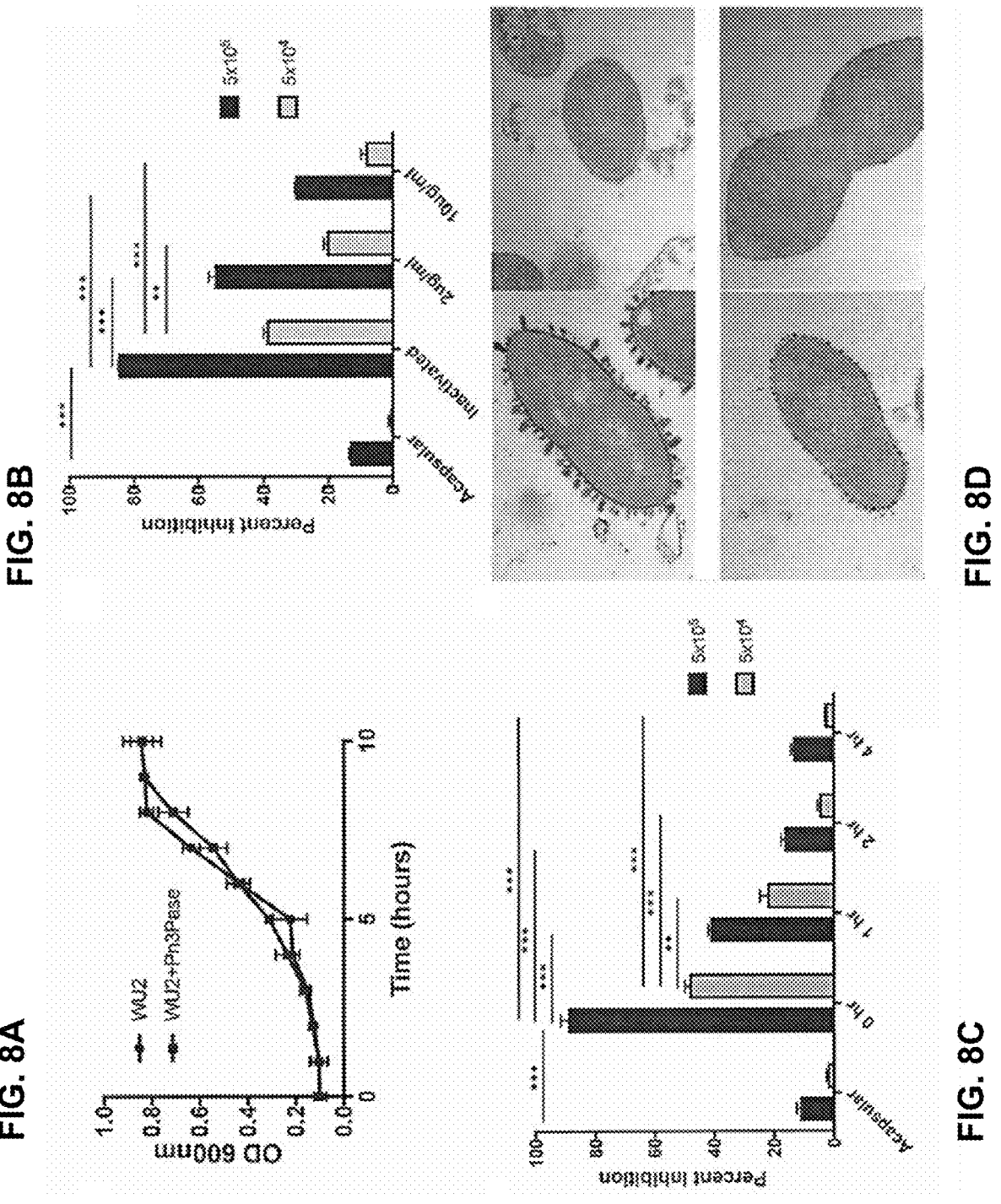
FIGS. 8A-8D show Pn3Pase treatment of live, growing type 3 *Streptococcus pneumoniae* WU2 strain.

The type 3 WU2 strain was cultured for 10 h with 100 µg/ml of the recombinant enzyme added to the growth medium to begin assessing effects of Pn3Pase treatment of growing type 3 *S. pneumoniae*. Pn3Pase treatment of cells demonstrated no adverse growth or cytotoxic effects on the bacterial growth as indicated in FIG. 8A. Additionally, comparable CFU values were obtained at two-hour intervals (data not shown).

The bacterial cells grown in the presence of 2 µg/ml or 10 µg/ml Pn3Pase were then examined by competition ELISA to determine if the enzyme led to efficient capsule shedding of the growing cultures. After treatment, fixed whole cells, at different concentrations, were used to compete for Pn3P specific antibodies binding to the Pn3P coated plate. The acapsular WU2 mutant strain (JD908) showed minimal inhibition at 5×10$^5$ CFU/ml and no inhibition at 5×10$^4$ CFU/mL concentration, due to its lack of capsule (FIG. 8B). Heat inactivated Pn3Pase treated cells demonstrated the highest inhibition percent as cell surfaces should be fully decorated with CPS (FIG. 8B) With active Pn3Pase treatment, inhibition of antibody binding begins to decrease in a Pn3Pase concentration dependent manner (FIG. 8B), suggesting that the enzyme is well-designed to strip the capsule from live, growing type 3 *Streptococcus pneumoniae*.

A time course experiment was performed in which the bacterial cells were grown to mid-log phase, suspended in PBS, and treated with 1 µg/ml Pn3Pase for 0, 1, 2, or 4 hours. The Pn3Pase dose was lowered for this experiment given that the WU2 strain should not be actively growing and producing a substantial amount of new CPS under these conditions. The enzymatic activity of the Pn3Pase is also slightly better in PBS than in the THY culture media (data not shown). At the given time point, the treated cells were fixed and examined by competition ELISA as described above. The acapsular WU2 mutant strain (JD908), again, showed minimal inhibition at 5×10$^5$ CFU/ml and no inhibition at 5×10$^4$ CFU/mL concentration, due to its lack of capsule (FIG. 8C). Untreated cells exhibited the highest inhibition percent, indicative of a cell surface fully decorated with CPS (FIG. 8C) With increasing Pn3Pase incubation time, inhibition of antibody binding begins to decrease significantly (FIG. 8C), appearing essentially acapsular after 2 and 4 hour treatment.

The Pn3Pase treated cells were visualized by transmission electron microscopy and compared to both untreated and an acapsular mutant strain. The untreated cells displayed a thick, complete CPS coat across their surface (FIG. 8D upper left). As expected, the acapsular mutant had no CPS (FIG. 8D upper right). The capsule layer of the enzyme treated cells exhibited minimal thickness in most cases (FIG. 8D bottom left), while some looked as though they were acapsular (FIG. 8D bottom right).

Discussion

The *Paenibacillus* genus, literal Latin translation, "almost *Bacillus*," was ruled distinct from true *Bacillus* species when phylogenetic analysis on 16S rRNA gene sequences was performed for a number of strains previously defined as *Bacillus* (6). Sequence analysis showed that several bacterial strains sorted into this genus, required reassignment. Species belonging to this genus have been obtained from diverse ecological niches (28) from aquatic (29) to desert environments (30), and from hot springs (31) to extreme cold regions (32). Many *Paenibacillus* species are found in soil (3,33) and plant root environments (34), however, a number are isolated from human samples as well (35). *Paenibacillus* species are a rich source for a variety of agricultural, biomedical, and industrial products (28). Extracellular enzymes demonstrating numerous activities (36) have applications in production of a variety of industrially significant materials (28). A number of these species are efficient nitrogen fixers that have been applied agriculturally to promote crop growth (37). In addition, protective action of novel antimicrobial peptides and compounds obtained from Paenibacilli has been demonstrated (38).

While *Paenibacillus* sp. 32352 was isolated from a soil source (3), it is appropriate to question the evolutionary pressure to obtain enzymes capable of acting on a human pathogen Spn CPS. Based on earlier studies, this particular strain demonstrates the ability to degrade three distinct pneumococcal CPSs (3,9). Whether these are the natural substrates for the enzymes, or whether other soil dwelling microbes or plant matter possess similar glycan residues and linkages remains to be investigated.

However originally acquired, *Paenibacillus* sp. 32352 has adapted the Pn3Pase described here to play an important functional role in its metabolism. Early reports by Torriani and Pappenheimer on this species indicated the ability to induce Pn3Pase activity in culture supernatant by addition of Pn3P in the growth medium (7). The "inducibility" was in contrast to the Avery and Dubose findings that Pn3Pase formation only occurred in conditions where Pn3P is present as a sole carbon source(2). Here, we demonstrate that while Pn3P is not required for bacterial growth, it can serve as the sole nutrition source. Moreover, our data indicate that presence of Pn3P in the Pbac culture medium induces the expression of Pn3Pase.

Our attempts to purify multi-milligram quantities of active, native Pn3Pase from an induced culture of this strain were unsuccessful, though Pn3P depolymerizing activity can be detected in these culture supernatant preparations. In this study, we have identified and cloned the Pn3Pase gene from *Paenibacillus* sp. 32352. We have fully characterized the oligosaccharide products, and we have shown that Pn3Pase can rapidly strip the CPS from live, growing Spn. Future studies will assess this enzyme's utility as a treatment for serotype 3 Spn infections. Inefficiencies in current vaccination and antibiotic administration necessitate the discovery of alternative therapeutic approaches for controlling these and other encapsulated pathogens.

Experimental Procedures

Bacterial Strains and Growth Conditions

*Paenibacillus* sp. 32352 (ATCC 14175) was cultured aerobically with shaking at 37° C. on Tryptic Soy Agar with 5% sheep blood (Hardy Diagnostics), or in minimal medium (M9 Teknoba) culture containing 1 mM $MgSO_4$, 1 mM biotin, 1 mM thiamin, and 2% glucose (Sigma Aldrich) or Pn3P powder (ATCC 172-X) as sole carbon source. *Streptococcus pneumoniae* type 3 (WU2 strain) and acapsular derivative (JD908), generous gifts from Moon Nahm (University of Alabama at Birmingham), were cultured aerobically without shaking at 37° C. on Tryptic Soy Agar with 5% sheep blood (TSAB), or in Todd Hewitt Broth plus 0.5% yeast extract (THY) (BD Biosciences).

Proteomics of Culture Supernatants

*Paenibacillus* sp. 32352 was cultured in 5 ml of minimal medium M9 containing 2% (w/v) carbon source, as described above. Bacterial cultures were harvested at mid-log phase (OD600 nm 0.6). Culture supernatants were passed through a 0.45 μm syringe filter and concentrated to $\frac{1}{20}^{th}$ culture volume using a microsep advance centrifugal device with 10K molecular weight cutoff (Pall). Protein concentration was determined by bicinchoninic acid assay. An in-solution trypsin digestion was performed as described previously (39). Briefly, 20 μg protein from culture supernatant protein was reduced by incubation with 10 mM DTT for 1 h at 56° C., followed by carboxyamidomethylation with 55 mM iodoacetamide in the dark at room temperature for 45 min, and then digested with 1 Dg of sequencing grade trypsin (Promega) in 40 mM ammonium bicarbonate overnight at 37° C. trypsin digest was stopped by addition of 1% trifluoroacetic acid and incubation on ice for 30 minutes. The resulting peptides were cleaned up using C18 spin columns (G Biosciences), dried down, and reconstituted in 0.1% formic acid. The peptides were separated using a Thermo Scientific UltiMate 3000 system on a 15 cm Acclaim™ PepMap™ RSLC C18 Column (2 μm particle size, 75 μm ID) using a 180 min linear gradient consisting of 1-100% Solvent B (80% acetonitrile, 0.1% formic acid) over 130 min at a flow rate of 200 nL/min. Separated peptides were directly eluted into a nanospray ion source of an Orbitrap Fusion Tribrid mass spectrometer (Thermo Fisher Scientific). The stainless steel emitter spray voltage was set to 2200 V, and the temperature of the ion transfer tube was set to 280° C. Full MS scans were acquired using Orbitrap detection from m z 200 to 2000 at 60,000 resolution, and $MS^2$ scans following fragmentation by collision-induced dissociation (38% collision energy) were acquired in the ion trap for the most intense ions in "Top Speed" mode using Thermo Xcalibur Instrument Setup 3.0. The raw spectra were searched against the Rapid Annotation Server (40) (RAST) annotated genome database for *Paenibacillus* sp. 32352 using SEQUEST in Proteome Discoverer 1.4 (Thermo Fisher Scientific) with full MS peptide tolerance of 10 ppm and MS2 peptide tolerance of 0.3 Da. Constant modification of +57.021 Da (carbamidomethylation of cysteine residues), and dynamic modification of +15.995 Da (oxidation of methionine residues) were allowed in the search parameters. Results were filtered at a 1% false discovery rate for peptide assignments.

Gene Expression

Comparison of the levels of transcript expression from the Pn3P induced locus was performed by RT-PCR. *Paenibacillus* sp. 32352 was cultured in 5 ml of minimal medium containing 2% (w/v) carbon source, as described above. Triplicate bacterial cultures were harvested at mid-log phase (OD 600 nm 0.6), RNA was purified using E.N.Z.A. Bacterial RNA Kit, followed by TRIzol (Thermo Fisher Scientific) extraction of RNA from contaminating genomic DNA as described previously (41). RNA purity was assessed with nanodrop, and 1 μg of RNA was used for reverse transcription reaction using iscript CDNA synthesis kit (BioRad). Quantitative real time-PCR was performed in a 96-well plate on a MyiQ system (BioRad) with iQ SYBR green mastermix. Primers used in RT-PCR are listed in Table 3. The reactions were carried out in 20 μl, consisting of 10 μl of SYBR Green mix, 20 ng of cDNA, and 1 μM primer mix. The reaction conditions were 95° C. 180 s, followed by 45 cycles of 95° C. for 10 s, 55° C. for 20 s, and 72° C. for 30 s. The data were normalized to 16S rRNA transcript levels, and changes in expression level were calculated as fold change compared with cultures of minimal medium with glucose supplement.

TABLE 3

Oligonucleotides used.

| Oligonucleotide | Sequence (5' to 3') |
| --- | --- |
| Pbac_3551F-RT | gcacccgtgaatctggaagc (SEQ ID NO: 10) |
| Pbac_3551R-RT | ctccataggaataagcgagagatagg (SEQ ID NO: 11) |
| Pbac_3552F-RT | gagccgtcaggcaccatac (SEQ ID NO: 12) |
| Pbac_3552R-RT | ctctaatgcaggctgcgg (SEQ ID NO: 13) |
| Pbac_3554F-RT | ggctgcggcggcacta (SEQ ID NO: 14) |
| Pbac_3554R-RT | tcccaaaacatcccggatcg (SEQ ID NO: 15) |
| Pbac_1521F-RT | gatggcgtgaaagacgatac (SEQ ID NO: 16) |
| Pbac_1521R-RT | acagttttgtcgttaacgcc (SEQ ID NO: 17) |
| Pbac_16sF-RT | catgagggaatcatgaaacacg (SEQ ID NO: 18) |
| Pbac_16sR-RT | gggctttcttctcaggtacc (SEQ ID NO: 19) |
| Pbac_3551F | ggggacaagtttgtacaaaaaagcaggcttcgaaggagatagaaccatggcacccgtgaatctggaagc (SEQ ID NO: 20) |
| Pbac_3551R | ggggaccactttgtacaagaaagctgggtgctccacgatcaccttattcgataacg (SEQ ID NO: 21) |
| Pbac_3552F | ggggacaagtttgtacaaaaaagcaggcttcgaaggagatagaaccatggagccgtcaggcaccatac (SEQ ID NO: 22) |
| Pbac_3552R | ggggaccactttgtacaagaaagctgggtgcatccctcctgcgatgtg (SEQ ID NO: 23) |
| Pbac_3554F | ggggacaagtttgtacaaaaaagcaggcttcgaaggagatagaaccatgggctgcggcggcacta (SEQ ID NO: 24) |
| Pbac_3554R | ggggaccactttgtacaagaaagctgggtgcttctttgcgctcttgttatactc (SEQ ID NO: 25) |

Production of Recombinant Pn3Pase

The coding region of Pbac_3551 (ref seq WP_079915027), Pbac_3552 (ref seq WP_079915028), and Pbac_3554 (ref seq WP_079915030.1) (minus predicted signal peptide and stop codon) were amplified from *Paenibacillus* sp. 32352 genomic DNA (DNeasy blood and tissue kit, Qiagen) using 2× platinum superfi mastermix (Thermo Fisher Scientific) with overhang containing B-sites to facilitate gateway cloning (42) via BP reaction (Thermo Fisher Scientific) into pDONR221. Primers for cloning are listed in Table 3. After DH5a transformation and DNA sequence confirmation, an LR-clonase reaction was performed to insert the gene into the pET-DEST42 (Thermo Fisher Scientific) destination vector for the expression of a carboxy-terminal His$_6$-tagged fusion protein in *E. coli* BL21(DE3) cells. BL21(DE3) cells transformed with the pET-DEST42-"Pn3Pase" plasmid were grown in LB medium supplemented with 100 µg/ml ampicillin at 37° C., and cell density was monitored by absorbance at 600 nm. Once the OD 600 nm reached 0.6, the cells were transferred into 25° C., protein expression was induced by the addition of Isopropyl β-D-1-thiogalactopyranoside to a final concentration of 1 mM and the cell culture was allowed to incubate for 8 h (until A$_{600}$ reached ~1.1). Cells were harvested by centrifugation. Cells were then resuspended in phosphate-buffered saline (PBS, pH 7.2) with 1 mg/ml lysozyme for 20 min at 30° C., probe sonicated for 2 min (four cycles of 20 s on, 10 s off), clarified by centrifugation at 17,000×g for 1 h at 4° C., and passed through a 0.45 µm syringe filter. Recombinant Pn3Pase was purified by Ni$^{2+}$-NTA resin at 4° C., eluted with 300 mM imidazole and buffer exchanged into PBS pH 7.2. Protein concentration was determined by bicinchoninic acid assay. Purity was assessed by visualizing proteins on stain free tris-glycine gel (BioRad) using gel doc EZ imager (BioRad).

Enzyme Assays

Tritiated Pn3P assays—Recombinant enzyme activity against type 3 capsular polysaccharide was assayed by incubation of 2 µg/ml recombinant protein, or heat killed control, with 10 µg/ml $^3$H-Pn3P in PBS. The reaction was stopped after 2 h by heating at 100° C. for 5 minutes. Reaction mixture was separated on a superdex peptide 10/300 GL column (GE) on an NGC discoverer FPLC system (BioRad). Fractions of 1 ml were collected, and counts per minute in each fraction were counted in a Tri-Carb 2910 TR liquid scintillation analyzer (Perkin Elmer). Time course experiments were analyzed by the same method.

Reducing end sugar assays—recombinant Pn3Pase hydrolysis activity was determined by measuring the increase in reducing ends using the p-hydroxybenzoic acid hydrazide (PAHBAH) method (43). A reaction mixture (200 µl) containing 20 µg Pn3P, and 1 µg recombinant Pn3Pase in either 50 mM MOPS-NaOH (pH 6.0), 50 mM sodium phosphate buffer (pH 7.2), or 20 mM Tris-HCl (pH 8.0), was incubated at 37° C. for 1 h and then heated at 100° C. for 5 min to stop. Reaction mixture (40 µl) was mixed with 120 µl of 1% (w/v) PAHBAH-HCL solution, heated at 100° C. for 5 min. Absorbance at 405 nm was measured on a Biotek synergy H1 microplate reader in a clear bottom 96-well microplate. Concentrations of reducing sugars were calculated based on GlcA standard curves generated by the same method in respective buffers. Metal dependence assays were performed similarly with addition of $MgCl_2$ or $CaCl_2$) in phosphate buffer (pH 7.2).

Oligosaccharide Analysis

Pn3P powder (2 mg) was incubated with 100 µg of Pn3Pase at 37° C. for 48 h. The reaction was stopped by heating at 100° C. for 5 min, and loaded onto Superdex peptide 10/300 GL column (GE). Products were separated in phosphate buffered saline at a flow rate of 1 ml/min and monitored by refractive index. Fractions (0.5 ml) were collected and oligosaccharide peaks were purified, desalted into water on a packed fine P2 column (Biorad). Desalted oligos were lyophilized and subject to ESI-MS for mass determination and NMR for structural and reducing end identification.

NMR—Oligosaccharides were dissolved in 400 µL $^2H_2O$ (99.9%, Sigma-Aldrich, St. Louis, MO) and lyophilized three-times to remove the exchangeable protons. The samples were re-dissolved in 400 µl 99.96% $^2H_2O$ and transferred to NMR microtubes. $^1H$ spectroscopy, $^{13}C$ spectroscopy, $^1H$-$^1H$ correlated spectroscopy (COSY), and $^1H$-$^{13}C$ heteronuclear single quantum coherence spectroscopy (HSQC) experiments were all performed at 298 K on Bruker 600 or 800 MHz spectrometer with Topspin 2.1.6 software.

Pn3Pase Treatment of Type 3 *S. pneumoniae*

Fresh *Streptococcus pneumoniae* type 3 (WU2) and acapsular derivative (JD908) colonies on TSAB plates were inoculated to 0.1 OD in THY broth and cultured as described above. WU2 growth in presence of 100 µg/ml Pn3Pase was monitored over the course of 10 h by measuring OD 600 nm. WU2 grown in presence of 2 µg/ml, 10 µg/ml, or 10 µ/ml heat inactivated Pn3Pase, along with acapsular were grown for 6 hours, serially diluted, and plated to determine colony forming units. Cultures were harvested by centrifugation, washed in PBS, fixed in 2% paraformaldehyde for 20 min on ice, washed once more, and suspended in 1 ml PBS. For time course experiment, WU2 and acapsular strain were grown to mid-log phase (OD 600 nm of 0.6), harvested by centrifugation, washed in PBS, and then suspended in 1 ml PBS. 1 µg/ml Pn3Pase was added and incubated at 37° C. for the 1, 2, or 4 hours. Treated cells were serially diluted, and plated to determine colony forming units, fixed in 2% paraformaldehyde for 20 min on ice, washed once more, and suspended in 1 ml PBS.

Competition ELISA

ELISA plates (96 well, Nunc) were coated with 5 µg/ml Pn3P in 0.1 M carbonate buffer (pH 9.0) overnight at room temperature. Plates were washed 4-times with PBS +0.1% Tween (PBS-T) 20 using a Biotek 405/LS microplate washer. After 1 h blocking at room temperature with 1% BSA in PBS, microplate wells were incubated for 2 h at room temperature with fixed, treated cells that were pre-incubated for 30 min with Pn3P specific anti-serum in PBS-T. Plates were washed, and then incubated for 2 h at room temperature with 1:2000 dilution of goat anti-mouse IgG-AP (Southern Biotech #1030-04) in PBS-T. After washing, plates were incubated for ~30 min at 37° C. with 2 mg/ml phosphatase substrate (Sigma S0942) in 1 M Tris 0.3 mM $MgCl_2$. Absorbance at 405 nm was measured on a Biotek synergy H1 microplate reader. Percent inhibition of antibody binding was calculated by ((Uninhibited$_{OD405}$−Inhibited$_{OD405}$)/Uninhibited$_{OD405}$)×100.

Electron Microscopy

Electron microscopy was performed by Georgia Electron Microscopy core facility at the University of Georgia according to a modified method by Hammerschmidt et al.

(44). Treated cells were fixed in 2% glutaraldehyde and 0.15% ruthenium red in PBS buffer for 1 h on ice and then rinsed 2× with buffer containing 0.15% ruthenium red, 15 min per rinse. Cells were then fixed in 1% osmium tetroxide in buffer containing 0.15% ruthenium red for 1 h at room temperature followed by two rinses in buffer containing 0.15% ruthenium red, 15 min per rinse. Pellet was dehydrated in a graded ethanol series (30%, 50%, 75%, 95%, 100% and 100%) and two changes in 100% acetone, 15 min each step. Pellet was then infiltrated with 25% Spurr's resin and 75% acetone—2 h followed by sequential infiltration with 50% Spurr's resin and 50% acetone, 75% Spurr's resin and 25% acetone, 100% Spurr's resin and then polymerized in a 70° C. oven for 24 h. Samples were sectioned at 60 nm with a Diatome diamond knife and pick up on slot grids. Grids were post-stained on drops of uranyl acetate and lead citrate, 5 min each and rinsed with $H_2O$ 30 s between stains. Samples were scoped using a JEOL JEM 1011 TEM (JEOL USA, Peabody, MA) operated at 80 kV.

REFERENCES

1. Avery, O. T., and Dubos, R. (1930) The specific action of a bacterial enzyme on pneumococci of type III. Science 72, 151-152
2. Dubos, R., and Avery, O. T. (1931) Decomposition of the capsular polysaccharide of pneumococcus type III by a bacterial enzyme. J. Exp. Med. 54, 51-71
3. Sickles, G. M., and Shaw, M. (1934) A systematic study of microorganisms which decompose the specific carbohydrates of the pneumococcus. J. Bacteriol. 28, 415-431
4. Uetanabaro, A. P., Wahrenburg, C., Hunger, W., Pukall, R., Spröer, C., Stackebrandt, E., de Canhos, V. P., Claus, D., and Fritze, D. (2003) *Paenibacillus agarexedens* sp. nov., nom. rev., and *Paenibacillus agaridevorans* sp. nov. Int. J. Syst. Evol. Microbiol. 53, 1051-1057
5. Nakamura, L., and Swezey, J. (1983) Taxonomy of *Bacillus circulans* Jordan 1890-base composition and reassociation of deoxyribonucleic acid. Int. J. System. Bacteriol. 33, 46-52
6. Ash, C., Priest, F. G., and Collins, M. D. (1993) Molecular identification of rRNA group 3 bacilli (Ash, Farrow, Wallbanks and Collins) using a PCR probe test. Proposal for the creation of a new genus *Paenibacillus*. Antonie Van Leeuwenhoek 64, 253-260
7. Torriani, A., and Pappenheimer, A. M. (1962) Inducible polysaccharide depolymerases of *Bacillus palustris*. J. Biol. Chem. 237, 3-13
8. Rice, C. E., and Sickles, G. R. (1946) Studies of anti-pneumococcal serum; complement-fixing activity of fractionated rabbit serum. J. Immunol. 54, 267-274
9. Shaw, M., and Sickles, G. M. (1950) Production of specific pneumococcus carbohydrate-splitting enzymes in media to which the specific substrate was not added. J. Immunol. 64, 27-32
10. Forsee, W. T., Cartee, R. T., and Yother, J. (2009) Characterization of the lipid linkage region and chain length of the cellubiuronic acid capsule of *Streptococcus pneumoniae*. J. Biol. Chem. 284, 11826-11835
11. Forsee, W. T., Cartee, R. T., and Yother, J. (2006) Role of the carbohydrate binding site of the *Streptococcus pneumoniae* capsular polysaccharide type 3 synthase in the transition from oligosaccharide to polysaccharide synthesis. J. Biol. Chem. 281, 6283-6289

12. Middleton, D. R., Lorenz, W., and Avci, F. Y. (2017) Complete Genome Sequence of the Bacterium *Bacillus circulans* Jordan Strain 32352. Genome Announc. (In press)

13. Agard, N., Baskin, J., Prescher, J., Lo, A., and Bertozzi, C. (2006) A comparative study of bioorthogonal reactions with azides. ACS Chem. Biol. 1, 644-648

14. Chung, J., Kim, S., Choi, K., and Kim, J. O. (2015) Degradation of polyvinyl alcohol in textile waste water by *Microbacterium barkeri* KCCM 10507 and *Paenibacillus amylolyticus* KCCM 10508. Environ. Technol. 1-7

15. Konishi, J., and Maruhashi, K. (2003) 2-(2'-Hydroxyphenyl)benzene sulfinate desulfinase from the thermophilic desulfurizing bacterium *Paenibacillus* sp. strain A11-2: purification and characterization. Appl. Microbiol. Biotechnol. 62, 356-361

16. Knolhoff, A. M., Zheng, J., McFarland, M. A., Luo, Y., Callahan, J. H., Brown, E. W., and Croley, T. R. (2015) Identification and structural characterization of naturally-occurring broad-spectrum cyclic antibiotics isolated from *Paenibacillus*. J. Am. Soc. Mass. Spectrom. 26, 1768-1779

17. Oliveira, A., Leite, M., Kluskens, L. D., Santos, S. B., Melo, L. D., and Azeredo, J. (2015) The first *Paenibacillus larvae* bacteriophage endolysin (PlyP123) with high potential to control american foulbrood. PLoS One 10, e0132095

18. Guo, Y., Huang, E., Yuan, C., Zhang, L., and Yousef, A. E. (2012) Isolation of a *Paenibacillus* sp. strain and structural elucidation of its broad-spectrum lipopeptide antibiotic. Appl. Environ. Microbiol. 78, 3156-3165

19. Pasari, N., Adlakha, N., Gupta, M., Bashir, Z., Rajacharya, G. H., Verma, G., Munde, M., Bhatnagar, R., and Yazdani, S. S. (2017) Impact of module-X2 and carbohydrate binding module-3 on the catalytic activity of associated glycoside hydrolases towards plant biomass. Sci. Rep. 7, 3700

20. Yin, Y., Mao, X., Yang, J., Chen, X., Mao, F., and Xu, Y. (2012) dbCAN: a web resource for automated carbohydrate-active enzyme annotation. Nucl. Acid. Res. 40, W445-451

21. Magee, A. D., and Yother, J. (2001) Requirement for capsule in colonization by *Streptococcus pneumoniae*. Infect. Immun. 69, 3755-3761

22. Nelson, A. L., Roche, A. M., Gould, J. M., Chim, K., Ratner, A. J., and Weiser, J. N. (2007) Capsule enhances pneumococcal colonization by limiting mucus-mediated clearance. Infect. Immun. 75, 83-90

23. Dagan, R., Patterson, S., Juergens, C., Greenberg, D., Givon-Lavi, N., Porat, N., Gurtman, A., Gruber, W. C., and Scott, D. A. (2013) Comparative immunogenicity and efficacy of 13-valent and 7-valent pneumococcal conjugate vaccines in reducing nasopharyngeal colonization: a randomized double-blind trial. Clin. Infect. Dis. 57, 952-962

24. Gruber, W. C., Scott, D. A., and Emini, E. A. (2012) Development and clinical evaluation of Prevnar 13, a 13-valent pneumococcal CRM197 conjugate vaccine. Ann. NY Acad. Sci. 1263, 15-26

25. Kieninger, D. M., Kueper, K., Steul, K., Juergens, C., Ahlers, N., Baker, S., Jansen, K. U., Devlin, C., Gruber, W. C., Emini, E. A., Scott, D. A., and group, s. (2010) Safety, tolerability, and immunologic noninferiority of a 13-valent pneumococcal conjugate vaccine compared to a 7-valent pneumococcal conjugate vaccine given with routine pediatric vaccinations in Germany. Vaccine 28, 4192-4203

26. Petersen, T. N., Brunak, S., von Heijne, G., and Nielsen, H. (2011) SignalP 4.0: discriminating signal peptides from transmembrane regions. Nat. Meth. 8, 785-786

27. Finn, R. D., Attwood, T. K., Babbitt, P. C., Bateman, A., Bork, P., Bridge, A. J., Chang, H. Y., Dosztányi, Z., El-Gebali, S., Fraser, M., Gough, J., Haft, D., Holliday, G. L., Huang, H., Huang, X., Letunic, I., Lopez, R., Lu, S., Marchler-Bauer, A., Mi, H., Mistry, J., Natale, D. A., Necci, M., Nuka, G., Orengo, C. A., Park, Y., Pesseat, S., Piovesan, D., Potter, S. C., Rawlings, N. D., Redaschi, N., Richardson, L., Rivoire, C., Sangrador-Vegas, A., Sigrist, C., Sillitoe, I., Smithers, B., Squizzato, S., Sutton, G., Thanki, N., Thomas, P. D., Tosatto, S. C., Wu, C. H., Xenarios, I., Yeh, L. S., Young, S. Y., and Mitchell, A. L. (2017) InterPro in 2017-beyond protein family and domain annotations. Nucl. Acid. Res. 45, D190-D199

28. Grady, E., MacDonald, J., Liu, L., Richman, A., and Yuan, Z. (2016) Current knowledge and perspectives of *Paenibacillus*: a review. Microb. Cell Factor. 15

29. Baik, K. S., Choe, H. N., Park, S. C., Kim, E. M., and Seong, C. N. (2011) *Paenibacillus wooponensis* sp. nov., isolated from wetland freshwater. Int. J. Syst. Evol. Microbiol. 61, 2763-2768

30. Lim, J. M., Jeon, C. O., Lee, J. C., Xu, L. H., Jiang, C. L., and Kim, C. J. (2006) *Paenibacillus gansuensis* sp. nov., isolated from desert soil of Gansu Province in China. Int. J. Syst. Evol. Microbiol. 56, 2131-2134

31. Bouraoui, H., Rebib, H., Ben Aissa, M., Touzel, J. P., O'donohue, M., and Manai, M. (2013) *Paenibacillus marinum* sp. nov., a thermophilic xylanolytic bacterium isolated from a marine hot spring in Tunisia. J. Basic Microbiol. 53, 877-883

32. Kishore, K. H., Begum, Z., Pathan, A. A., and Shivaji, S. (2010) *Paenibacillus glacialis* sp. nov., isolated from the Kafni glacier of the Himalayas, India. Int J Syst Evol Microbiol 60, 1909-1913

33. Shida, O., Takagi, H., Kadowaki, K., Nakamura, L. K., and Komagata, K. (1997) Transfer of *Bacillus alginolyticus, Bacillus chondroitinus, Bacillus curdlanolyticus, Bacillus glucanolyticus, Bacillus kobensis*, and *Bacillus thiaminolyticus* to the genus *Paenibacillus* and emended description of the genus *Paenibacillus*. Int. J. Syst. Bacteriol. 47, 289-298

34. Li, Q. Q., Zhou, X. K., Dang, L. Z., Cheng, J., Hozzein, W. N., Liu, M. J., Hu, Q., Li, W. J., and Duan, Y. Q. (2014) *Paenibacillus nicotianae* sp. nov., isolated from a tobacco sample. Antonie Van Leeuwenhoek 106, 1199-1205

35. Leão, R. S., Pereira, R. H., Ferreira, A. G., Lima, A. N., Albano, R. M., and Marques, E. A. (2010) First report of *Paenibacillus cineris* from a patient with cystic fibrosis. Diagn. Microbiol. Infect. Dis. 66, 101-103

36. Hong, T. Y., and Meng, M. (2003) Biochemical characterization and antifungal activity of an endo-1,3-beta-glucanase of *Paenibacillus* sp. isolated from garden soil. Appl. Microbiol. Biotechnol. 61, 472-478

37. Xie, J. B., Du, Z., Bai, L., Tian, C., Zhang, Y., Xie, J. Y., Wang, T., Liu, X., Chen, X., Cheng, Q., Chen, S., and Li, J. (2014) Comparative genomic analysis of N2-fixing and non-N2-fixing *Paenibacillus* spp.: organization, evolution and expression of the nitrogen fixation genes. PLoS Genet. 10, e1004231

38. Allard, S., Enurah, A., Strain, E., Millner, P., Rideout, S. L., Brown, E. W., and Zheng, J. (2014) In situ evaluation of *Paenibacillus alvei* in reducing carriage of *Salmonella enterica* serovar Newport on whole tomato plants. Appl. Environ. Microbiol. 80, 3842-3849

39. Lim, J. M., Sherling, D., Teo, C. F., Hausman, D. B., Lin, D., and Wells, L. (2008) Defining the regulated secreted proteome of rodent adipocytes upon the induction of insulin resistance. J. Proteom. Res. 7, 1251-1263

40. Aziz, R. K., Bartels, D., Best, A. A., DeJongh, M., Disz, T., Edwards, R. A., Formsma, K., Gerdes, S., Glass, E. M., Kubal, M., Meyer, F., Olsen, G. J., Olson, R., Osterman, A. L., Overbeek, R. A., McNeil, L. K., Paarmann, D., Paczian, T., Parrello, B., Pusch, G. D., Reich, C., Stevens, R., Vassieva, O., Vonstein, V., Wilke, A., and Zagnitko, O. (2008) The RAST Server: rapid annotations using subsystems technology. BMC Genomics 9, 75

41. Rio, D. C., Ares, M., Hannon, G. J., and Nilsen, T. W. (2010) Purification of RNA using TRIzol (TRI reagent). Cold Spring Harb. Protoc. 2010, pdb.prot5439

42. Walhout, A. J., Temple, G. F., Brasch, M. A., Hartley, J. L., Lorson, M. A., van den Heuvel, S., and Vidal, M. (2000) GATEWAY recombinational cloning: application to the cloning of large numbers of open reading frames or ORFeomes. Meth. Enzymol. 328, 575-592

43. Blakeney, A., and Mutton, L. (1980) A simple colorimetric method for the determination of sugars in fruit and vegetables. J. Sci. Food Agric. 31, 889-897

44. Hammerschmidt, S., Wolff, S., Hocke, A., Rosseau, S., Müller, E., and Rohde, M. (2005) Illustration of pneumococcal polysaccharide capsule during adherence and invasion of epithelial cells. Infect. Immun. 73, 4653-4667

Example 2

Enzymatic Hydrolysis of Pneumococcal Capsular Polysaccharide Renders the Bacterium Vulnerable to Host Defense Abstract Despite a century of investigation, *Streptococcus pneumoniae* (Spn) remains a major human pathogen, causing a number of diseases such as pneumonia, meningitis, and otitis media. Like many encapsulated pathogens, the capsular polysaccharide (CPS) of Spn is a critical component for colonization and virulence in mammalian hosts. This study aimed to evaluate the protective role of a glycoside hydrolase, Pn3Pase, targeting the CPS of type 3 Spn, which is one of the most virulent serotypes. We have assessed the ability of Pn3Pase to degrade the capsule on a live type 3 strain. Through in vitro assays we observed that Pn3Pase treatment increases the bacterium's susceptibility to phagocytosis by macrophages and complement-mediated killing by neutrophils. We have demonstrated that in vivo Pn3Pase treatment reduces nasopharyngeal colonization, and protects mice from sepsis caused by type 3 Spn. Due to the increasing shifts in serotype distribution, rise in drug resistant strains, and poor immune responses to vaccine-included serotypes, it is necessary to investigate approaches to combat pneumococcal infections. This study evaluates the interaction of pneumococcal CPS with host at molecular, cellular and systemic levels and offers an alternative therapeutic approach for diseases caused by Spn through enzymatic hydrolysis of the CPS.

Introduction

*Streptococcus pneumoniae* (Spn), the causal agent of pneumonia, meningitis, and otitis media, remains a major threat to human health. This bacterium can stably colonize the human nasopharynx as a part of the normal commensal microflora (1-3). Colonization is the primary mode of transmission and a key step in the initiation of disease, despite asymptomatic carriage (4, 5). A critical component for survival within the host and full pathogenicity of most Spn strains is the capsular polysaccharide (CPS) (6, 7). The CPS is a large and distinct polysaccharide structure coating the entire surface of the bacterium. The capsule helps Spn evade the host immune system through resisting or inhibiting its phagocytosis by host macrophages while also limiting mucus-mediated clearance (8-11). Spn has over 90 unique capsular serotypes, each differing in monosaccharide composition and linkage, as well as other modifications such as acetylation (12). The requirement of the CPS in bacterial virulence, surface accessibility, and antigenicity, has made it a target in vaccination studies for over 100 years (12-16). Great strides have been made at increasing the immunogenicity and efficacy of pneumococcal vaccines that utilize the CPS by conjugation to a protein carrier (17, 18). Current pneumococcal vaccines aim to provide serotype-specific protection for some of the most relevant clinical serotypes (12, 13). The use of the 7 and 13-valent pneumococcal conjugate vaccines, PCV7 and PCV13 (Prevnar; Pfizer) has been a major success; reducing invasive pneumococcal disease (IPD) rates significantly in both vaccinated and unvaccinated populations (15, 19-22).

While the conjugate vaccines have been effective for preventing carriage and IPD caused by most included serotypes, the exception has been serotype 3. The pneumococcal type 3 polysaccharide (Pn3P) component of the current PCV13 induces variable immune responses to Spn serotype 3, (23-25). Pn3P is a linear polymer of $-3)\beta GlcA(1-4)\beta Glc$ (1-disaccharide repeating units with an average molecular weight of $>400$ kDa (26, 27). It was noted that significantly higher serum titers are required for serotype 3 in comparison with other serotypes for opsonophagocytic killing of Spn (12, 28, 29). Numerous animal model and epidemiology studies have associated type 3 strains with increased virulence and death risk compared to other pneumococcal serotypes (30-32). A recent case report demonstrated a fatal case of IPD caused by serotype 3, highlighting increased complications and generally poor outcomes associated with this invasive serotype (33). In addition, recent data indicate that Spn strains are resistant to one or more antibiotics in 30% of IPD cases (34). The Centers for Disease Control and Prevention predict a rise in antibiotic-resistance features of Spn (35, 36).

The inability of vaccination to provide adequate protection against one of the most aggressive serotypes of this major human pathogen necessitates the urgent exploration of alternative approaches for type 3 pneumococcal infections. This, along with a rise in the prevalence of antibiotic resistant strains (37, 38) led us to revisit early studies by Avery and Dubos, who discovered a soil dwelling bacterium producing an enzyme that hydrolyzes Pn3P (39-41). Previously, we have identified this bacterium as a *Paenibacillus* species, cloned its type 3 specific glycosyl hydrolase, Pn3Pase, and characterized its degradation products (26, 42). In light of the continued prevalence, and severity of serotype 3 Spn, we postulated the potential use of this purified protein as a therapeutic agent for hyper virulent serotype 3 infections. Here, we investigated the ability of Pn3Pase to degrade the capsule on a live virulent type 3 Spn strain and therefore render the bacterium susceptible to host immune clearance.

Materials and Methods

Bacterial Strains and Growth Conditions

*Streptococcus pneumoniae* type 3 (WU2 strain) and acapsular derivative (JD908) (60, 61), generous gifts from Moon Nahm (University of Alabama at Birmingham), were cultured aerobically without shaking at 37° C. on Tryptic Soy Agar with 5% sheep blood (TSAB), or in Todd Hewitt Broth plus 0.5% yeast extract (THY) (BD Biosciences).

Mice

Eight-week-old female BALB/c mice were obtained from Taconic Biosciences (Hudson, NY) and housed in the Central Animal Facility at the University of Georgia. Mice were kept in microisolator cages and handled under BSL-2 hoods.

Production of Recombinant Pn3Pase

Pn3Pase was produced as described previously with minor modifications (26). Briefly, BL21(DE3) cells transformed with the pET-DEST42-"Pn3Pase" plasmid were grown in Terrific Broth supplemented with 100 µg/ml ampicillin at 37° C., and cell density was monitored by absorbance at 600 nm. Once the OD 600 nm reached 1.0, the cells were transferred into 18° C. Protein expression was induced by the addition of Isopropyl β-D-1-thiogalactopyranoside to a final concentration of 1 mM and the cell culture was allowed to incubate for 18 h. Cells were harvested by centrifugation, resuspended in phosphate-buffered saline (PBS, pH 7.2) and lysed by pressure lysis. The lysate was clarified by centrifugation at 17,000×g for 1 h at 4° C., and passed through a 0.45 µm syringe filter. Recombinant Pn3Pase was purified by Ni2+-NTA resin at 4° C., eluted with 300 mM imidazole and buffer exchanged into PBS pH 7.2. Protein concentration was determined by the bicinchoninic acid assay according to the instructions of the manufacturer. Purity was evaluated by coomassie staining.

Pn3Pase Treatment of Type 3 *S. pneumoniae*

Fresh *Streptococcus pneumoniae* type 3 (WU2) and acapsular derivative (JD908) colonies on TSAB plates were inoculated to 0.1 OD 600 nm in THY broth and cultured as described above. WU2 growth in presence of 100 µg/ml Pn3Pase was monitored over the course of 10 h by measuring OD 600 nm. WU2 was grown in presence of 2 µg/ml, 10 µg/ml, or 10 µg/ml heat inactivated Pn3Pase for 6 hours, serially diluted, and plated to determine colony forming units. Cultures were harvested by centrifugation, washed in PBS, fixed in 2% paraformaldehyde for 20 min on ice, washed once more, and suspended in 1 ml PBS. For the time course experiment, WU2 and the acapsular strain were grown to mid-log phase (OD 600 nm of 0.6), harvested by centrifugation, washed in PBS, and then suspended in 1 ml PBS. Then, 1 µg/ml Pn3Pase was added and incubated at 37° C. for the 1, 2, or 4 hours. Treated cells were serially diluted, and plated to determine colony forming units, fixed in 2% paraformaldehyde for 20 min on ice, washed once more, and suspended in 1 ml PBS.

Competition ELISA

ELISA plates (96 well, Nunc) were coated with 5 µg/ml Pn3P in 0.1 M carbonate buffer (pH 9.0) overnight at room temperature. Plates were washed 4-times with PBS+0.1% Tween (PBS-T) 20 using a Biotek 405/LS microplate washer. After 1 h blocking at room temperature with 1% BSA in PBS, microplate wells were incubated for 2 h at room temperature with fixed, treated cells that were pre-incubated for 30 min with Pn3P specific anti-serum in PBS-T. Plates were washed, and then incubated for 2 h at room temperature with 1:2000 dilution of goat anti-mouse IgG-AP (Southern Biotech #1030-04) in PBS-T. After washing, plates were incubated for ~30 min at 37° C. with 2 mg/ml phosphatase substrate (Sigma S0942) in 1 M Tris 0.3 mM MgCl$_2$. Absorbance at 405 nm was measured on a Biotek synergy H1 microplate reader. Percent inhibition of antibody binding was calculated by ((Uninhibited$_{OD405}$-Inhibited$_{OD405}$)/Uninhibited$_{OD405}$)×100.

Electron Microscopy

Electron microscopy was performed by the Georgia Electron Microscopy core facility at the University of Georgia according to a modified method by Hammerschmidt et al. (62). Treated cells were fixed in 2% glutaraldehyde, 2% paraformaldehyde, 0.075M lysine-acetate and 0.075% ruthenium red in PBS buffer for 1 h on ice and then rinsed 2× with buffer containing 0.15% ruthenium red, 15 min per rinse. Cells were then fixed in 1% osmium tetroxide in buffer containing 0.15% ruthenium red for 1 h at room temperature followed by two rinses in buffer containing 0.15% ruthenium red, 15 min per rinse. Pellet was dehydrated in a graded ethanol series (30%, 50%, 75%, 95%, 100% and 100%) and two changes in 100% acetone, 15 min each step. Pellet was then infiltrated with 25% Spurr's resin and 75% acetone—2 h followed by sequential infiltration with 50% Spurr's resin and 50% acetone, 75% Spurr's resin and 25% acetone, 100% Spurr's resin and then polymerized in a 70 □C oven for 24 h. Samples were sectioned at 60 nm with a Diatome diamond knife and picked up on slot grids. Grids were post-stained on drops of uranyl acetate and lead citrate, 5 min each and rinsed with H2O 30 s between stains. Samples were scoped using a JEOL JEM 1011 TEM (JEOL USA, Peabody, MA) operated at 80 kV.

Phagocytosis

Mid-log phase WU2 and JD908 (acapsular) cultures were washed and stained with 10 µM Carboxyfluorescein succinimidyl ester (CFSE) for 30 minutes at room temperature. The WU2 strain was concurrently treated with 2 µg/ml of active or heat-inactivated Pn3Pase. Bacterial cell pellets were washed extensively, suspended in 1 ml sterile PBS. 10$^7$ bacteria were added to a confluent monolayer of murine leukemia virus transformed macrophage line, RAW 264.7 (American Type Culture Collection (ATCC) Manassas, VA) with active or heat-inactivated baby rabbit complement (Pel-Freez) in a 24 well plate and incubated for 1 hour at 37° C. Wells were washed 4× with PBS to remove extracellular bacteria. Macrophages were fixed with 2% paraformaldehyde at 4° C. for 15 minutes and removed from the plate. For microscopy, cells were incubated at room temperature for 30 minutes with a 1/500 dilution of biotinylated wheat germ agglutinin (Vector labs) in 1% bovine serum albumin followed by a 30-minute room temperature incubation with a 1/1000 dilution of streptavidin APC (Biolegend). Cells were imaged with a 40× objective lens. Flow cytometry was performed on a Beckman Cytoflex S cytometer and analyzed by FlowJo. Cells were gated on the macrophage population by scatter plot. A non-CFSE labeled control served to gate highly fluorescent cell populations. The Pn3Pase dose dependent experiment was performed as above with addition of active complement.

Complement Deposition

A complement deposition assay was performed as described previously (63). Type 3 WU2 and acapsular (JD908) strains of bacteria were resuspended in 3% BSA in PBS. Aliquots (in duplicate wells on a 96-well round-bottom plate) were stained with Hoechst 33342 and treated with inactivated or functional Pn3Pase at 5 or 50 µg/ml for 1 hour at 37° C. Normal mouse serum (1:10 dilution) was added to the samples for 30 minutes at 37° C. Cells were washed and stained with FITC-conjugated goat antibody to mouse complement (MP BioMedical, Santa Ana, CA) at 4° C. for 30 minutes. Samples were washed with 3% BSA in PBS and resuspended in 2% paraformaldehyde to fix. Samples were then analyzed with flow cytometry. Mean fluorescent intensity (MFI) of FITC-A was calculated from gating of Hoechst-positive cells.

Modified OPA

An opsonophagocytic killing assay was performed as described previously with modifications (43). Briefly, the type 3 WU2 and acapsular (JD908) strains were incubated in duplicate wells in a 96-well round-bottom plate for 1 hour or 4 hours at 37° C. with or without Pn3Pase (inactivated or functional at concentrations of 5 or 50 ug/ml) in opsonization buffer B (OBB, sterile 1×PBS with Ca++/Mg++, 0.1% gelatin, and 5% heat-inactivated FetalClone). Human promyelocytic leukemia cell line, HL-60 (ATCC Manassas, VA) were cultured in RPMI with 10% heat-inactivated FetalClone (HyClone) and 1% L-glutamine. HL-60 cells were differentiated using 0.6% N,N-dimethylformamide (DMF, Fisher) for three days before performing the OPA assay, harvested, and resuspended in OBB. Active or heat-inactivated (no complement) baby rabbit complement (Pel-Freez) was added to HL-60 cells at 1:5 final volume. The HL-60/complement mixture was added to the serum/bacteria at $5 \times 10^5$ cells/well (for controls, no HL-60/complement was added; equal volumes of OBB buffer was added instead). The final reactions were incubated at 37° C. for 1 hour. The reactions were stopped by incubating the samples on ice for approximately 20 minutes. Then, 10 µl of each reaction was diluted to a final volume of 50 µl and plated onto blood agar plates in duplicate. Plates were incubated overnight at 30° C. in anaerobic conditions and counted the next day. Percent survival was calculated as each duplicate reaction normalized to mean values obtained for control samples (reactions without HL-60 cells, 100% survival).

Murine Intranasal Colonization

An intranasal colonization was performed essentially as described by Puchta et al (64). Mid-log phase WU2 cultures were washed with sterile PBS and suspended at a concentration of $10^8$ CFU/ml or $10^6$ CFU/10 µl. Groups of 5 to 10 unanesthetized 8-week-old female BALB/c mice (Taconic) were intranasally inoculated with $10^6$ CFU/10 µl as previously described. Mice were either inoculated with 10 µl of PBS as vehicle on day 0, 3, and 7 or treated by administering 50 µg of Pn3Pase in 10 µl PBS on day 0, 0 and 3, or 0, 3, and 7. Nasal lavage fluid was obtained on day 10 by flushing out the nasopharynx with PBS by insertion of a 25 gauge needle into the trachea to expel 500 µl through the nares. Serial dilutions of the nasal lavage fluid were plated on Tryptic Soy Agar with 5% sheep blood (TSAB), to enumerate the colony forming units. A sandwich ELISA (Biolegend mouse ELISA MAX) was performed according to manufacturer's instructions to determine TL-6 and TNFα cytokine levels in the lavage fluid.

Murine Sepsis Challenge

Mid-log phase WU2 cultures were washed with sterile PBS and suspended at a concentration of $5 \times 10^3$ CFU/100 µL. Groups of 4 unanesthetized 8-week-old female BALB/c mice (Taconic) were injected intraperitoneally (I.P.) with $5 \times 10^3$ CFU. Control mice were injected I.P. with 5 µg of heat inactivated Pn3Pase in 100 µL of PBS at time 0, or directly after infection. Treated mice were administered I.P. 0.5 µg or 5 µg of Pn3Pase in 100 µL PBS at time 0, 12, or 24 hours post infection. Animals were monitored every 12 hours.

Results

Pn3Pase Removes Capsule from Growing Type 3 Spn

Figures 9A, 9B:
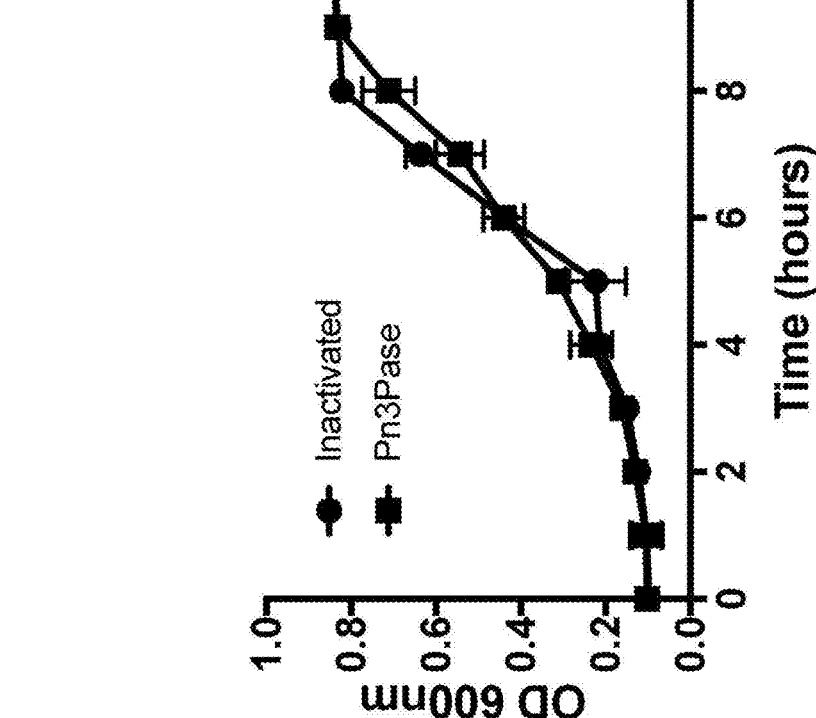

The encapsulated type 3 WU2 strain was cultured for 10 hours with the recombinant enzyme added to the growth medium and bacterial growth was monitored by measuring OD at 600 nm to assess effects of Pn3Pase treatment on growing type 3 Spn. Pn3Pase treatment of cells demonstrated no adverse growth or cytotoxic effects on the bacteria (FIG. 9A). In the same experiment, we obtained comparable CFU values for both enzyme treated and non-treated groups at two-hour intervals (data not shown). To assess direct impact of enzyme treatment on bacterial survival, a log-phase culture was isolated and suspended in nutrient-free buffer with active, or heat inactivated Pn3Pase. Enzyme treated cells showed comparable counts to inactivated and PBS controls over the 8-hour time course (FIG. 9B).

Figure 10A:
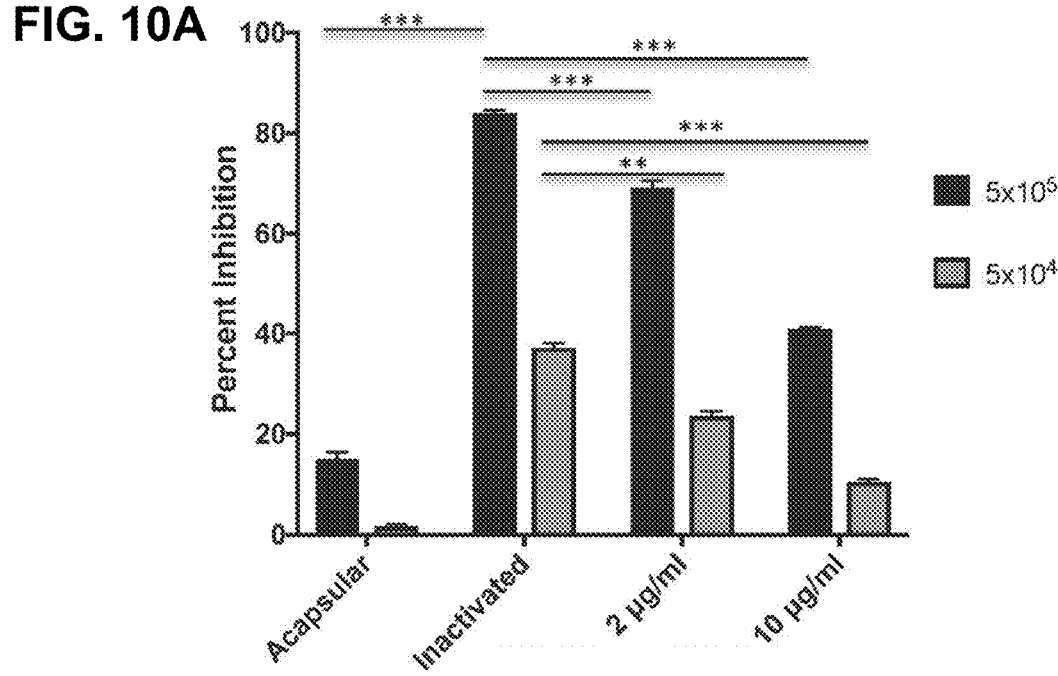
FIGS. 10A-10E show depleting the capsule on live type 3 Spn by Pn3Pase treatment.

The bacterial cells grown in the presence of Pn3Pase were then examined by competition ELISA to determine if the enzyme led to efficient capsule removal in the growing cultures. After treatment, fixed whole cells, at two different concentrations, were used to compete for Pn3P specific antibodies binding to the Pn3P coated plate. The acapsular WU2 mutant strain (JD908) showed minimal to no inhibition of antibody binding due to its lack of capsule. Heat inactivated Pn3Pase treated cells demonstrated the highest percent inhibition as cell surfaces should be fully decorated with CPS. With active Pn3Pase treatment, inhibition of antibody binding begins to decrease in a Pn3Pase concentration dependent manner (FIG. 10A), suggesting that the enzyme strips the capsule from live, growing type 3 Spn.

Figure 10B:
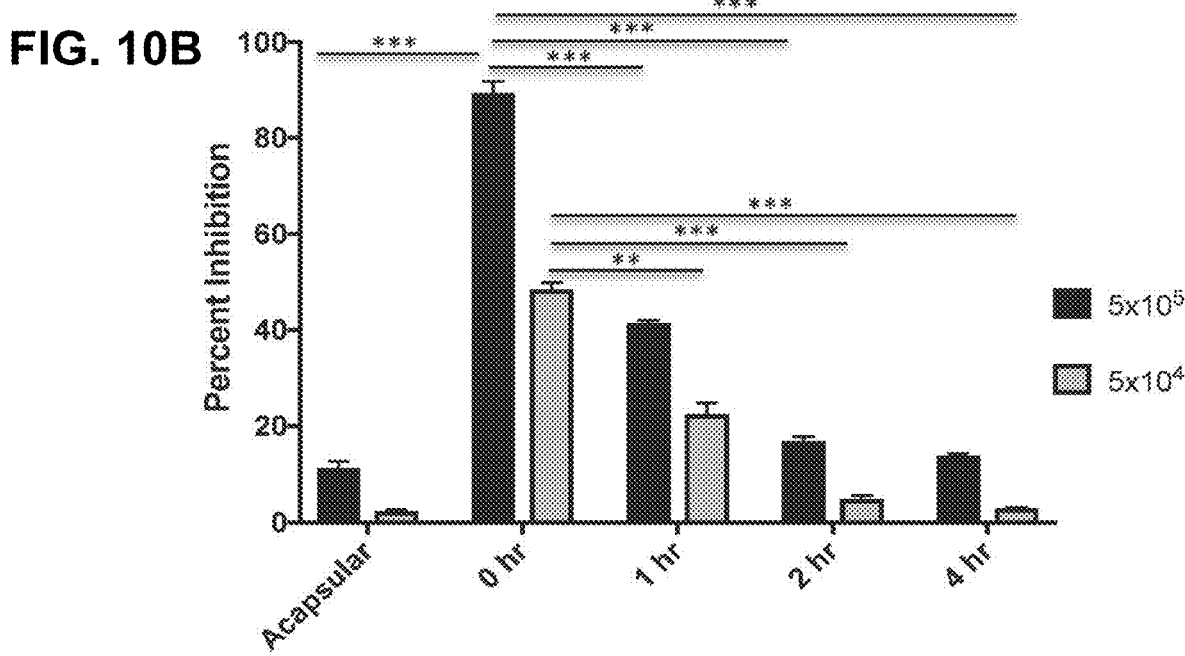

A time course experiment was performed in which the bacterial cells were grown to mid-log phase, suspended in PBS, and treated with Pn3Pase for 0, 1, 2, or 4 hours. The Pn3Pase dose was lowered to 1 µg/ml for this assay given that the WU2 strain should not be actively growing and therefore not producing a substantial amount of new CPS under these conditions. At each time point, the treated cells were fixed and examined by competition ELISA as described above. The acapsular WU2 mutant strain (JD908), again, showed minimal to no inhibition due to its lack of capsule. Untreated cells exhibited the highest percent inhibition, indicative of a cell surface fully decorated with CPS. With increasing Pn3Pase incubation time, inhibition of antibody binding begins to decrease significantly, appearing essentially acapsular after 2- or 4-hour treatments (FIG. 10B).

Figure 10C:
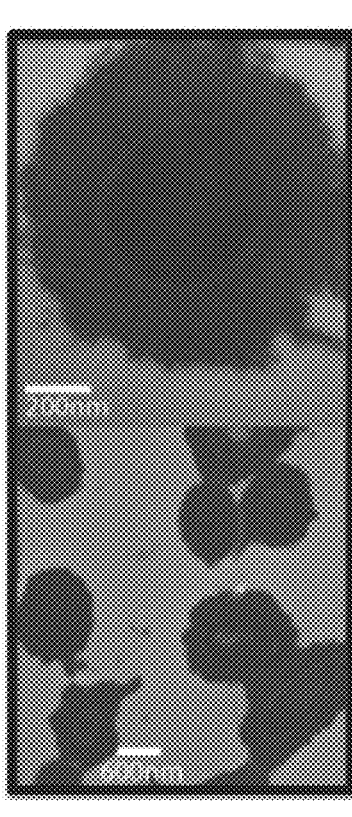
Figure 10D:
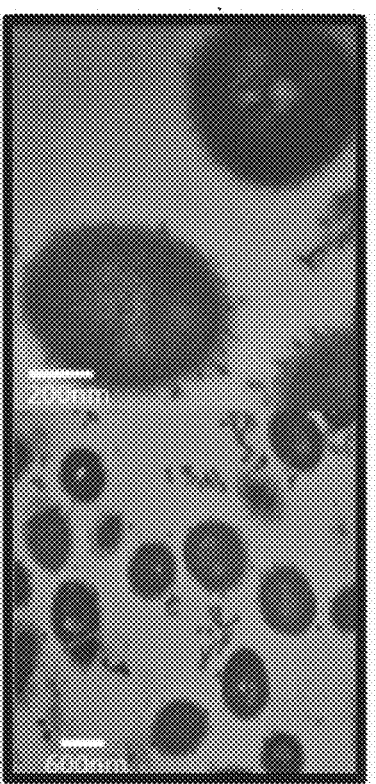
Figure 10E:
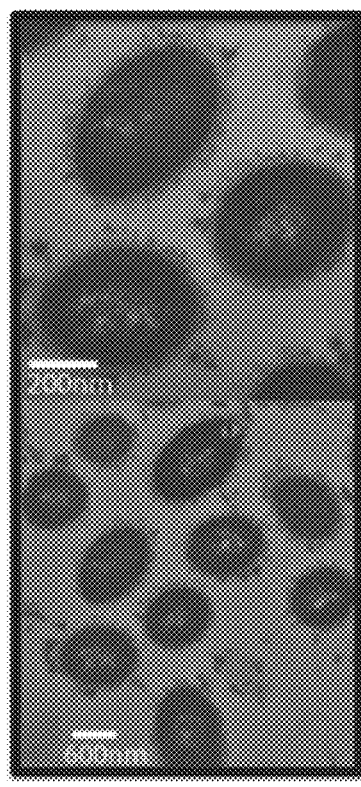

The Pn3Pase treated cells were visualized by transmission electron microscopy and compared to the cells treated with heat inactivated Pn3Pase. The heat inactivated enzyme treated cells displayed a thick, complete CPS coat across their surface (FIG. 10C), undoubtedly distinct from the acapsular mutant (FIG. 10D). The capsule layer of the enzyme treated cells exhibited little to no capsule (FIG. 10E), appearing as acapsular.

Pn3Pase Treatment of Type 3 Spn Allows Phagocytic Cell Uptake and Killing

Figure 11A:
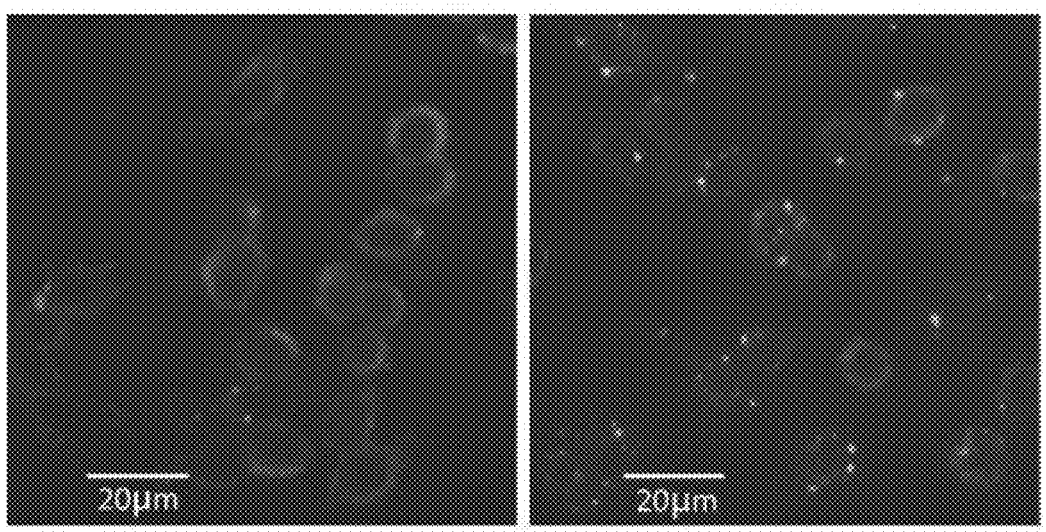
FIGS. 11A-11C show macrophage uptake of Pn3Pase treated type 3 Spn.
Figure 11B:
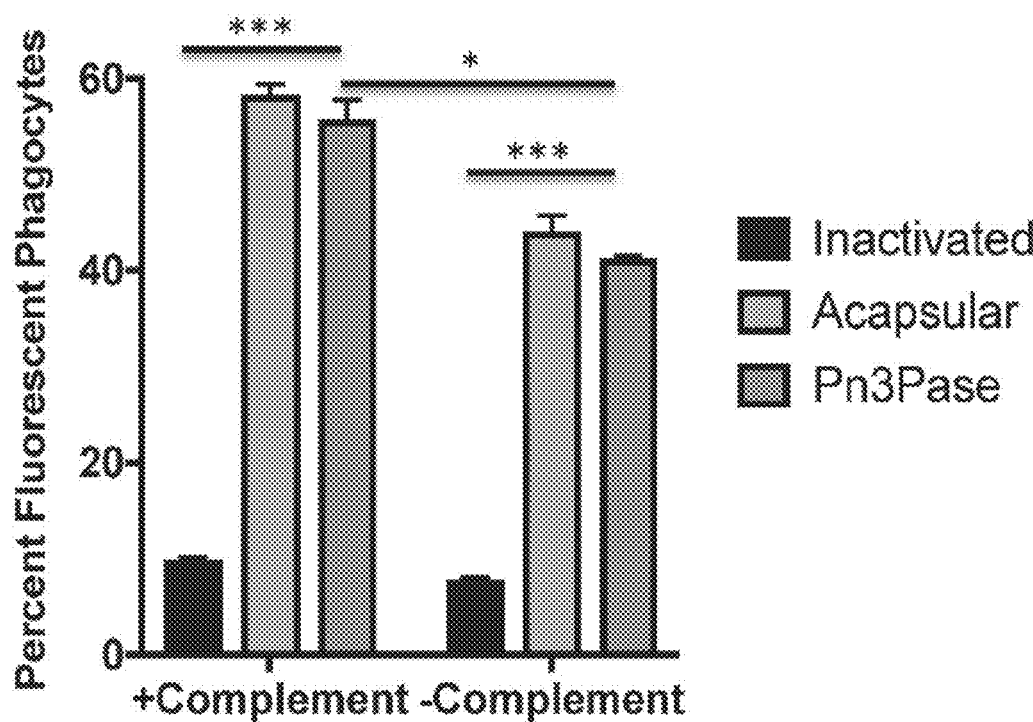
Figure 11C:
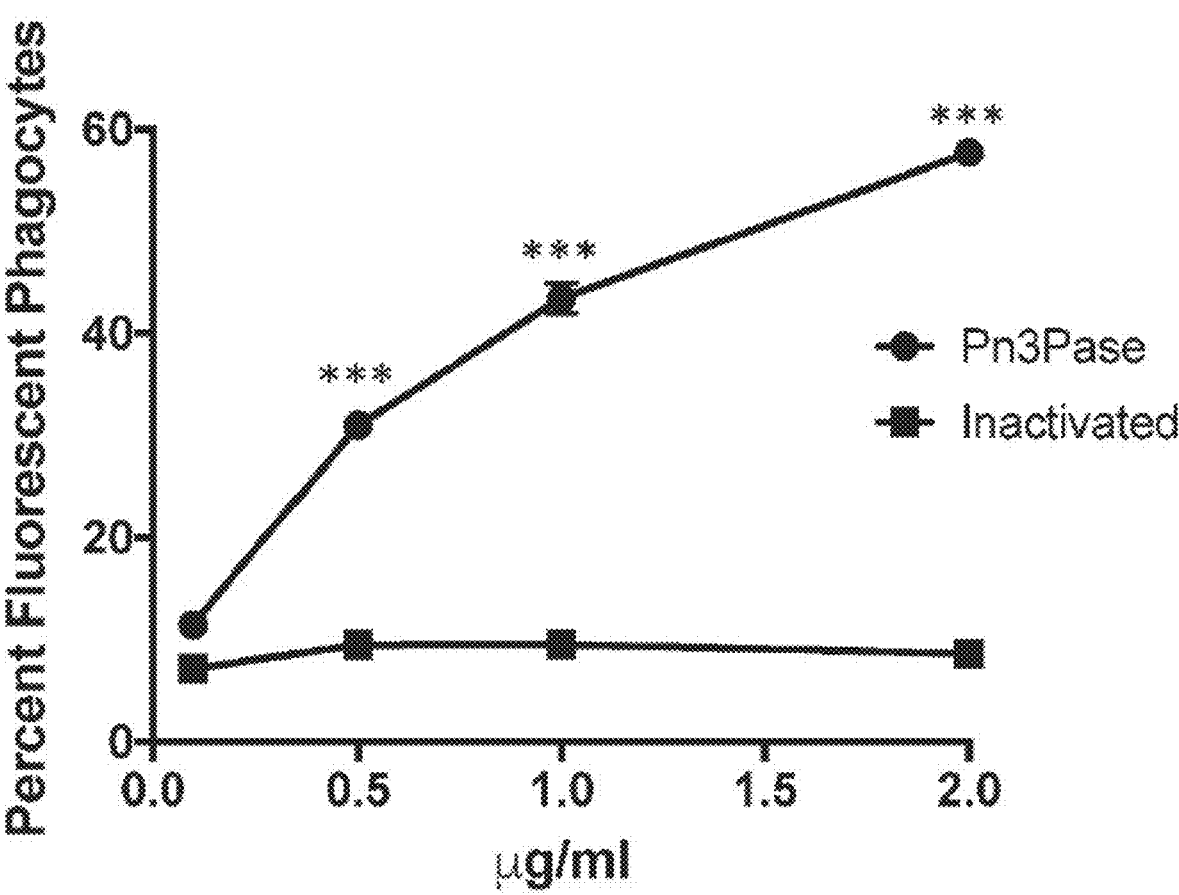

A major virulence mechanism of the CPS is to provide the bacterium the ability to resist phagocytosis by host phagocytic cells (1, 6). To investigate the effect of Pn3Pase treatment on uptake by macrophages in vitro, we stained mid-log phase bacterial cultures with carboxyfluorescein succinimidyl ester (CFSE) and then treated with Pn3Pase followed by incubation with RAW 264.7 macrophages. Macrophages were then washed extensively and imaged by fluorescent microscopy (FIG. 11A). The extent of bacterial uptake by macrophages was quantified by flow cytometry. Bacteria treated with the enzyme were taken up by macrophages significantly more than the encapsulated strain. We then determined the percentage of fluorescent macrophages, representing the phagocytosis of fluorescent bacteria (FIGS. 11C-D). The encapsulated type 3 strain incubated with heat inactivated Pn3Pase had minimal fluorescently labeled phagocytes whereas Pn3Pase treated bacteria were as efficiently taken up by the macrophages as the acapsular mutant strain. Uptake was partially dependent on complement as evidenced by higher bacterial uptake in the presence of complement (FIG. 11C). Pn3Pase treatment rendered the bacteria more susceptible to phagocytic engulfment by RAW macrophages in a dose dependent manner, while even high doses of the inactivated enzyme had no significant effect on bacterial uptake (FIG. 11D).

Figure 12:
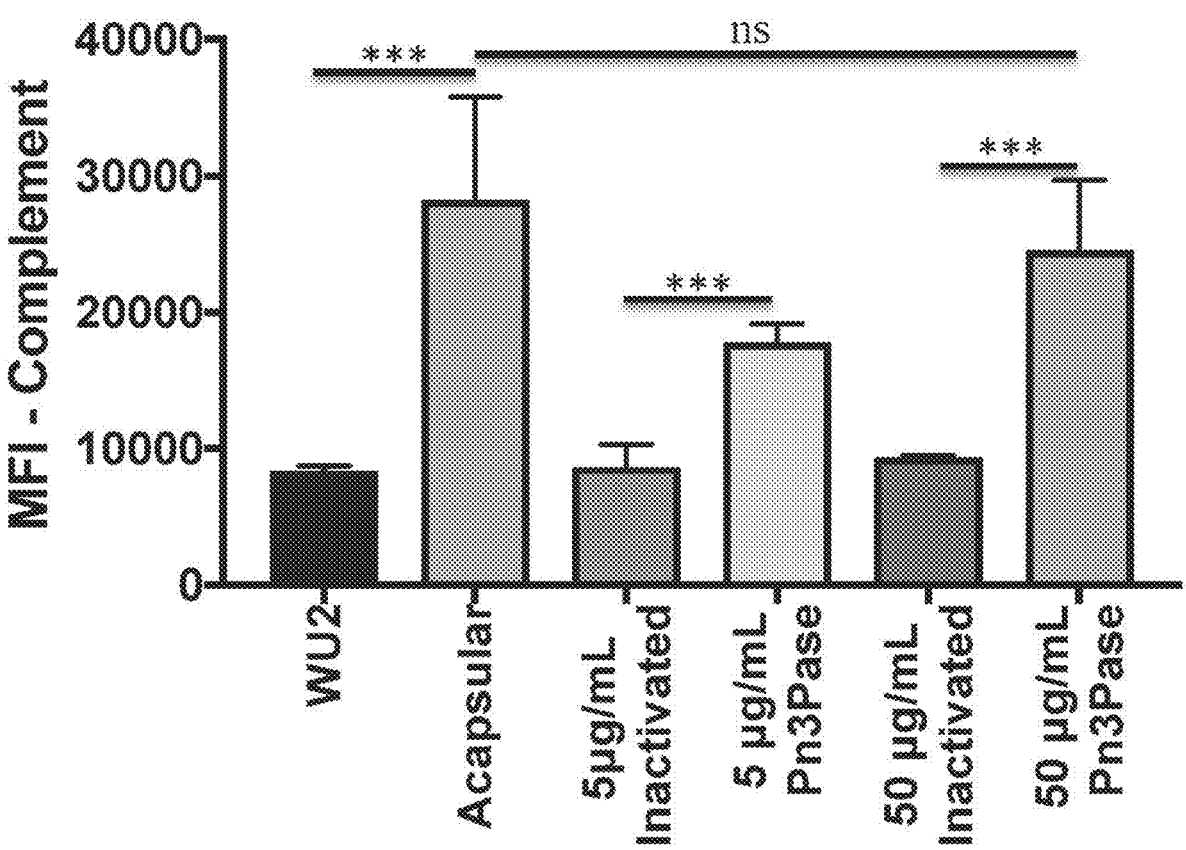
FIG. 12 shows effect of Pn3Pase treatment on complement deposition on Spn surface. Analysis of mouse complement deposition on Pn3Pase treated or untreated type 3 Spn by flow Cytometry. Quantification by Mean fluorescent intensity (MFI) of FITC-A was calculated from gating of Hoechst-positive cells. Statistical significance was determined with the two-tailed Student t test  P<0.01, * P<0.001, ns=not significant.

Complement deposition on the pneumococcal surface is an important mechanism aiding in efficient phagocytosis and clearance (10, 11). Since CPS provides complement evasive properties to the bacterium (10, 11), we investigated the effect of capsule removal by Pn3Pase treatment on C3b deposition on the bacterial surface. The encapsulated type 3 WU2 strain was treated with active or inactive Pn3Pase. The untreated type 3 strain and the acapsular mutant were included as additional controls. Bacteria were then incubated with normal mouse serum, washed, and stained with FITC-conjugated antibody to mouse complement. Fixed samples were then analyzed with flow cytometry. In a dose dependent manner, Pn3Pase treatment increased the deposition of complement on the bacterial surface, reaching the levels of deposition on the acapsular strain. Complement had minimal binding to the bacteria either untreated or treated with inactivated-Pn3Pase (FIG. 12).

Figure 13:
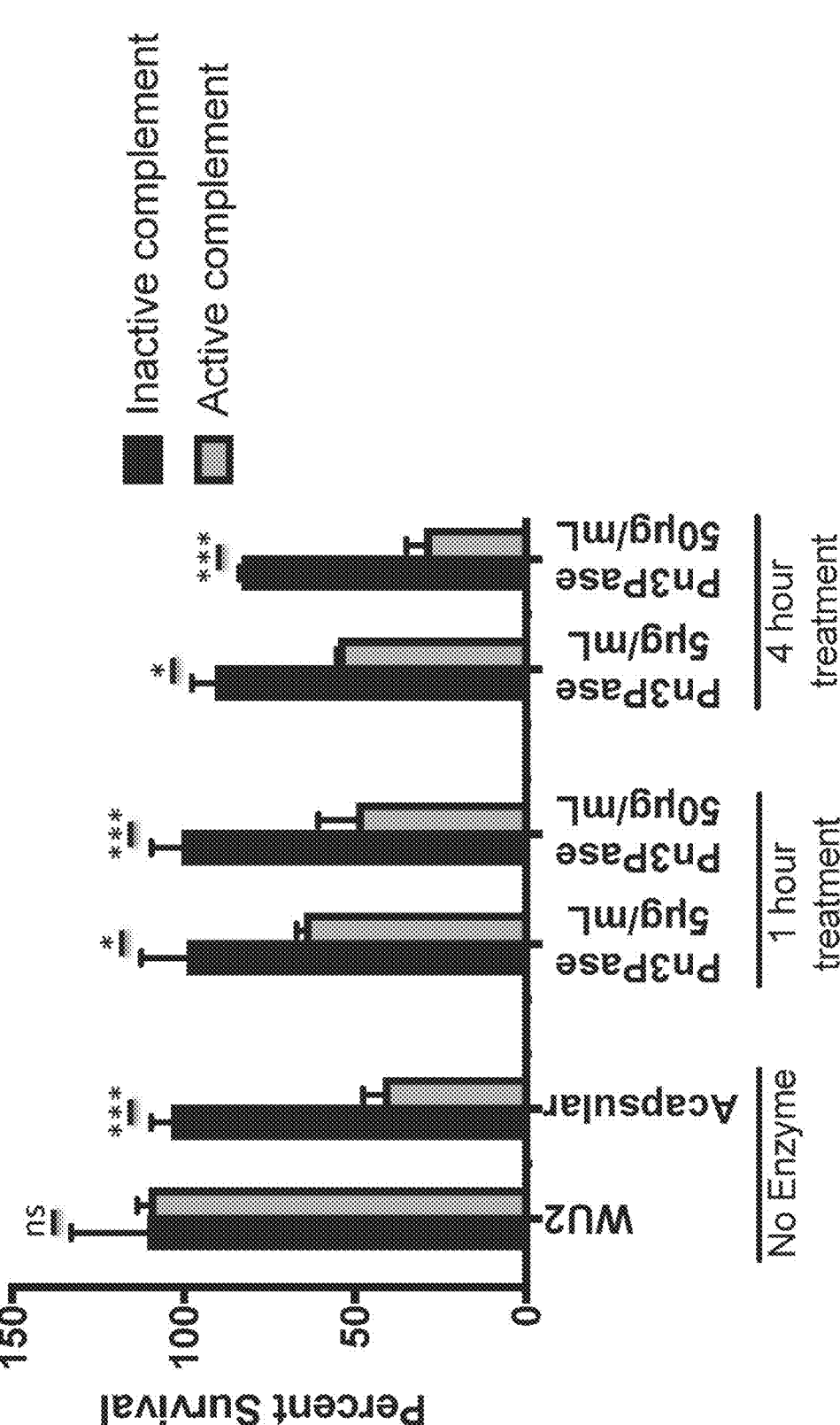
FIG. 13 shows effect of Pn3Pase treatment on complement mediated killing by neutrophils. Complement mediated killing capacity of differentiated HL-60 cells on Pn3Pase treated Spn. Percent survival was calculated as each duplicate reaction normalized to mean values obtained for control samples (reactions without HL60 cells, 100% survival). Statistical significance was determined with the two-tailed Student t test * P<0.001,  P<0.01, * P<0.05, ns=not significant.

The standard in vitro assay to assess phagocytic killing of Spn is an opsonophagocytosis assay (OPA) in which HL-60 cells are differentiated into neutrophils to engulf and clear antibody opsonized bacteria. This method has been widely used to measure the quality of antibody responses in numerous vaccine studies (43-48). Neutrophils are one of the most important components of innate immunity against pathogenic bacteria in the lungs (49-51). While the focus of this study is not on humoral immune responses to Spn, we have used a modified OPA to evaluate complement-mediated neutrophil killing of type 3 Spn treated with Pn3Pase in vitro. Encapsulated type 3 Spn was incubated with active or heat inactivated Pn3Pase. Differentiated HL-60 cells were pre-incubated with active or heat-inactivated complement. The mixture of HL-60 cells and complement was added to the bacteria and incubated at 37° C. for 1 hour. To quantify the surviving bacteria in the experimental groups, the reaction mixtures were plated and CFUs were counted the next day. Percent survival was calculated as each duplicate reaction normalized to mean values obtained from reactions without neutrophils, which served as control samples (100% survival). The enzyme-untreated, encapsulated type 3 strain was able to escape neutrophil killing to show maximum survival while the acapsular mutant strain was reduced to nearly 40% viability upon incubation with active complement and neutrophils (FIG. 13). Pn3Pase treatment to remove the capsule rendered the type 3 strain susceptible to complement dependent neutrophil killing similar to the acapsular strain (FIG. 13).

Pn3Pase Limits Nasopharyngeal Colonization

Figures 14A, 14B, 14C:
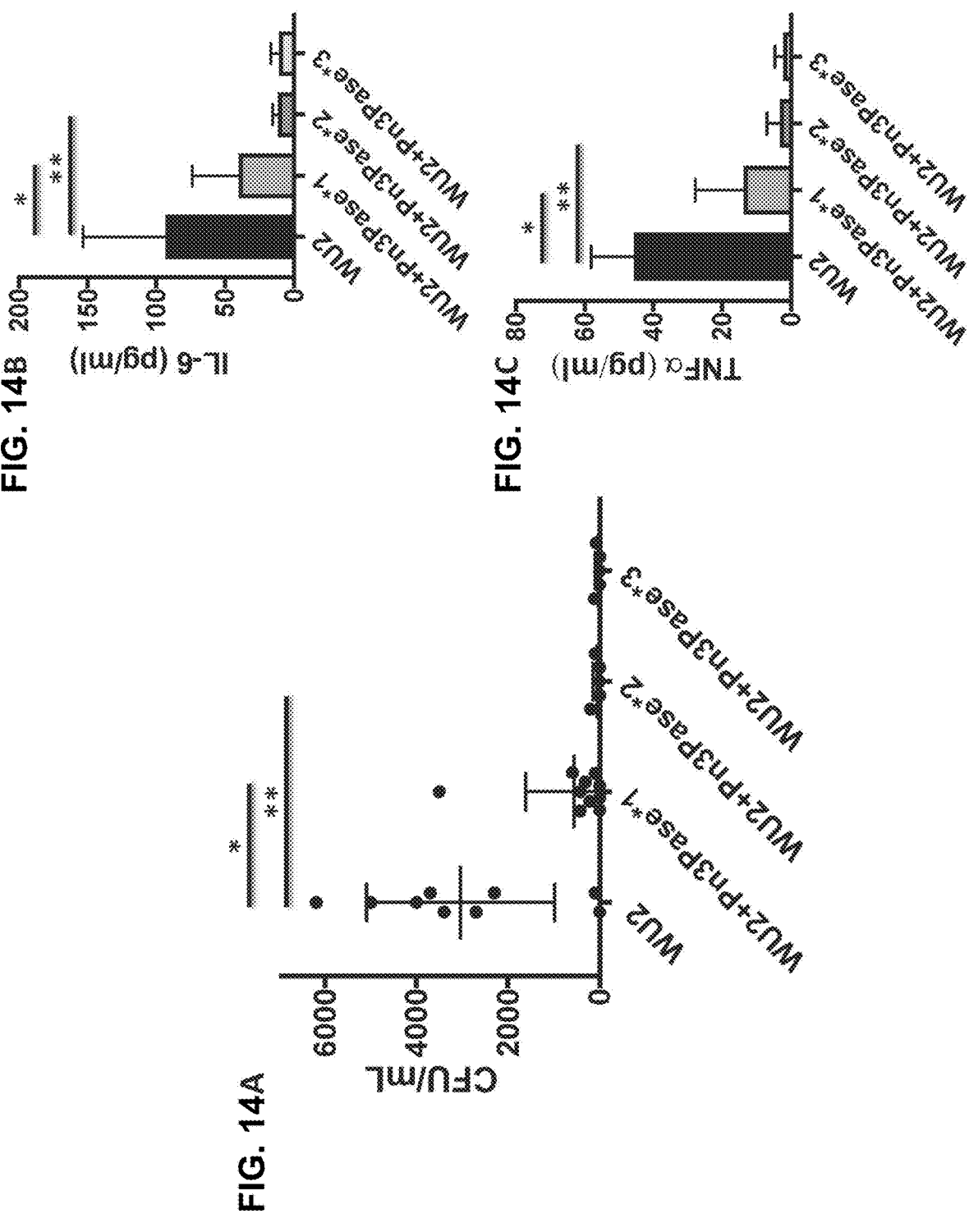
FIGS. 14A-14C show intranasal colonization with type 3 Spn. Ability of Pn3Pase treatment to reduce Spn colonization in nasopharynx of BALB/c mice.

To investigate the enzyme's protective abilities in vivo we first performed an intranasal colonization experiment with BALB/c mice. Nasal colonization by Spn is essential for transition to invasive pneumococcal disease (4, 5). It is established that the capsule of this strain is required for intranasal colonization (6). Therefore, we used the nasal colonization model to assess the ability of Pn3Pase to reduce bacterial colonization in the nasopharynx through removal of the capsule of the colonizing type 3 strain. We first confirmed that the acapsular mutant, JD908, failed to colonize the nasopharynx (data not shown). Groups of mice were then intranasally inoculated with $10^6$ log-phase wildtype (wt) encapsulated bacteria in 101 PBS. All inocula were chased with either Pn3Pase or buffer control. Groups were dosed with the enzyme at either day 0, day 0 and 3, or day 0, 3, and 7 to assess the effects of multiple administrations. Mice were euthanized, and bacterial load was quantified on day 10. Nasal lavage fluid was obtained, serially diluted, and plated to enumerate the bacterial load. Vehicle control treated mice were colonized with significantly higher bacterial loads than mice treated with only a single dose of Pn3Pase. Administration of two or three doses of Pn3Pase made the majority of the animal lavage fluid void of any viable bacterial colonies (FIG. 14A). Lung homogenates and serum samples showed no evidence of a bacterial burden (data not shown). Signature pro-inflammatory cytokine levels were measured in the nasal lavage fluid by ELISA (52). Vehicle treated mice had significantly increased levels of the cytokines IL-6 and TNFα compared to Pn3Pase treated animals, a reflection of a continued host inflammatory response to the bacterial burden in this group (FIGS. 14B-C) (52). A significant reduction in IL-6 and TNFα was observed in most animals even after a single dose of Pn3Pase on day 0. The mouse with higher bacterial load in the single dose group contributed to the increased cytokine levels in this group.

Pn3Pase Protects Mice from Lethal Challenge

Figure 15:
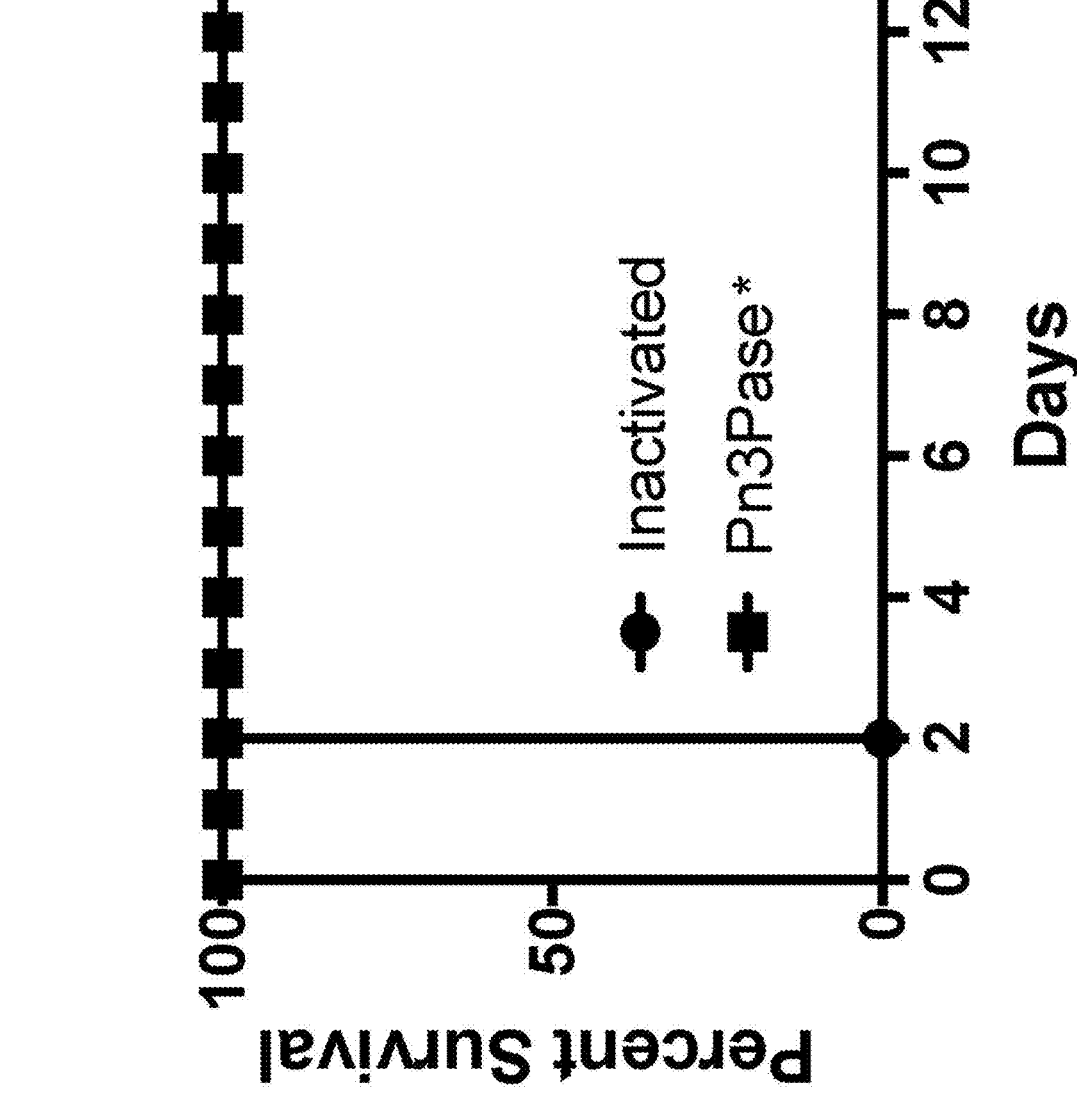
FIG. 15 shows protective ability of Pn3Pase. Assessment of ability of Pn3Pase to protect BALB/c mice from lethal challenge. Groups of mice were infected through intraperitoneal administration of 5×103 log-phase virulent type 3 Spn. Inactivated group is heat inactivated Pn3Pase. *Shown are the effect of a single dose of 5 g or 0.5 g, administered at time 0, 12, or 24 hours post infection, n=5 mice per group.

To further assess Pn3Pase for its protective abilities and evaluate the utility of Pn3Pase as a therapeutic agent, we employed an intraperitoneal (I.P.) sepsis model (53, 54). Groups of mice were infected with $5 \times 10^3$ CFU of log-phase WU2 type 3 strain of Spn. We assessed the effect of a single dose of 5 g or 0.5 g, administered at time 0, 12, or 24 hours post infection. Control groups treated with heat inactivated enzyme died within 48 hours of infection. Regardless of the enzyme dose or the timing of the administration, all treated groups displayed no signs of illness and experienced full protection from the I.P. challenge (FIG. 15).

Discussion

This study aimed to evaluate the protective role of a carbohydrate-degrading enzyme (glycoside hydrolase), Pn3Pase, targeting the CPS of the pathogenic bacterium, serotype 3 Spn. Invasive pneumococcal diseases (IPD) caused by Spn have been a major threat to human health with alarming mortality rates. Despite a global vaccination program and the use of antibiotics, Spn remains among the deadliest infectious agents worldwide. Pneumococcal vaccines are made empirically and are variably/poorly immunogenic, especially among elderly and immunocompromised individuals. Widespread use of antibiotics against IPD has led to spread of drug resistant pneumococcal strains (34, 35). This study offers an alternative targeted therapeutic approach to the shortcomings of the incumbent vaccine and antibiotic solutions to IPD.

First we demonstrated that Pn3Pase could efficiently remove the capsule from live pneumococci without having bactericidal effects on the cells. Through in vitro assays we observed that Pn3Pase treatment increases the bacterium's susceptibility to phagocytosis by a macrophage cell line. These results were promising since the capsule is a major host immune evasion component that allows Spn to resist engulfment by host phagocytes (9). We then concluded that enzyme treatment significantly increased complement-mediated killing by the neutrophils. A single dose of Pn3Pase reduced murine nasopharyngeal colonization by type 3 Spn significantly, indicating that the enzyme may function as a prophylactic measure to control colonization by this serotype in at-risk populations. Finally, an intraperitoneal challenge was performed to assess the protective capacity of Pn3Pase in a sepsis model. Notably, a single low dose of 0.5 μg administered 24 hours after infection was able to protect 100% of the challenged mice from the bacterial challenge while control treated animals did not survive longer than 48 hours. The robust protective capacity of Pn3Pase in this model demonstrates the enzymatic activity is sufficient within the host to effectively degrade the capsule even at low doses.

Given that Pn3Pase has therapeutic potential for pneumococcal infections, practical issues pertaining to the application of the enzyme such as immunogenicity, administration routes, and substrate specificity will need to be addressed (55). Our preliminary assessment of antibody titers generated against Pn3Pase in the challenge experiments observed no IgM or IgG response generated against the effective dose of the enzyme. Future studies will evaluate humoral and cellular immune responses to Pn3Pase and investigate alternative routes of administration such as intravenous for a bacteremia model, or aerosolized spray for the pneumonia model. A useful example of enzyme delivery to the respiratory tract by aerosol spray is the recombinant human deoxyribonuclease known as Pulmozyme, used to relieve airway obstruction by secreted DNA in cystic fibrosis patients (56). Another potential problem with the use of Pn3Pase as a therapeutic agent is its activity on host glycans. Relaxed substrate specificity of Pn3Pase on mammalian glycans structurally similar to Pn3P will need to be assessed.

In addition to the high potential of Pn3Pase as a therapeutic enzyme, this glycosyl hydrolase has unique properties from a structure/function point of view in that it does not fall into a currently established glycosyl hydrolase Carbohydrate Active enZYme (CAZY) family (57). Further examination of structural properties of this protein may lead to the discovery of structurally similar enzymes with activities toward other unique bacterial CPSs. Future investigations will explore the existence of enzymes for use against other prevalent pneumococcal serotypes and other encapsulated pathogenic bacteria. Based on earlier studies, the native species expressing Pn3Pase has the capacity to degrade two additional pneumococcal CPSs (58, 59). While this Pn3Pase expressing *Paenibacillus* species was isolated from the soil (26, 42, 59), it is befitting to question why this species would evolve to possess such enzymes that are capable of degrading capsules of a human pathogen. Whether these are the natural substrates for the enzymes, indicating co-evolutionary relationship, or whether other soil-dwelling microbes or plants express similar glycan residues and linkages remains to be explored.

The results presented here indicate that enzymatic hydrolysis of the CPS may be a valid alternative or complementary therapeutic approach for diseases caused by Spn and potentially other important encapsulated pathogens such as *Neisseria meningitidis* and Methicillin-Resistant *Staphylococcus aureus* (MRSA). In summary, this study serves as the first comprehensive evaluation of the protective role of a glycoside hydrolase, Pn3Pase, debilitating an otherwise lethal bacterial pathogen through targeting its capsular polysaccharide.

REFERENCES

1. Jochems S P, Weiser J N, Malley R, Ferreira D M. 2017. The immunological mechanisms that control pneumococcal carriage. PLoS Pathog 13:e1006665.
2. Austrian R. 1986. Some aspects of the pneumococcal carrier state. J Antimicrob Chemother 18 Suppl A.35-45.
3. Goldblatt D, Hussain M, Andrews N, Ashton L, Virta C, Melegaro A, Pebody R, George R, Soininen A, Edmunds J, Gay N, Kayhty H, Miller E. 2005. Antibody responses to nasopharyngeal carriage of *Streptococcus pneumoniae* in adults: a longitudinal household study. J Infect Dis 192:387-393.
4. Bogaert D, De Groot R, Hermans P W. 2004. *Streptococcus pneumoniae* colonisation: the key to pneumococcal disease. Lancet Infect Dis 4:144-154.
5. Simell B, Auranen K, Kayhty H, Goldblatt D, Dagan R, O'Brien K L, Group P C. 2012. The fundamental link between pneumococcal carriage and disease. Expert Rev Vaccines 11:841-855.
6. Magee A D, Yother J. 2001. Requirement for capsule in colonization by *Streptococcus pneumoniae*. Infect Immun 69:3755-3761.
7. Watson D A, Musher D M. 1990. Interruption of capsule production in *Streptococcus pneumoniae* serotype 3 by insertion of transposon Tn916. Infect Immun 58:3135-3138.
8. Nelson A L, Roche A M, Gould J M, Chim K, Ratner A J, Weiser J N. 2007. Capsule enhances pneumococcal colonization by limiting mucus-mediated clearance. Infect Immun 75:83-90.
9. Bruyn G A, Zegers B J, van Furth R. 1992. Mechanisms of host defense against infection with *Streptococcus pneumoniae*. Clin Infect Dis 14:251-262.
10. Winkelstein J A. 1984. Complement and the host's defense against the pneumococcus. Crit Rev Microbiol 11:187-208.
11. Winkelstein J A. 1981. The role of complement in the host's defense against *Streptococcus pneumoniae* e. Rev Infect Dis 3:289-298.
12. Geno K A, Gilbert G L, Song J Y, Skovsted I C, Klugman K P, Jones C, Konradsen H B, Nahm M H. 2015. Pneumococcal Capsules and Their Types: Past, Present, and Future. Clin Microbiol Rev 28:871-899.
13. Grabenstein J D, Klugman K P. 2012. A century of pneumococcal vaccination research in humans. Clin Microbiol Infect 18 Suppl 5:15-24.
14. MacLeod C M, Hodges R G, Heidelberger M, Bernhard W G. 1945. Prevention of pneumococcal pneumonia by immunization with specific capsular polysaccharides. J. Exp. Med. 82:445-465.
15. Wantuch P L, Avci F Y. 2018. Current status and future directions of invasive pneumococcal diseases and prophylactic approaches to control them. Hum Vaccin Immunother:1-19.
16. Avci F, Kasper D. 2010. How bacterial carbohydrates influence the adaptive immune system. Annu Rev Immunol 28:107-130.
17. Avci F. 2013. Novel strategies for development of next-generation glycoconjugate vaccines. Current Topics in Medicinal Chemistry 13:2535-2540.
18. Avci F, Li X, Tsuji M, Kasper D. 2011. A mechanism for glycoconjugate vaccine activation of the adaptive immune system and its implications for vaccine design. Nat Med 17:1602-U1115.
19. Alicino C, Paganino C, Orsi A, Astengo M, Trucchi C, Icardi G, Ansaldi F. 2017. The impact of 10-valent and 13-valent pneumococcal conjugate vaccines on hospitalization for pneumonia in children: A systematic review and meta-analysis. Vaccine 35:5776-5785.
20. Bonten M J, Huijts S M, Bolkenbaas M, Webber C, Patterson S, Gault S, van Werkhoven C H, van Deursen A M, Sanders E A, Verheij T J, Patton M, McDonough A, Moradoghli-Haftvani A, Smith H, Mellelieu T, Pride M W, Crowther G, Schmoele-Thoma B, Scott D A, Jansen K U, Lobatto R, Oosterman B, Visser N, Caspers E, Smorenburg A, Emini E A, Gruber W C, Grobbee D E.

2015. Polysaccharide conjugate vaccine against pneumococcal pneumonia in adults. N Engl J Med 372:1114-1125.

21. Tin Tin Htar M, Stuurman A L, Ferreira G, Alicino C, Bollaerts K, Paganino C, Reinert R R, Schmitt H J, Trucchi C, Vestraeten T, Ansaldi F. 2017. Effectiveness of pneumococcal vaccines in preventing pneumonia in adults, a systematic review and meta-analyses of observational studies. PLoS One 12:e0177985.

22. Harboe Z B, Dalby T, Weinberger D M, Benfield T, Molbak K, Slotved H C, Suppli C H, Konradsen H B, Valentiner-Branth P. 2014. Impact of 13-valent pneumococcal conjugate vaccination in invasive pneumococcal disease incidence and mortality. Clin Infect Dis 59:1066-1073.

23. Dagan R, Patterson S, Juergens C, Greenberg D, Givon-Lavi N, Porat N, Gurtman A, Gruber W C, Scott D A. 2013. Comparative immunogenicity and efficacy of 13-valent and 7-valent pneumococcal conjugate vaccines in reducing nasopharyngeal colonization: a randomized double-blind trial. Clin Infect Dis 57:952-962.

24. Gruber W C, Scott D A, Emini E A. 2012. Development and clinical evaluation of Prevnar 13, a 13-valent pneumococcal CRM197 conjugate vaccine. Ann N Y Acad Sci 1263:15-26.

25. Richter S S, Heilmann K P, Dohrn C L, Riahi F, Diekema D J, Doern G V. 2013. Pneumococcal serotypes before and after introduction of conjugate vaccines, United States, 1999-2011(1.). Emerg Infect Dis 19:1074-1083.

26. Middleton D R, Zhang X, Wantuch P L, Ozdilek A, Liu X, LoPilato R, Gangasani N, Bridger R, Wells L, Linhardt R J, Avci F Y. 2018. Identification and characterization of the Streptococcus pneumoniae type 3 capsule-specific glycoside hydrolase of Paenibacillus species 32352. Glycobiology 28:90-99.

27. Li G, Li L, Xue C, Middleton D, Linhardt R J, Avci F Y. 2015. Profiling pneumococcal type 3-derived oligosaccharides by high resolution liquid chromatography-tandem mass spectrometry. Journal of chromatography. A 1397:43-51.

28. Kieninger D M, Kueper K, Steul K, Juergens C, Ahlers N, Baker S, Jansen K U, Devlin C, Gruber W C, Emini E A, Scott D A, group s. 2010. Safety, tolerability, and immunologic noninferiority of a 13-valent pneumococcal conjugate vaccine compared to a 7-valent pneumococcal conjugate vaccine given with routine pediatric vaccinations in Germany. Vaccine 28:4192-4203.

29. Jackson L, El Sahly H, George S, Winokur P, Edwards K, Brady R, Rouphael N, Keitel W, Mulligan M, Burton R, Nakamura A, Ferreria J, Nahm M. 2018. Randomized clinical trial of a single versus a double dose of 13-valent pneumococcal conjugate vaccine in adults 55 through 74 years of age previously vaccinated with 23-valent pneumococcal polysaccharide vaccine. Vaccine 36:606-614.

30. Briles D E, Crain M J, Gray B M, Forman C, Yother J. 1992. Strong association between capsular type and virulence for mice among human isolates of Streptococcus pneumoniae. Infect Immun 60:111-116.

31. Weinberger D M, Harboe Z B, Sanders E A, Ndiritu M, Klugman K P, Rückinger S, Dagan R, Adegbola R, Cutts F, Johnson H L, O'Brien K L, Scott J A, Lipsitch M. 2010. Association of serotype with risk of death due to pneumococcal pneumonia: a meta-analysis. Clin Infect Dis 51:692-699.

32. Martens P, Worm S W, Lundgren B, Konradsen H B, Benfield T. 2004. Serotype-specific mortality from invasive Streptococcus pneumoniae disease revisited. BMC Infect Dis 4:21.

33. Sugimoto N, Yamagishi Y, Hirai J, Sakanashi D, Suematsu H, Nishiyama N, Koizumi Y, Mikamo H. 2017. Invasive pneumococcal disease caused by mucoid serotype 3 Streptococcus pneumoniae: a case report and literature review. BMC Res Notes 10:21.

34. Kim L, McGee L, Tomczyk S, Beall B. 2016. Biological and Epidemiological Features of Antibiotic-Resistant Streptococcus pneumoniae in Pre- and Post-Conjugate Vaccine Eras: a United States Perspective. Clin Microbiol Rev 29:525-552.

35. Li Y, Metcalf B J, Chochua S, Li Z, Gertz R E, Walker H, Hawkins P A, Tran T, Whitney C G, McGee L, Beall B W. 2016. Penicillin-binding protein transpeptidase signatures for tracking and predicting β-lactam resistance levels in Streptococcus pneumoniae MBio 7.

36. Metcalf B J, Gertz R E, Gladstone R A, Walker H, Sherwood L K, Jackson D, Li Z, Law C, Hawkins P A, Chochua S, Sheth M, Rayamajhi N, Bentley S D, Kim L, Whitney C G, McGee L, Beall B, team ABCs. 2016. Strain features and distributions in pneumococci from children with invasive disease before and after 13-valent conjugate vaccine implementation in the USA. Clin Microbiol Infect 22:60.e69-60.e29.

37. Obolski U, Lourenço J, Thompson C, Thompson R, Gori A, Gupta S. 2018. Vaccination can drive an increase in frequencies of antibiotic resistance among nonvaccine serotypes of. Proc Natl Acad Sci USA 115:3102-3107.

38. Zhao C, Li Z, Zhang F, Zhang X, Ji P, Zeng J, Hu B, Hu Z, Liao K, Sun H, Zhang R, Cao B, Zhuo C, Jia W, Mei Y, Chu Y, Xu X, Yang Q, Jin Y, Fu Q, Li H, Wang L, Ni Y, Liang H, Wang H. 2017. Serotype distribution and antibiotic resistance of Streptococcus pneumoniae isolates from 17 Chinese cities from 2011 to 2016. BMC Infect Dis 17:804.

39. Avery O T, Dubos R. 1930. The specific action of a bacterial enzyme on pneumococci of type III. Science 72:151-152.

40. Dubos R, Avery O T. 1931. Decomposition of the capsular polysaccharide of pneumococcus type III by a bacterial enzyme J Exp Med 54:51-71.

41. Avery O T, Dubos R. 1931. The protective action of a specific enzyme against type III pneumococcus infection in mice. J Exp Med 54:73-89.

42. Middleton D R, Lorenz W, Avci F Y. 2017. Complete genome sequence of the bacterium Bacillus circulans Jordan strain 32352. Genome Announcements 5:e00289-17

43. Burton R L, Nahm M H. 2012. Development of a fourfold multiplexed opsonophagocytosis assay for pneumococcal antibodies against additional serotypes and discovery of serological subtypes in Streptococcus pneumoniae serotype 20. Clin Vaccine Immunol 19:835-841.

44. Daniels C C, Kim K H, Burton R L, Mirza S, Walker M, King J, Hale Y, Coan P, Rhee D K, Nahm M H, Briles D E. 2013. Modified opsonization, phagocytosis, and killing assays to measure potentially protective antibodies against pneumococcal surface protein A. Clin Vaccine Immunol 20:1549-1558.

45. Fleck R A, Romero-Steiner S, Nahm M H. 2005. Use of HL-60 cell line to measure opsonic capacity of pneumococcal antibodies. Clin Diagn Lab Immunol 12:19-27.

46. Romero-Steiner S, Frasch C E, Carlone G, Fleck R A, Goldblatt D, Nahm M H. 2006. Use of opsonophagocytosis for serological evaluation of pneumococcal vaccines. Clin Vaccine Immunol 13:165-169.

47. Song J Y, Moseley M A, Burton R L, Nahm M H. 2013. Pneumococcal vaccine and opsonic pneumococcal antibody. J Infect Chemother 19:412-425.

48. Middleton D R, Sun L, Paschall A V, Avci F Y. 2017. T cell-mediated humoral immune responses to type 3 capsular polysaccharide of *Streptococcus pneumoniae*. J Immunol 199:598-603.

49. Craig A, Mai J, Cai S, Jeyaseelan S. 2009. Neutrophil recruitment to the lungs during bacterial pneumonia. Infect Immun 77:568-575.

50. Lu Y J, Gross J, Bogaert D, Finn A, Bagrade L, Zhang Q, Kolls J K, Srivastava A, Lundgren A, Forte S, Thompson C M, Harney K F, Anderson P W, Lipsitch M, Malley R. 2008. Interleukin-17A mediates acquired immunity to pneumococcal colonization. PLoS Pathog 4:e1000159.

51. Zhang Z, Clarke T B, Weiser J N. 2009. Cellular effectors mediating Th17-dependent clearance of pneumococcal colonization in mice. J Clin Invest 119:1899-1909.

52. Blanchette-Cain K, Hinojosa C A, Akula Suresh Babu R, Lizcano A, Gonzalez-Juarbe N, Munoz-Almagro C, Sanchez C J, Bergman M A, Orihuela C J. 2013. *Streptococcus pneumoniae* biofilm formation is strain dependent, multifactorial, and associated with reduced invasiveness and immunoreactivity during colonization. MBio 4:e00745-00713.

53. Briles D E, Nahm M, Schroer K, Davie J, Baker P, Kearney J, Barletta R. 1981. Antiphosphocholine antibodies found in normal mouse serum are protective against intravenous infection with type 3 *Streptococcus pneumoniae*. J Exp Med 153:694-705.

54. Chiavolini D, Pozzi G, Ricci S. 2008. Animal models of *Streptococcus pneumoniae* disease. Clin Microbiol Rev 21:666-685.

55. Fenton M, Ross P, McAuliffe O, O'Mahony J, Coffey A. 2010. Recombinant bacteriophage lysins as antibacterials. Bioeng Bugs 1:9-16.

56. Fuchs H J, Borowitz D S, Christiansen D H, Morris E M, Nash M L, Ramsey B W, Rosenstein B J, Smith A L, Wohl M E. 1994. Effect of aerosolized recombinant human DNase on exacerbations of respiratory symptoms and on pulmonary function in patients with cystic fibrosis. The Pulmozyme Study Group. N Engl J Med 331:637-642.

57. Henrissat B, Bairoch A. 1996. Updating the sequence-based classification of glycosyl hydrolases. Biochem J 316 (Pt 2):695-696.

58. Shaw M, Sickles G M. 1950. Production of specific pneumococcus carbohydrate-splitting enzymes in media to which the specific substrate was not added. J Immunol 64:27-32.

59. Sickles G M, Shaw M. 1934. A systematic study of microorganisms which decompose the specific carbohydrates of the pneumococcus. J Bacteriol 28:415-431.

60. Dillard J P, Vandersea M W, Yother J. 1995. Characterization of the cassette containing genes for type 3 capsular polysaccharide biosynthesis in *Streptococcus pneumoniae*. J Exp Med 181:973-983.

61. Dillard J P, Yother J. 1994. Genetic and molecular characterization of capsular polysaccharide biosynthesis in *Streptococcus pneumoniae* type 3. Mol Microbiol 12:959-972.

62. Hammerschmidt S, Wolff S, Hocke A, Rosseau S, Müller E, Rohde M. 2005. Illustration of pneumococcal polysaccharide capsule during adherence and invasion of epithelial cells. Infect Immun 73:4653-4667.

63. Hyams C, Camberlein E, Cohen J M, Bax K, Brown J S. 2010. The *Streptococcus pneumoniae* capsule inhibits complement activity and neutrophil phagocytosis by multiple mechanisms. Infect Immun 78:704-715.

64. Puchta A, Verschoor C P, Thurn T, Bowdish D M. 2014. Characterization of inflammatory responses during intranasal colonization with *Streptococcus pneumoniae* J Vis Exp:e50490.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. Supplementary materials referenced in publications (such as supplementary tables, supplementary figures, supplementary materials and methods, and/or supplementary experimental data) are likewise incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The disclosure is not limited to the exact details shown and described, for variations obvious to one skilled in the art will be included within the disclosure defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present disclosure. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

---

What is claimed is:

1. A genetically modified cell comprising a mature Pn3Pase protein, wherein the protein has Pn3Pase activity, wherein the cell comprises an exogenous polynucleotide comprising a coding region encoding a Pn3Pase protein.

2. A genetically modified cell comprising a polynucleotide comprising a coding region, wherein the coding region comprises a nucleotide sequence encoding a mature Pn3Pase protein, wherein the protein has Pn3Pase activity, and wherein the protein comprises a heterologous amino acid sequence.

3. The genetically modified cell of claim 1 wherein the protein has at least 80% identity with the amino acid sequence set forth in SEQ ID NO:2, wherein the amino terminal amino acid is selected from any one of residues 2 to 64 of SEQ ID NO:2 and the carboxy terminal amino acid is residue 1545 of SEQ ID NO:2.

4. The genetically modified cell of claim 3 wherein the protein has at least 80% identity with amino acids 41-1545 of SEQ ID NO:2.

5. The genetically modified cell of claim 1 wherein the cell is a eukaryotic cell.

6. The genetically modified cell of claim 5 wherein the cell is a mammalian cell, a yeast cell, or an insect cell.

7. The genetically modified cell of claim 1 wherein the cell is a prokaryotic cell.

8. The genetically modified cell of claim 7 wherein the cell is *E. coli.*

9. The genetically modified cell of claim 1 wherein the protein comprises a heterologous amino acid sequence.

10. The genetically modified cell of claim 9 wherein the heterologous amino acid sequence comprises a tag.

11. A composition comprising the genetically modified cell of claim 1.

12. The genetically modified cell of claim 1, wherein the exogenous polynucleotide comprises an expression vector.

13. The genetically modified cell of claim 1, wherein the exogenous polynucleotide comprises a marker sequence.

14. The genetically modified cell of claim 13, wherein the marker sequence renders the genetically modified cell resistant to an antibiotic.

15. A method comprising incubating in a culture medium the genetically modified cell of claim 4 under suitable conditions for expression of a Pn3Pase protein.

16. The method of claim 15, wherein suitable conditions comprise a type-3 polysaccharide Pn3P.

17. The method of claim 15, further comprising isolating the Pn3Pase protein from the cell or medium.

18. The method of claim 17, wherein isolating the Pn3Pase protein from the cell comprises lysing the cell.

19. The method of claim 17, wherein isolating the Pn3Pase protein comprises purifying the Pn3Pase protein.

* * * * *

SEQUENCE LISTING

```
Sequence total quantity: 25
SEQ ID NO: 1          moltype = DNA   length = 4638
FEATURE               Location/Qualifiers
```

-continued

```
source              1..4638
                    mol_type = genomic DNA
                    organism = Paenibacillus sp.
SEQUENCE: 1
atggctattg gaacatcata taggctgcgt caggcattga accgatcctg tatcgcgctt   60
gcggccagtg ccttgctggc atcggctgca gcaagcttca ccgcaggaac gactcatgcg  120
gcacccgtga atctggaagc ggattatgcc ttaagtgaag ggcagcttgt ccgcacggag  180
caattcaaca atacgaatta cacgccgctt ccggttcatg tcgtcgatga actcaaaggg  240
atccggacca aggtcgtaag agattttgtt aaaattaatt ggtactacaa caaggatgag  300
gcgaacagcg attatttggc ttattccatc gacgacccgc gtaacgcgac gaacccggat  360
ttacagcatg gccgcaagga aacgtatgat ttcatgtccc agtttaccga tggcattctc  420
ctatctctcg cttattccta tggaggtgac gcgaatccgc agaaaaaccg cctcctagcc  480
ggcgagaccg aaatgaactg gcctgaattc gacaaggcga tgaagaaaat catttatacg  540
ttgaaggaga aaaatccgaa gatcgaatat atcgaggtgg gcaacgagcc gaacctggag  600
cctgcctatt atggacatgt gaaggatgat attcccggct acatgcgcat gtatcagggc  660
atgtcggaag cggtaaaatg ggtaaacgca cagggcttgg ccgggcagcc gctgaaagta  720
ggcggaccgg tattatccgg ctacaatttc gagaagcaga agcagttcgt cgatcttgcc  780
tacgccgcaa gctatcaggt cgattttgtg tcatggcaac gataccagga ggacgtgcgg  840
atgaacgaaa cgcaggaaat cgaaatgaaa agctatctgc acaagtttta tccgaatgct  900
ataaccattg ttagcgaata cggctggaag ggggcgggg gcttaagtga tccgacgaac  960
aacgtcggac tggcgaagca agcggcgttt atgacggact cggcatccta ttatgcccgt 1020
ggagggacgg atattccgat gaactgggta gcggtccata cactgaatgc gtatttcaag 1080
aaccagttcg atgtcgacta tgctttaagc aatgggggata cgacgaattg gcagacattt 1140
atgaatccta atccaagggc tttacaatat ttgaacctgc gcgggtggag ggagtcggca 1200
tcgacctcca agccgatgaa gatcaaggaa attcgttttt ttgacagcag taacaacccg 1260
attccaatcc cgaatccggc aaacgacccg aatattgcgt cggttacgga cggtgacgat 1320
gcgacgcagt ttatccaagc agactactgg acctggctca agtttgatct ggggccatcg 1380
gctcccggga ttgccagggt tgatatcaag tgggggaatc ccgatatcaa caccttccag 1440
ctcattggca ctagtgataa attgaaatat tacgaggcgc tgggccgcac tttctacacc 1500
ccgtatttta acacaatgcg gatgttcgcc cggctcgggg acacccgggt gaaagcaacc 1560
ggcggcagca gtgacatcta tgggacacgg atgctggcga cgaagaacag cgattccaaa 1620
gcgacgatga tggtgtggaa caaacaggga gacggggcgg cctcatccaa tgtcagcatc 1680
gatgtgaagc atctgccgcc aggctttgaa gggaagagtg tacggatcaa aaagtatttg 1740
gtcgacgaga cccatagcaa ttatgcctac aacaaaatcg acgagctcca gttgttcgac 1800
gaaaccatag cgaacacggc ggacaatctg acgattaacg ctacgttgaa tagaaatgcg 1860
gtaatgctga tagagctgga ggcggttgat cctagcatcc aaaatatcgt gtctgccggc 1920
aaggaagtta cctctacgac aggaatgacg aatatgccgg cgctggtgga cggcaatagt 1980
ctgactgctg ctgtcgcagc cgatagcagc tatccgcaaa ctatacaaat ggatctcggc 2040
agaccctatg agttatcagg gatgcaaatc gattggacga acagcgcatc gagagatttc 2100
agctacgcaa tagcgacgag cttggatggc acgtcgtacc atacggtagc ggatcaaacc 2160
gacccggctt ccgcagtccc aagagggaac agtttggact ggttccaaac caaggcgcgg 2220
tatgtgaagc tgacggtgac gcgctccacc ttcgatggcc cgctatcgat taacgatgta 2280
aaggtttttg ccgaagcgct gtacaaaaac gggttcgaca ccaccgagga taagaatgcg 2340
atggcggcat ggacgacggt tggctttgga tcgaaatcca ccccatggac caccgtgacg 2400
gacagtgttt accataacac attcgtgcaa ccgatggacc tattcagcac gacacctagc 2460
ttcgccattt ttggtgacag tcttaaggat tatggagtgg aagcgcgggt cagaactacg 2520
gacagtggaa acgtgcaaat ggggcttatt gcccgacgga ccgattacaa taacttgtat 2580
tacttcaagc tgtaccgaag cagctccgcg catcaggcag tgctggagaa gcgcgtcaat 2640
ggaacgacaa ccgtgcttaa gtcggtggat ttggctgatc cgattcagtc gaaccgctgg 2700
tataggctga atttggaagc tgtcggaaca acgctgcgag cttctattga cggtgttcag 2760
gttatcgagc ttacggatgc cagccgggct tccggtaaat tcgggctgcg aagccatgaa 2820
tccatcgccg gcttcgacga tgtcaaagtg tatccgattg ttccgctgct tggcgatatt 2880
aaggtgaaca gcgtatctat tgagggcttc catccgcatt tgaacaacta cactgtactt 2940
gtcccatcga cgagctctgc agtaaccgtg acggcaaccg tctacggtac ggccaatacc 3000
gtggcgtccc cggcctccgg gcaggtgacc ttcgacgcgg ttggccaaga gaggtcgtac 3060
acagtagctg cgctgtcgac tgaaggcaat ggggcgaatt attacaagat aaacttgcgg 3120
acggcaagcg ccgatacatc gcttagcaac ctgaggctgt cggtcattac ggacgctctg 3180
acagccccgg gccaacaatt acccgaatcg atcgttgctc tggttccggg tcaaacggaa 3240
tacacgattc acgttccttc ccgtacggct tatgtcaagg tggtagaggc gatcccgacg 3300
gtaagcaatg tggcttcagt tcaaatcact aacgcaactt tggtgaacgg ctcgggtacc 3360
gcaacggtaa aagtaacctc cgaagccgga acgacggcgg aatatatgct gaatatccgg 3420
gcgaacccgg aggcggctgc cgggacggtg ctgtacgaag aaaatttga gagcggagct 3480
tacaatcaag acgcagcgac cggttggaat aacggtgccg taccgaatgg tgcagcttca 3540
catctacgcg ttgcggatga ggatcagggc aaggtgcgca aggccgcat tcaagtgagc 3600
atggccttta cggtcggtca aagcggttgg acagattacg atgtaagggc cagagttaaa 3660
gcgcaggcca gcccgtcact gccaggcatt attgcgcgcg catccgacga tgccaaaaac 3720
ttttatatgc tgcgcattca taacggcacg aatggactgc ctggcggaag cacggggtat 3780
gtcattcttg gccgtgtcgt gaacgggacg ctccgcgagc tggacagcaa aaaaatccca 3840
tacccgtatg tggtcggtaa ctggtatcag cttcgtcttg tcgtcgatag taatcggatc 3900
aaaggctatg tggacgatag cctgatctat gacgaagtag ataacggatc gttattcccg 3960
acgaatcctc ctgcactgat gcaaggcaag gcggggatcc gggtggcaaa ccaggcagcc 4020
cgcatcgatg attttcaggt atcccatctt gctgccctac ccgcagattc ggtgaagccg 4080
gtgataaccc tgaacgggcc ggcagtggtt gaagtattgc tggcagcac gtatacggat 4140
gcaggacgca cggcggcgga tgatgtggac ggcgatctga caagccgcat tcaagtgagc 4200
ggcagtgtgg acacgtcgac gccaggaacg tacacgctgg tctataccgt aatggacaac 4260
gcacataatg tagcggaccc ggttgtacgc actgtaacgg taaccgctgc gggggataag 4320
ccgtttactg tcattgcaaa tggcgggctg aaccggacga acggtttgag tgctaaggtc 4380
gacgttaccg gcacacccgg ctcggtagat catgcgggta gggaagtcgt ttactttcag 4440
cttcttaagg gcagcactcc cgtatcccat gttgcgttgg aaagcgagct tacgaatggc 4500
```

```
ggcagcctga caggccattt cgatgtgccg gatgctgaag agggcactta tacggttcat   4560
gtgtttatca tcgatatgct cgactctata gagggatcct tgccgattcc gttatcgaat   4620
aaggtgatcg tggagtag                                                  4638

SEQ ID NO: 2             moltype = AA   length = 1545
FEATURE                  Location/Qualifiers
source                   1..1545
                         mol_type = protein
                         organism = Paenibacillus sp.
SEQUENCE: 2
MAIGTSYRLR QALNRSCIAL AASALLASAA ASFTAGTTHA APVNLEADYA LSEGQLVRTE   60
QFNNTNYTPL PVHVVDELKG IRTKVVRDFV KINWYYNKDE ANSDYLAYSI DDPRNATNPD   120
LQHGRKETYD FMSQFTDGIL LSLAYSYGGD ANPQKNRLLA GETEMNWPEF DKAMKKIIYT   180
LKEKNPKIEY IEVGNEPNLE PAYYGHVKDD IPGYMRMYQG MSEAVKWVNA QGLAGQPLKV   240
GGPVLSGYNF EKQKQFVDLA YAASYQVDFV SWHRYQEDVR MNETQEIEMK SYLHKFYPNA   300
ITIVSEYGWK GGGGLSDPTN NVGLAKQAAF MTDSASYYAR GGTDIPMNWV AVHTLNAYFK   360
NQFDVDYALS NGDTTNWQTF MNPNPRALQY LNLRGWRESA STSKPMKIKE IRFFDSSNNP   420
IPIPNPANDP NIAAVTDGDD ATQFIQADYW TWLKFDLGPS APGIARVDIK WGNPDINTFQ   480
LIGTSDKLKY YEALGRTFYT PYFNTMRMFA RLGDTRVKAT GGSSDIYGTR MLATKNSDSK   540
ATMMVWNKQG DGAASSNVSI DVKHLPPGFE GKSVRIKKYL VDETHSNYAY NKIDELQLFD   600
ETIANTADNL TINATLNRNA VMLIELEAVD PSIQNIVSAG KEVTSTTGMT NMPALVDGNS   660
LTAAVAADSS YPQTIQMDLG RPYELSGMQI DWTNSASRDF SYAIATSLDG TSYHTVADQT   720
DPASAVPRGN SLDWFQTKAR YVKLTVTRST FDGPLSINDV KVFAEALYKN GFDTTEDKNA   780
MAAWTTVGFG SKSTPWTTVT DSVYHNTFVQ PMDLFSTTPS FAIFGDSLKD YGVEARVRTT   840
DSGNVQMGLI ARATDYNNLY YFKLYRSSSA HQAVLEKRVN GTTTVLKSVD LADPIQSNRW   900
YRLNLEAVGT TLRASIDGVQ VIELTDASRA SGKFGLRSHE SIAGFDDVKV YPIVPLLGDI   960
KVNSVSIEGF HPHLNNYTVL VPSTSSAVTV TATVYGTANT VASPASGQVT FDAVGQERSY   1020
TVAALSTEGN GANYYKINLR TASADTSLSN LRLSVITDAL TAPGQQLPES IVALVPGQTE   1080
YTIHVPSRTA YVKVVEAIPT VSNVASVQIT NATLVNGSGT ATVKVTSEAG TTAEYMLNIR   1140
ANPEAAAGTV LYEENFESGA YNQDAATGWN NGAVPNGAAS HLRVADEDQG KVLEKYTTTS   1200
MAFTVGQSGW TDYDVRARVK AQASPSLPGI IARASDDAKN FYMLRIHNGT NGLPGGSTGY   1260
VILGRVVNGT LRELDSKKIP YPYVVGNWYQ LRLVVDSNRI KGYVDDSLIY DEVDNGSLFP   1320
TNPPALMQGK AGIRVANQAA RIDDFQVSHL AALPADSVKP VITLNGPAVV EVLAGSTYTD   1380
AGATAADDVD GDLTSRIQVS GSVDTSTPGT YTLVYTVMDN AHNVADPVVR TVTVTAAGDK   1440
PFTVIANGGL NRTNGLSAKV DVTRTPGSVD HAGREVVYFQ LLKGSTPVSH VALESELTNG   1500
GSLTGHFDVP DAEEGTYTVH VFIIDMLDSI EGSLPIPLSN KVIVE                   1545

SEQ ID NO: 3             moltype = DNA   length = 22
FEATURE                  Location/Qualifiers
source                   1..22
                         mol_type = genomic DNA
                         organism = Paenibacillus sp.
SEQUENCE: 3
tcgataccct tggtgccgaa gt                                              22

SEQ ID NO: 4             moltype = AA   length = 1581
FEATURE                  Location/Qualifiers
source                   1..1581
                         mol_type = protein
                         organism = Paenibacillus sp.
SEQUENCE: 4
MNNMISRKGW KQAKRPFSAL TAGMLAVSMA LGLAPAFPET AQAEVSPTAQ VLTADYGTSA   60
GPLIRTEQFN NTNYAPLPVH VVDELKGIKT KIVRDFVKIN WYYNKDPNNS DLLAYSIETP   120
ENLETNPDLQ HGRKETYDFM GQFADSILIS LAYSYGGDTN PGKNRLLSGE TTMNWDEYDK   180
AMRVIIKTLK EKNPKLEYIE VGNEPNLEPA YFGHVKDDIP GYMRMYEGMS KAVVWVNQQL   240
GLNDTFGSNG VRLKVGGPVL SGYNFAKQKE FVDIAYQNHY QVDFVSWHRY RQEITENETQ   300
AIQMRNYLSD KYPDATLIVS EYGWKGGGGL TDSTNNVALA KQAAFMTDSA YFYERGGVDI   360
PMNWVAVHTL NAYFKNQFDV DYALSNGTVG WQEFNSNYTD PVRYMNLRGW RESATTSGRQ   420
VKIQEIEFYD PAGNKIAVPN TAGDPLIAVA TDGDESTQFQ QSDYWTWLRF DLGAEYQISK   480
IRIKWGDSQV YKFQVVGTSD KLKYHELLGK TFFTPYFNTM RMLSRLGDEK VAVTGSDTGN   540
TGVRLLATKN SDSKATMMVW NHQLDGKASK EVSVQKNLP ASFQGKSIRY KKYLVDATHS   600
NYAYNKNDSL EVVGQGTMNI TGTEIFNETL TPNAVMLIEL EAVDSSINNI VSAGKTATGD   660
LQNLAALVDG DERTSAAAAN NSYPQSVVID LERNFTVSGA EIKWSNAELQ SYHYSISTST   720
DGGSYSTVVD STYGAWSKGS SLHWFPATAR YVKLTVTGSY TGQPLSIDDI SIFADGLYKN   780
SFETPEERDL SAWKLRGYGN KYTAWDFGTD TVTGNTYAVP HETFGDTSDN FGFFGDNSWA   840
DYGIEARVKI DNPAHTGDVK MGVTARAGKG RADEHRNLHY SLLLVRGAGT SKLVLQRDNT   900
DMPSGKKNIE LDSVVLDSID PTRWYTLRLE AVGDNLKGYL DGTLMVEYTD NNVYDGNPAR   960
LSAGWAGVRG SKTKVQFDDI HVYPIMPLLG DIQVNGASIS GFNPLKNEYE VKLAGPGSDK   1020
ATVTGTVYGG ANAVVYPASS GELALGGTGE NVVHMISSLS TAGNGATYYK VSLRKASEDA   1080
TLSSLKLSVI PDSGAYNPNE LAPGDILLIP GVYEYDVKIP SRTAYVSVKE ALPTVSNLAT   1140
AVAANTAIVN GQGTITVDVT AESGKIQRYT LHLTANEEAP LGTILYEENF ENGSYNQDAS   1200
TGWRNMDNTQ GQHLRVADDV SGKVLEKHTN DNMPFVVGNS SWTNYEVRAR VRATADTGLP   1260
GIIARASDDA RNFYMLRIHN GENNLAGGST GYIALGRVVN NSLKESAIKK PPPYEEGKWY   1320
QLRLIVNGNR LIGYVDDKLV FDVTDTGSGL FPDNPPPLTQ GKAGIRVANR PAQIDDYVVA   1380
LLPGDNTPVP DVVKPVITLN GDGAISIPVG SEYTDAGATA TDNVDGDLTA AIAVTGQVNT   1440
AVPGVYTLRY NVSDAAGNAA NEVIRTVTVF AVIGEGKSFV VTGGLVDQAQ GLTARVNVIP   1500
VAGAQVHDGD EVVYFQLLKG NTPVSYVALK SDITDLTTFV AHFDVPDPEN TAYSIRVLVV   1560
DQLFPANGEL PAALSDKVVL D                                              1581
```

```
SEQ ID NO: 5            moltype = AA   length = 1463
FEATURE                 Location/Qualifiers
source                  1..1463
                        mol_type = protein
                        organism = Paenibacillus sp.
SEQUENCE: 5
MGLLKKHCAA LTAAIMLTSA AVSLAPQAAQ AASMNMEADY AVSEGPLVRT EQFNNTNYTP    60
LPVHVVDELK GIKTKVVRDF VKINWYYNKD SANSDYLAYS IDDARNATNP DLLSARKETY   120
DFMSQFSDSL LISLAYSYGG DANPEKNRLI AGETTMNWPE FDKAMKKIIF TLKEKNPELE   180
YIEVGNEPNL EPAFYGHTKE DIPGYMRMYQ GMSEAVKWVN TQGLAGQSVK VGGPVLSGYN   240
FDKQKQFVDI AYANGYQVDF VSWHRYQEDV RMNETQEIEM KGYLHRFYPN ATTIVSEYGW   300
KGGGDLSDAT NNVGLAKQAA FMTDSAYFYA RGGTDIPMNW VAVHTLNAYF KNQFDVDYAL   360
STGDTTNWQS FTNSDPRSLQ YLNLRGWRES ASTSKPMKIK EIRFFDSNNN PIPIPNVLND   420
PSIAAVTDND DATQFTQSDY WTWLKFDLGT NAPAVARVDI KWGNTDINTF QLIGTSDKLK   480
YYEVLGHTFF TPYFNTMRMF AQLGDTRVKT SGGSMEIYGT RMLATKNSDT KATMMVWNKQ   540
GDGTASANVD ISVKNLPAGF QGKSVRYKKL LVDESHSNHA YNKRDDLQMV DEGIVNLTDT   600
IVLSQTLEKN AVMLIELEAV DPSIKNIVSA GKAVTLSPGM TGGANLVDGY DTTAAVAATN   660
TYPQTVTVDL GKSYQLAGMG IDWTNSASRG YTYTIESSLD GTHFTLASDM TFSSNPTYVP   720
PLGNSLAWFT GKARYVKLTV TGSTYDGPLS INEVKVFADG MYKNGFESVA DRDTSAWTMT   780
GYSSVSTPWT FATDSVTNNT YAIPVSTYGT TPSFAILGDD MKDYGVEARV KVANSSYAGN   840
VQMGLLARAS TYNSHYYFKL MRTNTTNQAI LEKRINGTTT VLATVDLPAA IDSSKWYKLN   900
LETIGTAIKG YVDGVLVFDT TDTSRTSGKF GLRSHDALAS FDDVRVYPIV PLLGSIKVDG   960
VIINGFDPRI NSYTVLVPSS TSTVTVTGSA YGTGSIAVLP ASGQVTFDAV GQEKTYMIAA  1020
LSSEGNGANY YLLRLKQASS DATLSSLRLS VVTDPLTSPG QKLPAMSIAL IPGQMNYTIH  1080
VPSRTNYVKV VEAVPTASNV ATAQISDGVM VNGTGTAKVT VTSEAGTTSV YTLNLVANAE  1140
APTGAVLYQE NFDNGSYNSD PSFGWNNGAT PNAASSHLRV VDEEQGKVLE KYTTTSMAFT  1200
VGQSAWTNYD VRARVKAQVG TALPGVIARA SDDAKNFYML RIHNGTNGLA GGSTGYVALG  1260
RMVNSSLKEL DSKKIPYPYI VGNWYQLRLV VEGNHLKGYV DDNLIFDEID NGALFSSNPP  1320
TLIQGKAGIR VANQAARIDD FLVTELTDDV VVVPPVETLL PFTLEGQLNR SNGLNASVLV  1380
NRAANAADHP GTEVVFFQLL QGTTPVSYVA MESEIGAGNR VAGHFDVPDP ENMSYHVHAF  1440
VVSSWDLLNE SLPLSLSNKL DLE                                          1463

SEQ ID NO: 6            moltype = AA   length = 1463
FEATURE                 Location/Qualifiers
source                  1..1463
                        mol_type = protein
                        organism = Paenibacillus sp.
SEQUENCE: 6
MGLLKKHYAA LTAALMLTSA AVSFAPQSVH AASVNMEADY AVSEGPLVRT EQFNNTNYTP    60
LPVHVVDELK GIKTKVVRDF VKINWYYNKD SANSDYLAYS IDDARNATNP DLLSARKETY   120
DFMSQFSDSL LISLAYSYGG DANPEKNRLI AGETTMNWIE FDKAMKKIIY TLKEKNPELE   180
YIEVGNEPNL EPAFYGHTKE DIPGYMRMYQ GMSEAVKWVN TQGLTGQSVK VGGPVLSGYN   240
FDKQKQFVDI AYANGYQVDF VSWHRYQEDV RMNETQEIQM KTYLHQFYPN ATTIVSEYGW   300
KGGGGLSDAT NNVGLAKQAA FMTDSAYFYA RGGTDIPMNW VAVHTLNAYF KNQFDVDYAL   360
SNGDTTNWQS FTNSDPRSLQ YLNLRGWRES ASTSKPMKIK EIRFFDSSNN PIQIPNVIND   420
PSIAAVTDND DATQFTQSDY WTWLKFDLGA NAPAIARVDI KWGNTDINTF QLIGTSDKLK   480
YYEVLGHTFF TPYFNTMRML AQLGDMRVKA TGGSTDIYGI RMLATKNSDT KATMMVWNKQ   540
GDGAASANVD ISVKNLPAGF QGKSVRYKKL LVDESHSNHA YNKIDDLQMV DEGIVNLTDT   600
IVLSQTLEKN AVMLIELEAV DPSIKNIVSA GKTVTLSPGM TGGANLVDGH DTTAAVSATN   660
TYPQTVTVDL GKSYQLAGMG IDWTNSASRG YTFKIETSLD GVNFTLASDM TFSSNPAYVP   720
PLGNSLAWFT GKARYVKLTV TGSTYDGPLS INEVKLFADG MYKNGFESVA DRDTSAWTMT   780
GYSSASTPWT FATDSVTNNT YAIPENTYGT TPSFAILGED LKDYGVEARV KVANSSYTGQ   840
VQMGLLARAG TYNNQYYFKL MRTSTTNQAI LEKRINGTTT VLATVDLPTA IDSSKWYKLN   900
LETIGTTLKG YVDGQLVIET TDTSRASGKF GLRSHDALAS FDDVRVYPIV PMLGSIKVDG   960
VTINGFDPKI NSYTVLVPSS TSTVTVTGSA YGTGSISVSP ASGQVTFDAV GQEKIYTMAA  1020
LSSEGNGANY YSLRLKQASS DATLSSLRLS MVTDPLTAPG QKLPAMSIAL IPGQTNYSIH  1080
VPSRTNYVKV VEAVPTASNV ATAQISDGVM VNGTGTAMVT VTSEAGTTMV YTLNLVANAA  1140
APTGAVLYQE DFENGSYNSD LSVGWNNGAT PNAASSHLRV VDEEQGKVLE KYTTTSTAFT  1200
VGQSAWTNYD VRARVKAQVG TSLPGVIARA SDDAKNFYML RIHNGTNGLA GGSTGYVALG  1260
RMVNGSLKEL DSKKIPYPYI AGNWYQLRLV VDGDHIKGYV DDNLIFDEID NGALFSSNPP  1320
PLTQGKAGIR VANQAARIDD FLVTELTDDV VVVPPVDTPL PFSIEGQLNR SHGLHASVLV  1380
NRTAGAPDHS GTEVVFFQLL KGTTPVAYVA MESEIGAGNR VVGHFDVADP ENLGYHVHAF  1440
VVGSWDLLNE SMPLSLSNKL DIE                                          1463

SEQ ID NO: 7            moltype = AA   length = 1493
FEATURE                 Location/Qualifiers
source                  1..1493
                        mol_type = protein
                        organism = Paenibacillus sp.
SEQUENCE: 7
MVCCNRWLVR AERKQPLCCT GFIIDREVCR MGLLKKHYAA LTAALMLTSA AVSFAPQSVH    60
AASVNMEADY AVSEGPLVRT EQFNNTNYTP LPVHVVDELK GIKTKVVRDF VKINWYYNKD   120
SANSDYLAYS IDDARNATNP DLLSARKETY DFMSQFSDSL LISLAYSYGG DANPEKNRLI   180
AGETTMNWIE FDKAMKKIIY TLKEKNPELE YIEVGNEPNL EPAFYGHTKE DIPGYMRMYQ   240
GMSEAVKWVN TQGLTGQSVK VGGPVLSGYN FDKQKQFVDI AYANGYQVDF VSWHRYQEDV   300
RMNETQEIQM KTYLHQFYPN ATTIVSEYGW KGGGGLSDAT NNVGLAKQAA FMTDSAYFYA   360
RGGTDIPMNW VAVHTLNAYF KNQFDVDYAL SNGDTTNWQS FTNSDPRSLQ YLNLRGWRES   420
ASTSKPMKIK EIRFFDSSNN PIQIPNVIND PSIAAVTDND DATQFTQSDY WTWLKFDLGA   480
NAPAIARVDI KWGNTDINTF QLIGTSDKLK YYEVLGHTFF TPYFNTMRML AQLGDMRVKA   540
```

```
TGGSTDIYGI RMLATKNSDT KATMMVWNKQ GDGAASANVD ISVKNLPAGF QGKSVRYKKL    600
LVDESHSNHA YNKIDDLQMV DEGIVNLTDT IVLSQTLEKN AVMLIELEAV DPSIKNIVSA    660
GKTVTLSPGM TGGANLVDGH DTTAAVSATN TYPQTVTVDL GKSYQLAGMG IDWTNSASRG    720
YTFKIETSLD GVNFTLASDM TFSSNPAYVP PLGNSLAWFT GKARYVKLTV TGSTYDGPLS    780
INEVKLFADG MYKNGFESVA DRDTSAWTMI GYSSASTPMF FATDSVTNNT YAIPENTYGT    840
TPSFAILGED LKDYGVEARV KVANSSYTGQ VQMGLLARAG TYNNQYYFKL MRTSTTNQAI    900
LEKRINGTTT VLATVDLPTA IDSSKWYKLN LETIGTTLKG YVDGQLVIET TDTSRASGKF    960
GLRSHDALAS FDDVRVYPIV PMLGSIKVDG VTINGFDPKI NSYTVLVPSS TSTVTVTGSA    1020
YGTGSISVSP ASGQVTFDAV GQEKIYTMAA LSSEGNGANY YSLRLKQASS DATLSSLRLS    1080
MVTDPLTAPG QKLPAMSIAL IPGQTNYSIH VPSRTNYVKV VEAVPTASNV ATAQISDGVM    1140
VNGTGTAMVT VTSEAGTTMV YTLNLVANAA APTGAVLYQE DFENGSYNSD LSVGWNNGAT    1200
PNAASSHLRV VDEEQGKVLE KYTTTSTAFT VGQSAWTNYD VRARVKAQVG TSLPGVIARA    1260
SDDAKNFYML RIHNGTNGLA GGSTGYVALG RMVNGSLKEL DSKKIPYPYI AGNWYQLRLV    1320
VDGDHIKGYV DDNLIFDEID NGALFSSNPP PLTQGKAGIR VANQAARIDD FLVTELTDDV    1380
VVVPPVDTPL PFSIEGQLNR SHGLHASVLV NRTAGAPDHS GTEVVFFQLL KGTTPVAYVA    1440
MESEIGAGNR VVGHFDVADP ENLGYHVHAF VVGSWDLLNE SMPLSLSNKL DIE           1493

SEQ ID NO: 8             moltype = AA   length = 1463
FEATURE                  Location/Qualifiers
source                   1..1463
                         mol_type = protein
                         organism = Paenibacillus sp.
SEQUENCE: 8
MGLFKKHCAA LTAALMLSSV AISFAPQSVH AASVNMEADY AVSEGPLVRT EQFNNTNYTP    60
LPVHVVDELK GIKTKVVRDF VKINWYYNKD SANSDYLAYS IDDARNATNP DLLSARKETY    120
DFMSQFSDSL LISLAYSYGG DANPEKNRLI AGETTMNWPE FDKAMKKIIY TLKEKNPELE    180
YIEVGNEPNL EPAFYGHTKD DIPGYMRMYQ GMSEAVKWVN TQGLTGHSVK VGGPVLSGYN    240
FDKQKQFVDI AYANGYQVDF VSWHRYQEDV RMNETQEIQM KGYLHQFYPN ATTIVSEYGW    300
KGGGGLSDAT NNVGLAKQAA FMTDSAYFYA RGGTDIPMNW VAVHTLNAYF KNQFDVDYAL    360
SNGDTMNWQS FTNSDPRSLQ YLNLRGWRES ASTSKPMKIK EIRFFDSSNN LIPIPNALND    420
PSIAAVTDND DATQFTQSDY WTWLKFDLGS NAPAIARVDI KWGNTDINTF QLIGTSDKLK    480
YYEVLGHTFF TPYFNTMRMF AQLGDTRVKA SGGSTDIYGT RMLATKNNDT KATMMVWNKQ    540
GDGTASANVD ISVKNLPAGF QGKSVRYKKM LVDESHSNHA YNKIDDLQMV DEGIVNLTDT    600
IVLSQTLEKN AVMLIELEAV DPSIKNIVSA GKTVTLSPGM TGGANLVDGY ETTAAVAATN    660
TYPQTVTVDL GKSYQLAGMG IDWTSSASRG YTYKIETSLD GVNFTLASDM TFSSNPAYVP    720
PLGNSLAWFT GKARYVKLTV TGSTYDGPLS INEVKVFADG MYKNGFESVA DRDTSAWTMT    780
GYSSASTPWT FATDSVTNNT YAIPVNTYGT TPSFAILGDD LKDYGVEARV KVTNSSYTGN    840
VQMGLLARAS TYNSQYYFKL MRTSTTNQAI LEKRISGTTT VLATIDLSTP IDSSKWYKLN    900
LETIGTTIKG YVDGVLVIET TDTSRTSGKF GLRSHDALAS FDDVRVYPIV PLLGSIQVDG    960
VTINGFDPKI NSYTVLVPSS TSTVTVTGSA YGTGSISVSP ASGQVTFDAV GQEKTYTIAA    1020
LSSEGNGANY YSLRLKQASS DATLSSLRLS VVTDPLTSPG QKLPAMSIAL IPGQTEYTIH    1080
VPSRTNYVKV VEAVPTASNV STAQISDGVM VNGTGTAKVT VTSEAGTTTV YTLHLVANAE    1140
APTGAVLYQE NFENGSFNSD PSTGWNNGAT PNGASSHLRV VDEDQGKVVE KYTTTSMAFT    1200
VGQSAWTNYD VRARVKAQVG TSLPGVIARA SDDAKNFYML RIHNGTNGLA GGSTGYVSLG    1260
RMVNGSLKEL DSKKIPYPYI VGNWYQLRLV VDGSHLKGYV DDNLIFDEID NGALFSVNPP    1320
ALTQGKAGIR VANQAARIDD FLVTELTDDV VVVPPVETPV PFSIEGQLNR SNGLSASVLV    1380
SRTPNATDHA GTEVVFFQLL KGTTPVSYVA MENDIGTGNR VVGHFDVADP DNLSYHVHAF    1440
VVSSWDLLNE SLPVSLSNKL DMK                                           1463

SEQ ID NO: 9             moltype = AA   length = 1463
FEATURE                  Location/Qualifiers
source                   1..1463
                         mol_type = protein
                         organism = Paenibacillus sp.
SEQUENCE: 9
MGLLRKHCAA LTAALMLTSV AVSFAPQSVH AASVNMEADY AVSEGPLVRT EQFNNTNYTP    60
LPVHVVDELK GIKTKVVRDF VKINWYYNKD STNSDYLAYS IDDARNANNP DLLSARKETY    120
DFMSQFSDSL LISLAYSYGG DANPEKNRLI AGETTMNWPE FDKAMKKIIY TLKEKNPKLE    180
YIEVGNEPNL EPAFYGHTKE DIPGYMRMYQ GMSEAVKWVN TQGLTGQSVK VGGPVLSGYN    240
FDKQKQFVDI AYANGYQVDF VSWHRYQEDV RMNETQEIEM KGYLHRFYPN ATTIVSEYGW    300
KGGGGLSDAT NNVGLAKQAA FMTDSAYFYA RGGTDIPMNW VAVHTLNAYF KNQFDVDYAL    360
SNGDTTNWQS FTNSDPRSLQ YLNLRGWRES ASTSKPMKIK EIRFFDSSNN PIPIPNVLND    420
PSIAAVTDND DATQFTQSDY WTWLKFDLGS NAPAIARVDI KWGNTDINTF QLIGTSDKLK    480
YYEVLGHTFF TPYFNTMRMF AQLGDTRVKT SGGSTDIYGT RMLATKNSDT KATMMVWNKQ    540
GDGTASANVD ISVKNLPAGF QGKSVRYKKM LVDESHSNHA YNKVDDLQMV DEGIVNLTGT    600
IVLSQTLDKN AVMLIELEAV DPSIKNIVSA GKTVTLSQGM TGGANLVDGY DTTAAMAANN    660
TYPQTVTVDL SKPYQLAGMG IDWTYSASRG YTYKIETSLD GINFTLASDK TFSSNPAYVP    720
PLGNSLAWFT GKARYVKLTV TGSTYDGPLS INEVKVFADG MYKNGFESAA DRDTSTWTMI    780
GYSSASTPWT FATDSVTNNT YAIPVNTYGT TPSFALLGED LKDYGVEARV KVANSSYTGQ    840
VQMGLLARAS TYNSQYYFKL MRTSTANQAI LEKRISGTTT VLATVDLPTA IDSSKWYKLN    900
LETIGTTLKG YVDGELVIET TDASRTSGKF GLRSHDALAS FDDVRVYPIV PLLGSIKVDG    960
VAINGFDPKI NSYTVLVPST TSTVTVTGSA YGTGSIAVSP ASGQVTFDAV GQEKTYMIAA    1020
LSSEGNGANY YSFRLKQASP DATLSSLRLS VVTDPLTDPG QKLPAMSIAL IPRQTDYTIH    1080
VPSRTNYVKV VEAVPTASNV ATAQISDAVM VNGTGIAKVT VTSEAGTSTV YTLHLVANAE    1140
APIGAVLYQE DFENGSYNVD PATGWNNGAT PNGASSHLRV VDEDQGKVLE KYTTTSMAFT    1200
VGQSAWKNYD VRARVKAQVG TSLPGVIARA SDDAKNFYML RIHNGTNGLA GGSTGYVALG    1260
RMVNGSLKEL DSKKIPYPYI VGNWYQLRLV VDGNHLKGYV DDNLIFDEID NGSLFSSNPP    1320
ALTQGKAGIR VANQAARIDD FVVTELTDDV VVVPPVDTPV PFSIQGQLNR SNGLSASVLV    1380
SHTANAVDHP GTEVVFFQLL KGTTPVSYVA IEGEMGSGNR IVGHFDVADP ENESYHVHAF    1440
```

-continued

```
VVSSLDLLNE SLPIALSNKL DLE                                                      1463

SEQ ID NO: 10          moltype = DNA   length = 20
FEATURE                Location/Qualifiers
misc_feature           1..20
                       note = OLIGONUCLEOTIDE
source                 1..20
                       mol_type = other DNA
                       organism = synthetic construct
SEQUENCE: 10
gcacccgtga atctggaagc                                                          20

SEQ ID NO: 11          moltype = DNA   length = 26
FEATURE                Location/Qualifiers
misc_feature           1..26
                       note = OLIGONUCLEOTIDE
source                 1..26
                       mol_type = other DNA
                       organism = synthetic construct
SEQUENCE: 11
ctccatagga ataagcgaga gatagg                                                   26

SEQ ID NO: 12          moltype = DNA   length = 19
FEATURE                Location/Qualifiers
misc_feature           1..19
                       note = OLIGONUCLEOTIDE
source                 1..19
                       mol_type = other DNA
                       organism = synthetic construct
SEQUENCE: 12
gagccgtcag gcaccatac                                                           19

SEQ ID NO: 13          moltype = DNA   length = 18
FEATURE                Location/Qualifiers
misc_feature           1..18
                       note = OLIGONUCLEOTIDE
source                 1..18
                       mol_type = other DNA
                       organism = synthetic construct
SEQUENCE: 13
ctctaatgca ggctgcgg                                                            18

SEQ ID NO: 14          moltype = DNA   length = 16
FEATURE                Location/Qualifiers
misc_feature           1..16
                       note = OLIGONUCLEOTIDE
source                 1..16
                       mol_type = other DNA
                       organism = synthetic construct
SEQUENCE: 14
ggctgcggcg gcacta                                                              16

SEQ ID NO: 15          moltype = DNA   length = 20
FEATURE                Location/Qualifiers
misc_feature           1..20
                       note = OLIGONUCLEOTIDE
source                 1..20
                       mol_type = other DNA
                       organism = synthetic construct
SEQUENCE: 15
tcccaaaaca tcccggatcg                                                          20

SEQ ID NO: 16          moltype = DNA   length = 20
FEATURE                Location/Qualifiers
misc_feature           1..20
                       note = OLIGONUCLEOTIDE
source                 1..20
                       mol_type = other DNA
                       organism = synthetic construct
SEQUENCE: 16
gatggcgtga aagacgatac                                                          20

SEQ ID NO: 17          moltype = DNA   length = 20
FEATURE                Location/Qualifiers
misc_feature           1..20
                       note = OLIGONUCLEOTIDE
source                 1..20
                       mol_type = other DNA
                       organism = synthetic construct
```

```
SEQUENCE: 17
acagttttgt cgttaacgcc                                                    20

SEQ ID NO: 18              moltype = DNA   length = 22
FEATURE                    Location/Qualifiers
misc_feature               1..22
                           note = OLIGONUCLEOTIDE
source                     1..22
                           mol_type = other DNA
                           organism = synthetic construct
SEQUENCE: 18
catgagggaa tcatgaaaca cg                                                 22

SEQ ID NO: 19              moltype = DNA   length = 20
FEATURE                    Location/Qualifiers
misc_feature               1..20
                           note = OLIGONUCLEOTIDE
source                     1..20
                           mol_type = other DNA
                           organism = synthetic construct
SEQUENCE: 19
gggctttctt ctcaggtacc                                                    20

SEQ ID NO: 20              moltype = DNA   length = 69
FEATURE                    Location/Qualifiers
misc_feature               1..69
                           note = OLIGONUCLEOTIDE
source                     1..69
                           mol_type = other DNA
                           organism = synthetic construct
SEQUENCE: 20
ggggacaagt ttgtacaaaa aagcaggctt cgaaggagat agaaccatgg cacccgtgaa    60
tctggaagc                                                                69

SEQ ID NO: 21              moltype = DNA   length = 56
FEATURE                    Location/Qualifiers
misc_feature               1..56
                           note = OLIGONUCLEOTIDE
source                     1..56
                           mol_type = other DNA
                           organism = synthetic construct
SEQUENCE: 21
ggggaccact ttgtacaaga aagctgggtg ctccacgatc accttattcg ataacg         56

SEQ ID NO: 22              moltype = DNA   length = 68
FEATURE                    Location/Qualifiers
misc_feature               1..68
                           note = OLIGONUCLEOTIDE
source                     1..68
                           mol_type = other DNA
                           organism = synthetic construct
SEQUENCE: 22
ggggacaagt ttgtacaaaa aagcaggctt cgaaggagat agaaccatgg agccgtcagg    60
caccatac                                                                 68

SEQ ID NO: 23              moltype = DNA   length = 48
FEATURE                    Location/Qualifiers
misc_feature               1..48
                           note = OLIGONUCLEOTIDE
source                     1..48
                           mol_type = other DNA
                           organism = synthetic construct
SEQUENCE: 23
ggggaccact ttgtacaaga aagctgggtg catccctcct gcgatgtg                    48

SEQ ID NO: 24              moltype = DNA   length = 65
FEATURE                    Location/Qualifiers
misc_feature               1..65
                           note = OLIGONUCLEOTIDE
source                     1..65
                           mol_type = other DNA
                           organism = synthetic construct
SEQUENCE: 24
ggggacaagt ttgtacaaaa aagcaggctt cgaaggagat agaaccatgg gctgcggcgg    60
cacta                                                                    65

SEQ ID NO: 25              moltype = DNA   length = 54
FEATURE                    Location/Qualifiers
misc_feature               1..54
```

-continued

```
                   note = OLIGONUCLEOTIDE
source             1..54
                   mol_type = other DNA
                   organism = synthetic construct
SEQUENCE: 25
ggggaccact ttgtacaaga aagctgggtg cttctttgcg ctcttgttat actc        54
```